United States Patent
Renhowe et al.

(10) Patent No.: US 7,598,268 B2
(45) Date of Patent: *Oct. 6, 2009

(54) QUINOLINONE DERIVATIVES

(75) Inventors: Paul A. Renhowe, Danville, CA (US); Sabina Pecchi, Oakland, CA (US); Timothy D. Machajewski, Martinez, CA (US); Cynthia M. Shafer, El Sobrante, CA (US); Clarke Taylor, Albany, CA (US); William R. McCrea, Berkeley, CA (US); Christopher McBride, Oakland, CA (US); Elisa Jazan, Richmond, CA (US)

(73) Assignee: Novartis Vaccines & Diagnostics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/886,950

(22) Filed: Jul. 8, 2004

(65) Prior Publication Data

US 2005/0054672 A1 Mar. 10, 2005

Related U.S. Application Data

(63) Continuation of application No. 10/284,017, filed on Oct. 30, 2002, now Pat. No. 6,774,237, which is a continuation of application No. 09/951,265, filed on Sep. 11, 2001, now Pat. No. 6,605,617.

(60) Provisional application No. 60/232,159, filed on Sep. 11, 2000.

(51) Int. Cl.
*A61K 31/44* (2006.01)
(52) U.S. Cl. ..................... 514/312; 546/157
(58) Field of Classification Search ................ 514/312; 546/157
See application file for complete search history.

(56) References Cited

U.S. PATENT DOCUMENTS

| | | | |
|---|---|---|---|
| 3,663,606 A | 5/1972 | Isowa |
| 4,659,657 A | 4/1987 | Harnisch et al. |
| 4,882,342 A | 11/1989 | Von der Saal et al. |
| 5,073,492 A | 12/1991 | Chen et al. |
| 5,151,360 A | 9/1992 | Handa et al. |
| 5,330,992 A | 7/1994 | Eissenstat et al. |
| 5,414,088 A | 5/1995 | Von Der Saal et al. |
| 5,585,380 A | 12/1996 | Bianco et al. |
| 5,646,153 A | 7/1997 | Spada et al. |
| 5,710,158 A | 1/1998 | Myers et al. |
| 5,763,441 A | 6/1998 | App et al. |
| 5,792,771 A | 8/1998 | App et al. |
| 5,801,212 A | 9/1998 | Okamoto et al. |
| 5,855,866 A | 1/1999 | Thorpe et al. |
| RE36,256 E | 7/1999 | Spada et al. |
| 5,942,385 A | 8/1999 | Hirth |
| 5,981,569 A | 11/1999 | App et al. |
| 6,057,320 A | 5/2000 | Spada et al. |
| 6,111,110 A | 8/2000 | Brennan et al. |
| 6,137,010 A | 10/2000 | Joo et al. |
| 6,174,912 B1 | 1/2001 | Beck et al. |
| 6,258,951 B1 | 7/2001 | Lohmann et al. |
| 6,303,600 B1 | 10/2001 | Cox et al. |
| 6,306,874 B1 | 10/2001 | Fraley et al. |
| 6,313,138 B1 | 11/2001 | Fraley et al. |
| RE37,650 E | 4/2002 | Myers et al. |
| 6,420,382 B2 | 7/2002 | Fraley et al. |
| 6,479,512 B1 | 11/2002 | Fraley et al. |
| 6,593,344 B1 | 7/2003 | Biedermann et al. |
| 6,605,617 B2 * | 8/2003 | Renhowe et al. ............ 514/312 |
| 6,759,417 B2 | 7/2004 | Renhowe et al. |
| 6,762,194 B2 | 7/2004 | Renhowe et al. |
| 6,774,237 B2 | 8/2004 | Renhowe et al. |
| 6,774,327 B1 | 8/2004 | Wong |
| 6,800,760 B2 | 10/2004 | Renhowe et al. |
| 7,179,912 B2 | 2/2007 | Halbrook et al. |

(Continued)

FOREIGN PATENT DOCUMENTS

DE 2363459 6/1975

(Continued)

OTHER PUBLICATIONS

Gontero, European Urology, vol. 46, pp. 296-311, 2004.*

(Continued)

*Primary Examiner*—D. Margaret Seaman
(74) *Attorney, Agent, or Firm*—Foley & Lardner, LLP

(57) ABSTRACT

Organic compounds having the formula I are provided where the variables have the values described herein.

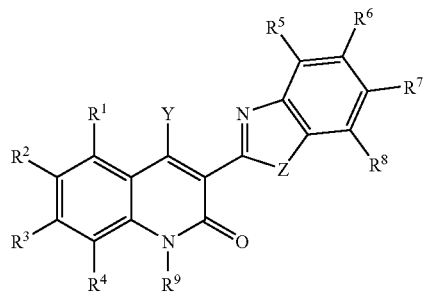

Pharmaceutical formulations include the organic compounds or pharmaceutically acceptable salts thereof and a pharmaceutically acceptable carrier and may be prepared by mixing the organic compounds or pharmaceutically acceptable salts of the organic compounds with a carrier and water. A method of treating a patient includes administering a pharmaceutical formulation according to the invention to a patient in need thereof.

5 Claims, No Drawings

U.S. PATENT DOCUMENTS

| | | |
|---|---|---|
| 2002/0103230 A1 | 8/2002 | Renhowe et al. |
| 2002/0107392 A1 | 8/2002 | Renhowe et al. |
| 2003/0028018 A1 | 2/2003 | Renhowe et al. |
| 2003/0087854 A1 | 5/2003 | Monia et al. |
| 2003/0207883 A1 | 11/2003 | Renhowe et al. |
| 2004/0002518 A1 | 1/2004 | Renhowe et al. |
| 2004/0092535 A1 | 5/2004 | Barsanti et al. |
| 2004/0097545 A1 | 5/2004 | Renhowe et al. |
| 2004/0220196 A1 | 11/2004 | Hannah et al. |
| 2005/0054672 A1 | 3/2005 | Renhowe et al. |
| 2005/0137399 A1 | 6/2005 | Cai et al. |
| 2005/0203101 A1 | 9/2005 | Barsanti et al. |
| 2005/0209247 A1 | 9/2005 | Cai et al. |
| 2005/0256157 A1 | 11/2005 | Gesner et al. |
| 2005/0261307 A1 | 11/2005 | Cai et al. |

FOREIGN PATENT DOCUMENTS

| | | |
|---|---|---|
| DE | 3634066 A1 | 7/1986 |
| DE | 19841985 | 3/2000 |
| EP | 0290153 | 11/1988 |
| EP | 0 509 717 | 4/1992 |
| EP | 0 508 800 | 10/1992 |
| EP | 0 747 771 | 12/1996 |
| EP | 0 797 376 | 9/1997 |
| EP | 0 290 153 | 11/1998 |
| EP | 1 086 705 | 3/2001 |
| HU | P0104752 | 7/2002 |
| JP | 59-130284 | 7/1984 |
| JP | 63230687 | 9/1988 |
| JP | 6-9952 | 1/1994 |
| JP | 7-43896 | 2/1995 |
| JP | 8-29973 | 2/1996 |
| JP | 63-258903 | 10/1998 |
| WO | WO 91/04974 | 4/1991 |
| WO | 92/18483 | 10/1992 |
| WO | 92/20642 | 11/1992 |
| WO | 95/15758 | 6/1995 |
| WO | 95/18801 | 7/1995 |
| WO | 97/03069 | 1/1997 |
| WO | 97/34876 | 9/1997 |
| WO | 97/48694 | 12/1997 |
| WO | 98/13350 | 4/1998 |
| WO | WO 1998/055124 | 12/1998 |
| WO | 99/10349 | 3/1999 |
| WO | 99/50263 | 10/1999 |
| WO | 99/65897 | 12/1999 |
| WO | WO 00/00481 | 1/2000 |
| WO | WO 00/03990 | 1/2000 |
| WO | WO 00/20400 | 4/2000 |
| WO | 00/27379 | 5/2000 |
| WO | WO 00/58315 | 10/2000 |
| WO | WO 00/71129 | 11/2000 |
| WO | WO 2000/74683 | 12/2000 |
| WO | 01/02369 | 1/2001 |
| WO | WO 01/12169 | 2/2001 |
| WO | 01/28993 | 4/2001 |
| WO | 01/29025 | 4/2001 |
| WO | WO 01/28993 | 4/2001 |
| WO | 01/52904 | 7/2001 |
| WO | WO 01/52875 | 7/2001 |
| WO | WO 01/53268 | 7/2001 |
| WO | 01/55114 | 8/2001 |
| WO | 01/62251 | 8/2001 |
| WO | 01/62252 | 8/2001 |
| WO | WO 01/74296 | 10/2001 |
| WO | WO 02/18383 | 3/2002 |
| WO | WO 02/22598 | 3/2002 |
| WO | 02/32861 | 4/2002 |
| WO | WO 02/26716 | 4/2002 |
| WO | WO 02/058697 | 8/2002 |
| WO | WO 03/004488 | 1/2003 |
| WO | WO 03/033472 | 4/2003 |
| WO | WO 03/087095 | 10/2003 |
| WO | WO 2004/018419 | 3/2004 |
| WO | WO 2004/030620 | 4/2004 |
| WO | WO 2004/031401 | 4/2004 |
| WO | WO 2004/043389 | 5/2004 |
| WO | WO 2004/063151 | 7/2004 |
| WO | WO 2004/063170 | 7/2004 |
| WO | WO 2004/087153 | 10/2004 |
| WO | WO 2005/046589 | 5/2005 |
| WO | WO 2005/046590 | 5/2005 |
| WO | WO 2005/053692 | 6/2005 |
| WO | WO 2005/082340 | 9/2005 |
| WO | WO 2006/081445 | 8/2006 |

OTHER PUBLICATIONS

Kirstein, CA 145:201781, abstract only of Recent Patents on Anti-cancer Drug Discovery, vol. 1(2), pp. 153-161, 2006.*

Salmon, S. E. et al., *Basic & Clincial Pharmacology, Seventh Edition*, edited by B. Katzung, Appleton & Lange, pp. 29, 881-884 (1998).

Milauer, B. et al., "Glioblastoma Growth Inhibited in Vivo by a Dominant-Negative Flk-1 Mutant," *Nature*, vol. 367, pp. 576-579 (1994); published by Nature Publishing Group.

Pinedo, H. M. et al., "Translational Research: The Role of VEGF in Tumor Angiogenesis," *The Oncologist 2000*, vol. 5 (suppl. 1), pp. 1-2 (2000).

McMahon, G., "VEGF receptor Signaling in Tumor Angiogenesis," *The Oncologist 2000*, vol. 5 (suppl. 1), pp. 3-10 (2000).

European Search Report dated Feb. 28, 2006 for EP 05017665.0.

Cecil, Textbook of Medicine, 21$^{st}$ Edition (2000), Goldman & Bennett (Editors), W.B. Saunders Company (Publisher). Chapter 198, pp. 1060-1074.

Ukrainets, I. V. et al., "Effective Synthesis of 3-(Benzimidazol-2-yl)-4-Hydroxy-2-Oxo-1,2-Dihydroquinolines," *Tetrahedron Letters*, vol. 36, No. 42, pp. 7747-7748, 1995; published by Elsevier Science Ltd. (Pergamon).

Heise, C. et al., "In vivo Preclinical Evaluation of Tyrosine Kinase Inhibitors with Potent Effects on Tumor Angiogenesis, Growth and Metastasis," Abstract and material for a presentation at the American Association for Cancer Research meeting held in Apr. 2002.

Beebe, J. S. et al., "Pharmacological Characterization of CP-547,632, a Novel Vascular Endothelial Growth Factor Receptor-2 Tyrosine Kinase Inhibitor for *Cancer Therapy*," Cancer Research, vol. 63, pp. 7301-7309, Nov. 2003;.

Lee, S. H. et al., "In vivo Target Modulation and Biological Activity of CHIR-258, a Multitargeted Growth Factor Receptor Kinase Inhibitor, in Colon Cancer Models," *Clin. Cancer Res.*, vol. 11, No. 10, pp. 3633-3641, May 15, 2005.

Lopes de Menezes, D. E. et al., "CHIR-258: A Potent Inhibitor of FLT3 Kinase in Experimental Tumor Xenograft Models of Human Acute Myelogenous Leukemia," *Clin. Cancer Res.*, vol. 11, No. 14, pp. 5281-5291, Jul. 15, 2005.

Trudel, S. et al., "CHIR-258, a novel multitargeted tyrosine kinase inhibitor for the potential treatment of t(f;14) multiple myeloma," *Blood*, vol. 105, No. 7, Apr. 1, 2005; published by The American Society of Hematology.

Wedge, S. R. et al., "ZD6474 Inhibits Vascular Endothelial Growth Factor Signaling, Angiogenesis, and Tumor Growth following Oral Administration," *Cancer Research*, vol. 62, pp. 4645-4655, Aug. 15, 2002.

Aprelikova, O., et al., "FLT4, a novel Class III Receptor Tyrosine Kinase in chromosome 5q33-qter1," Cancer Res., vol. 52, pp. 746-748, Feb. 1, 1992, published by The American Association for Cancer Research, Stanford University Libraries' High Wire Press, California, United States of America.

Carmeliet, P. et al., "Angiogenesis in Cancer and Other Diseases," Nature, 407, pp. 249-257 (2000).

Connolly, D., et al., "Human Vascular Permeability Factor," J. Biol. Chem., vol. 264, pp. 20017-20024, 1989, published by The American Society For Biochemistry and Molecular Biology, Inc., Stanford University Libraries' High Wire Press, California, United States of America.

Connolly, D., et al., "Tumor Vascular Permeability Factor Stimulates Endothelial Cell Growth and Angiogenesis," J. Clin. Invest., vol. 84, pp. 1470-1478, Nov. 1989, published by The American Society for Clinical Investigation, Inc., Stanford University Libraries' High Wire Press, California, United States of America.

DeVries, C., et al., "The fms-Like Tyrosine Kinase, a Receptor for Vascular Endothelial Growth Factor," Science, vol. 255, pp. 989-991, Feb. 21, 1992, published by The American Society for the Advancement of Science, Stanford University Libraries' High Wire Press, California, United States of America.

Ferrara, N., et al., "The Biology of Vascular Endothelial Growth Factor," Endocrinol. Rev., vol. 18, No. 1, pp. 4-25, 1997 published by The Endocrine Society, Stanford University Libraries' High Wire Press, California, United States of America.

Folkman, J., "Fighting Cancer by Attacking its Blood Supply," Scientific American, vol. 275, pp. 150-154, Sep., 1996, published by Scientific American, Inc., New York, New York, United States of America.

Hennequin, L. F., et al., Design and Structure Activity Relationship of a New Class of Potent VEGF Receptor Tyrosine Kinase Inhibitors,: J. Med. Chem., vol. 42, No. 26, pp. 5369-5359, 1999; published by American Chemical Society, Washington, D.C.

Leung, D., et al., "Vascular Endothelial Growth Factor Is a Secreted Angiogenic Mitogen," Science, vol. 246, pp. 1306-1309, Dec. 8, 1989, published by The American Society for the Advancement of Science, Stanford University Libraries' High Wire Press, California, United States of America.

Lymboussaki, A., "Vascular endothelial growth factors and their receptors in embryos, adults, and in tumors," Academic Dissertation, University of Helsinki, Molecular/Cancer Biology Laboratory and Department of Pathology, Haartman Institute, 1999.

Maguire, M.P., et al., "A New Series of PDGF Receptor Tyrosine Kinase Inhibitors: 3-Substituted Quinoline Derivatives," J. Med. Chem., vol. 37, No. 14, pp. 2129-2137, 1994; published by American Chemical Society, Washington, D.C.

Matei, S., et al., "Condensation of ethyl 2-benzimidazoleacetate with carbonyl compounds," Rev. Chim., vol. 33, No. 6, pp. 527-530, 1989, published by the Central Institute of Chemistry, Bucharest, Romania.

Mustonen, T., et al., "Endothelial Receptor Tyrosine Kinases Involved in Angiogenesis," J. Cell Biology, vol. 129, No. 4, pp. 895-898, May 1995, published by The Rockfeller University Press, New York, New York, United States of America.

Plouet, J., et al., "Isolation and characterization of a newly identified endothelial cell mitogen produced by AtT-20 cells," EMBO J., vol. 8, No. 12, pp. 3801-3806, 1989, published by IRL Press.

Quinn, T., et al., "Fetal liver kinase 1 is a receptor for vascular endothelial growth factor and is selectively expressed in vascular endothelium," Proc. Natl. Acad. Sci. USA, vol. 90, pp. 7533-7537, Aug. 1993.

Shibuya, M., et al., "Nucleotide sequence and expression of a novel human receptor-type tyrosine kinase gene (flt) closely related to the fms family," Oncogene, vol. 5, pp. 519-524, 1990, published by Macmillan Press Ltd., Stockton Press Company, Great Britain.

Stover, D. R., "Recent advances in protein kinase inhibition: Current molecular scaffolds used for inhibitor synthesis," Current Opinion in Drug Discovery & Development, vol. 2, No. 4, pp. 274-285, 1999; published by PharmaPress Ltd., London, United Kingdom.

Terman, B., et al., "Identification of a new endothelial cell growth factor receptor tyrosine kinase," Oncogene, vol. 6, pp. 1677-1683, 1991, published by Macmillan Press Ltd., Stockton Press Company, Great Britain.

Ukrainets, I., "Effective Synthesis of 3-(Benzimidazol-2y-yl)-4-Hydroxy-2-Oxo-1,2-Dihydroquinolines," Tet. Lett., vol. 36, No. 42, pp. 7747-7748, 1995, published by Elsevier Science Ltd., Great Britain.

Ukrainets, I., et al., "2-Carbethoxymethyl-4H-3,1-Benzoxazin-4-One. 3.*Condensation of o-Phenylenediamine," pp. 198-200, translated from Khimiya Geterotsiklicheskikh Soedinii, No. 2, pp. 239-241, Feb., 1992, published by Plenum Publ. Corp., London, Great Britain.

Ukrainets, I., et al., "4-Hydroxy-2-Quinolones 7.* Synthesis and Biological Properties of 1-R-3-(2-Benzimidazolyl)-4-Hydroxy-2-Quinolones," pp. 92-94, translated from Khimiya Geterotsiklicheskikh Soedinii, No. 1, pp. 105-108, Jan. 1993, published by Plenum Publ. Corp., London, Great Britain.

Ukrainets, I., et al., "4-Hydroxy-2-Quinolones. 16.* Condensation of N-R-Substituted Amides of 2-Carboxy-Malonanilic Acid With o-Phenylenediamine," pp. 941-944, translated from Khimiya Geterotsiklicheskikh Soedinii, vol. 8, pp. 1105-1108, Aug. 1993, published by Plenum Publ. Corp., London, Great Britain.

Ukrainets, I., et al., "4-Hydroxy-2-Quinolones. 32.* Synthesis and Antithyroid Activity of Thio Analogs of 1H-2-OXO-3-(2-Benzimidazolyl)-4-HydroxyQuinoline," Chem. Heterocyclic Comp., vol. 33, No. 5, pp. 600-604, 1997, published by Kluwer Academic Publishers, London, Great Britain.

Ullrich, A., et al., "Signal Transduction by Receptors with Tyrosine Kinase Activity," Cell, vol. 61, pp. 203-212, Apr. 20, 1990, published by Cell Press, Cambridge, Massachusetts, United States of America.

van der Geer, P., et al., "Receptor Protein-Tyrosine Kinases and Their Signal Transduction Pathways," Annu. Rev. Cell Biol., vol. 10, pp. 251-337, 1994, published by Annual Reviews, Inc., Palo Alto, California, United States of America.

List of compounds purchased from various vendors (3 pages).

CAS printout for 308476-79-7 Registry File, entry date into Registry File Nov. 29, 2000.

CAS printout for 300591-52-0 Registry File, entry date into Registry File Oct. 31, 2000.

Grand, et al., Targeting FGFR3 in Multiple Myeloma: Inhibition of t(4;14) Positive Cells by SU5402 and PD173074, Leukemia, 2004, vol. 18, pp. 962-966.

Dalton, et al., "Multiple Myeloma," Hematology. Am. Soc. Hematol. Educ. Program, 2001, 157-77.

International Search Report for PCT/US04/36956 dated Oct. 2, 2006.

Antonios-McCrea, W. R. et al., "LHMDS mediated tandem acylation-cyclization of 2-aminobenzenecarbonitriles with 2-benzymidazol-2-yl acetates: a short and efficient route to the synthesis of 4-amino-3-benzimidazol-2-ylhydroquinolin-2-ones," Tetrahedron Letters, vol. 47, 2006, pp. 657-660; published by Elsevier Ltd.

Bastin et al. Salt selection and Optimisation procedures for pharmaceutical new chemical entities, organic process research & development 2000, 4, 427-35.

Beals, C. R. et al., "Nuclear Export of NF-ATc Enhanced by Glycogen Synthase Kinase-3," Science, vol. 275, pp. 1930-1933, Mar. 18, 1997.

Beck, J. R., "A Direct Synthesis of Benzo[b]thiophene-2-carboxylate Esters Involving Nitro Displacement," J. Org. Chem., vol. 37, No. 21, 1972, pp. 3224-3226.

Berwanger, B. et al., "Loss of a FYN-regulated differentiation and growth arrest pathway in advanced stage neuroblastoma," Cancer Cell, vol. 2, Nov. 2002, pp. 377-386; published by Cell Press.

Brownlees, J. et al., "Tau phosphorylation in transgenic mice expressing glycogen synthase kinase-3β transgenes," NeuroReport, vol. 8, No. 15, pp. 3251-3255, Oct. 20, 1997; published by Rapid Science Publishers.

Caira, Mino R., "Crystalline polymorphism of Organic Compounds," Topics in Current Chemistry, vol. 198, Springer Verlag 1998.

Carling, R. W. et al., "4-Substituted-3-phenylquinolin-2(1H)-ones: Acidic and Nonacidic Glycine Site N-Methyl-D-aspartate Antagonists with in Vivo Activity," J. Med. Chem., vol. 40, 1997, pp. 754-765; published by American Chemical Society.

Chan, T. A. et al., "14-3-3σ is required to prevent mitotic catastrophe after DNA damage," Nature, vol. 401, pp. 616-620, Oct. 7, 1999; published by Macmillan Magazines Ltd.

Charvat, T. et al., "Diethyl Acetonedicarboxylate—a Precursor for the Synthesis of New Substituted 4-Aminoquinolines and Fused 4-Aminopyridines," Monatshefte für Chemie, vol. 126, 1995, pp. 333-340.

Chen, G. et al., "The Mood-Stabilizing Agent Valproate Inhibits the Activity of Glycogen Synthase Kinase-3," J. Neurochem., vol. 72, No. 3, 1999, pp. 1327-1330; published by Lippincott Williams & Wilkins, Inc., Philadelphia.

Chesi, M. et al., "Activated fibroblast growth factor receptor 3 is an oncogene that contributes to tumor progression in multiple myeloma," *Blood*, vol. 97, No. 3, pp. 729-736, Feb. 1, 2001; published by The American Society of Hematology.

Cross, A. E. et al., "The inhibition of glycogen synthase kinase-3 by insulin or insulin-like growth factor 1 in the rat skeletal muscle cell line L6 blocked by wortmannin, but not by rapamycin: evidence that wortmannin blocks activation of the mitogen-activated protein kinase pathway in L6 cells between Ras and Raf," *Biochem J.*, vol. 303, pp. 21-26, 1994; (printed in Great Britain).

Danish Search Report for Singapore Patent Application No. 200501676-1 dated Feb. 28, 2006.

Danish Written Opinion for Singapore Patent Application No. 200501676-1 dated Sep. 20, 2007.

Doukas, M. A. et al., "Effect of Lithium on Stem Cell and Stromal Cell Proliferation in vitro," *Exp. Hematol.*, vol. 14, pp. 215-221, 1986; published by International Society for Experimental Hematology.

European Communication for EP 01973722.0 dated Mar. 16, 2004.

European Communication for EP 03746614.1 dated Nov. 6, 2007.

European Supplementary Search Report for EP 03746614.1 dated May 24, 2007.

European Partial Search Report for EP 07011978 dated Sep. 19, 2007.

Flückiger-Isler, R. E. et al., "Stimulation of rat liver glycogen synthesis by the adenosine kinase inhibitor 5-iodotubercidin," *Biochem. J.*, vol. 292, pp. 85-91, 1993; (printed in Great Britain).

Gewald, K. et al., "4-Amino-3-pyridiniochinolin-2(1H)-on-chloride und 3,4-Diaminochinolin-2(1H)-one," Chem. Ber., vol. 124, 1991, pp. 1237-1241, Eng. Abstract provided; published by VCH Veriagsgesellschaft mbH.

Hammond, W. P. et al., "Lithium Therapy of Canine Cyclic Hematopoiesis," *Blood*, vol. 55, No. 1, pp. 26-28, Jan., 1980.

Heinrich, M. C. et al., "Inhibition of KIT Tyrosine Kinase Activity: A Novel Molecular Approach to the Treatment of KIT-Positive Malignancies," *J. Clin. Oncol.*, vol. 20, No. 6, pp. 1692-1703, Mar. 15, 2002.

Hirao, A. et al., "DNA Damage-Induced Activation of p53 by the Checkpoint Kinase CHk2," *Science*, vol. 287, pp. 1824-1827, Mar. 10, 2000.

Hiyama, T. et al., "A New Synthesis of 3-Amino-2-Alkenoates," *Tetrahedron Letters*, vol. 23, No. 15, 1982, pp. 1597-1600; published by Pergamon Press Ltd.

International Search Report for PCT/US00/13420 dated Aug. 14, 2000.

International Search Report for PCT/US01/42131 dated Mar. 6, 2002.

International Search Report for PCT/US03/10463 dated Jun. 12, 2003.

International Preliminary Examination Report for PCT/US03/10463 dated Jun. 8, 2004.

International Search Report for PCT/US06/19349 dated Sep. 11, 2006.

International Search Report for PCT/US2006/020296 dated Nov. 14, 2006.

Johnson et al., "Relationships between drug activity in NCI preclinical in vitro and in vivo models and early clinical trials," *British Journal of Cancer*, vol. 84, No. 10, 2001, pp. 1424-1431.

Klein, P. S. et al., "A molecular mechanism for the effect of lithium on development," *Proc. Natl. Acad. Sci. USA*, vol. 93, pp. 8455-8459, Aug. 1996.

Kreimeyer, A. et al., "Evaluation and Biological Properties of Reactive Ligands for the Mapping of the Glycine Site on the N-Methyl-D-aspartate (NMDA) Receptor," *J. Med. Chem.*, vol. 42, 1999, pp. 4394-4404; published by American Chemical Society.

Lee, J. et al., "Positive Regulation of Wee1 by Chk1 and 14-3-3 Proteins," *Molecular Biology of the Cell*, vol. 12, pp. 551-563, Mar. 2001; published by The American Society for Cell Biology.

Levis, M. et al., "A FLT3-targeted tyrosine kinase inhibitor is cytotoxic to leukemia cells in vitro and in vivo," *Blood*, vol. 99, No. 11, pp. 3885-3891, Jun. 1, 2002; published by the American Society of Hematology.

Liu, Q. et al., "Chk1 is an essential kinase that is regulated by Atr and required for the $G_2$/M DNA damage checkpoint," *Genes & Development*, vol. 14, 2000, pp. 1448-1459; published by Cold Springs Harbor Laboratory Press.

Lopez-Girona, A. et al., "Nuclear localization of Cdc25 is regulated by DNA damage and a 14-3-3 protein," *Nature*, vol. 397, pp. 172-175, Jan. 14, 1999; published by Macmillan Magazines Ltd.

Lovestone, S. et al., "Alzheimer's disease-like phosphorylation of the microtubule-associated protein tau by glycogen synthase kinase-3 in transfected mammalian cells," *Current Biology*, vol. 4, pp. 1077-1086, Dec. 1, 1994; published by Elsevier Science Ltd.

Majolini, M. B. et al., "Dysregulation of the Protein Tyrosine Kinase LCK in Lymphoproliferative Disorders and in Other Neoplasias," *Leukemia and Lymphoma*, vol. 35(3-4), 1999, pp. 245-254; published by OPA (Overseas Publishers Association) N.V.

Massillon, D. et al., "Identification of the glycogenic compound 5-iodotubercidin as a general protein kinase inhibitor," *Biochem. J.*, vol. 299, pp. 123-128, 1994; printed in Great Britain.

Mundy, "Preclinical models of bone metastases," *Semin. Oncol.*, 28(4 Suppl. 11), 2001, pp. 2-8.

Nonaka, S. et al., "Chronic lithium treatment robustly protects neurons in the central nervous system against excitotoxicity by inhibiting N-methyl-D-aspartate receptor-mediated calcium influx," *Proc. Natl. Acad. Sci. USA*, vol. 95, pp. 2642-2647, Mar. 1998.

Parham, W. E. et al., "Elaboration of Bromoarylnitriles," *J. Org. Chem.*, vol. 41, No. 7, 1976, pp. 1187-1191.

Parker, L. L. et al., "Inactivation of the p34cdc2-Cyclin B Complex by the Human WEE1 Tyrosine Kinase," *Science*, vol. 257, pp. 1955-1957, Sep. 25, 1992.

Pei, J.-J. et al., "Distribution, Levels, and Activity of Glycogen Synthase Kinase-3 in the Alzheimer Disease Brain," *Journal of Neuropathology and Experimental Neurology*, vol. 56, No. 1, pp. 70-78, Jan., 1997; published by the American Association of Neuropathologists.

Peng, C.-Y. et al., "Mitotic and $G_2$ Checkpoint Control: Regulation of 14-3-3 Protein Binding by Phosphorylation of Cdc25C on Serine-216," *Science*, vol. 277, pp. 1501-1505, Sep. 5, 1997.

Saito, Y. et al., "The mechanism by which epidermal growth factor inhibits glycogen synthase kinase 3 in A431 cells," *Biochem. J.*, vol. 303, pp. 27-31, 1994; printed in Great Britain.

Sanchez, Y. et al., "Conservation of the Chk1 Checkpoint Pathway in Mammals: Linkage of DNA Damage to Cdk Regulation Through Cdc25," *Science*, vol. 277, pp. 1497-1501, Sep. 5, 1997.

Schäfer, H. et al., "Zur Synthese von 4-Aminochinolinen und -chinolinonen-(2) aus Anthranilsäurenitril," *Journal f. prakt. Chemie*, Band 321, Heft 4, 1979, pp. 695-698, Eng. Abstract included.

Siemeister, G. et al., "Two Independent Mechanisms Essential for Tumor Angiogenesis: Inhibition of Human Melanoma Xenograft Growth by Interfering with either the Vascular Endothelial Growth Factor Receptor Pathway or the Tie-2 Pathway," *Cancer Research*, vol. 59, Jul. 1, 1999, pp. 3185-3191.

Smolich, B.D. et al., "The antiangiogenic protein kinase inhibitors SU5416 and SU6668 inhibit the SCF receptor (c-kit) in a human myeloid leukemia cell line and in acute myeloid leukemia blasts," *Blood*, vol. 97, No. 5, pp. 1413-1421, Mar. 1, 2001; published by The American Society of Hematology.

Stambolic, V. et al., "Lithium inhibits glycogen synthase kinase-3 activity and mimics Wingless signaling in intact cells," *Current Biology*, vol. 6, No. 12, pp. 1664-1668, 1996; published by Current Biology Ltd. ISSN 0960-9822.

Suggitt et al., "50 Years of Preclinical Anticancer Drug Screening: Empirical to Target-Driven Approaches," *Clinical Cancer Research*, vol. 11, 2005, pp. 971-981.

Sun, T-Q. et al., "PAR-1 is a Dishevelled-associated kinase and a positive regulator of Wnt signalling," *Nature Cell Biology*, vol. 3, pp. 628-636, Jul. 2001; published by Macmillan Magazines Ltd.

Takashima, A. et al., "Presenilin 1 associates with glycogen synthase kinase-3β and its substrate tau," *Proc. Natl. Acad. Sci. USA*, vol. 95, pp. 9637-9641, Aug. 1998; published by The National Academy of Sciences.

Takashima, A. et al., "tau protein kinase I is essential for amyloid β-protein-induced neurotoxicity," *Proc. Natl. Acad. Sci. USA*, vol. 90, pp. 7789-7793, Aug. 1993.

Thomas, M.D., R. J. et al., "Progress in Geriatrics: Excitatory Amino Acids in Health and Disease," *J. of the American Geriatrics Society*, vol. 43, No. 11, Nov. 1995; published by American Geriatrics Society.

Valtola, R. et al., "VEGFR-3 and its Ligand VEGF-C Are Associated with Angiogenesis in Breast Cancer," *American Journal of Pathology*, vol. 154, No. 5, May 1999, pp. 1381-1390; published by American Society for Investigative Pathology.

Veronese, A. C. et al., "Tin(IV) Choloride-promoted vs. Metal βCarbonyl-enolate-catalysed Reactions of β-Dicarbonyls with Nitriles," *J. Chem Research* (S), 1988, pp. 246-247.

Veronese, A. C. et al., "Tin (IV) Chloride-promoted Synthesis of 4-Aminopyridines and 4-Aminoquinolines," *Tetrahedron*, vol. 51, No. 45, 1995, pp. 12277-12284; published by Elsevier Science Ltd.

Vogelstein, B. et al., "Surfing the p53 network," *Nature*, vol. 408, pp. 307-310, Nov. 16, 2000; published by Macmillan Magazines Ltd.

Welsh, G. I. et al., "Glycogen synthase kinase-3 is rapidly inactivated in response to insulin and phosphorylates eukaryotic initiation factor eIF-2B," *Biochem. J.*, vol. 294, pp. 625-629, 1993; printed in Great Britain.

Winstead, E., "p53 Gene May Help Fight Tumors," *NCI Cancer Bulletin*, vol. 4, No. 5, pp. 1-2, 2007.

Yao et al., "Cell-specific but p53-independent Regulation of Vascular Endothelial Growth Factor Expression by Interferons in Human Glioblastoma Cells," *Journal of Neuro-Oncology*, vol. 76, pp. 219-225, 2006.

Yamasaki, Y. et al., "Pioglitazone (AD-4833) Ameliorates Insulin Resistance in Patients with NIDDM," *Tohoku J. Exp. Med.*, vol. 183, pp. 173-183, 1997.

Yoo, et al., "Synchronous Elevation of Soluble Intercellular Adhesion Molecule-1 (ICAM-1) and Vascular Cell Adhesion Molecule-1 (VCAM-1) Correlates with Gastric Cancer Progression," *Yonsei Medical Journal*, vol. 39, No. 1, pp. 27-36, 1998.

Zeng et al., "HDAC3 is crucial in shear- and VEGF-induced stem cell differentiation toward endothelial cells," *The Journal of Cell Biology*, vol. 174, No. 7, pp. 1059-1069, 2006.

Zhang, Z. et al., "Destabilization of β-catenin by mutations in presenilin-1 potentiates neuronal apoptosis," *Nature*, vol. 395, pp. 698-702, Oct. 15, 1998; published by Macmillan Publishers Ltd.

Zhao, H. et al., "ATR-Mediated Checkpoint Pathways Regulate Phosphorylation and Activation of Human Chk1," *Molecular and Cellular Biology*, vol. 21, No. 13, pp. 4129-4139, Jul. 2001; published by American Society for Microbiology.

Berge, et al., Pharmaceutical Salts, *J. Pharm. Sci*, vol. 66, No. 1, pp. 1-19., 1977.

Non-Final Office Action for U.S. Appl. No. 10/706,328 dated Aug. 26, 2008.

Guideline for the Format and Content of the Human Pharmacokinetic and Bioavailability Section of an Application, Center for Drugs and Biologics, FDA, Department of Health and Human Services, pp. 1-18, Feb. 1997.

Zetter, B. R., "Angiogenesis and Tumor Metastasis," Annu. Rev. Med., 1998, vol. 49, pp. 407-24; published by Annual Review Inc.

MSNBC News Services, "Mixed results on new cancer drug," Nov. 9, 2000.

Gura, T., "Systems for Identifying New Drugs Are Often Faulty," *Science*, 1997, vol. 278, pp. 1041-1042.

Dermer, G. B., "Another Anniversary for the War on Cancer," *Biotechnology*, 1994, vol. 12, p. 320.

Freshney, R. I., *Culture of Animal Cells — A Manual of Basic Technique*, 1983, pp. 1-4; published by Alan R. Liss, Inc.

Angiogenesis Foundation, "New Study Shows That Acute Myeloid Leukemia is Angiogenesis-Dependent," Jan. 4, 2000; www.anoio.org/newsandviews/ archive2000/jan_4_2000.html.

Hussong, J. W. et al., "Evidence of increased angiogenesis in acute myeloid leukemia," *Blood*, 2000, vol. 95(1), pp. 309-313; The American Society of Hematology.

Kerbel, R. S., "Tumor Angiogenesis: Past, Present and Near Future," *Carcinogenesis*, 2000, vol. 21(3), pp. 505-515; Oxford University Press.

Lundberg, L. G. et al., "Bone Marrow in Polycythemia Vera, Chronic Myelocytic Leukemia, and Myelofibrosis Has an Increased Vascularity," *American Journal of Pathology*, 2000, vol. 157(1), pp. 15-19.

Dankbar, B. et al., "Vascular endothelial growth factor and interleukin-6 in paracrine tumor-stromal cell interactions in multiple myeloma," *Blood*, 2000, vol. 5(8), pp. 2630-2636.

Menzel, T. et al., "Elevated Intracellular Level of Basic Fibroblast Growth Factor Correlates with Stage of Chronic Lymphocytic Leukemia and is Associated With Resistance to Fludarabine," *Blood*, 1996, vol. 87(3), pp. 1056-1063.

Gruber, G. et al., "Basic Fibroblast Growth Factor is Expressed in CD19/CD11c-Positive Cells in Hairy Cell Leukemia," *Blood*, 1999, vol. 94(3), pp. 1077-1085.

Angiogenesis Foundation, "New Study Shows that Acute Myeloid Leukemia is Angiogenesis Dependent," Jan. 4, 2000.

Dermer, G., "Another Anniversary for the War on Cancer," BioTechnology, vol. 12, 1994. p. 320.

Final Office Action for U.S. Appl. No. 11/866,296 dated Nov. 17, 2008.

Menzel, T. et al., "Elevated Intracellular Level of Basic Fibroblast Growth Factor Correlates with Stage of Chronic Lymphocytic Leukemia and is Associated With Resistance to Fludarabine," *Blood*, 1996, vol. 87(3), pp. 1056-1063.

* cited by examiner

QUINOLINONE DERIVATIVES

CROSS-REFERENCES TO RELATED APPLICATIONS

This application is a continuation of and claims priority to U.S. patent application Ser. No. 10/284,017, filed on Oct. 30, 2002, which is a continuation of and claims priority to U.S. patent application Ser. No. 09/951,265 filed on Sep. 11, 2001, now U.S. Pat. No. 6,605,617, which claims priority to U.S. Provisional Application No. 60/232,159 filed on Sep. 11, 2000, the entire disclosures each of which are incorporated herein by reference for all purposes as if fully set forth in their entireties.

FIELD OF THE INVENTION

This invention pertains generally to treating diseases characterized by angiogenesis including cancer. More specifically, the invention described herein pertains to treating diseases characterized by activity of vascular endothelial growth factor receptor tyrosine kinases. The present invention provides, small molecule inhibitors of vascular endothelial growth factor receptor tyrosine kinase, pharmaceutical formulations containing such inhibitors, methods of treating patients with such pharmaceutical formulations, and to methods of preparing such pharmaceutical formulations and inhibitors.

BACKGROUND OF THE INVENTION

Capillaries reach into almost all tissues of the human body and supply tissues with oxygen and nutrients as well as removing waste products. Under typical conditions, the endothelial cells lining the capillaries do not divide, and capillaries, therefore, do not normally increase in number or size in a human adult. Under certain normal conditions, however, such as when a tissue is damaged, or during certain parts of the menstrual cycle, the capillaries begin to proliferate rapidly. This process of forming new capillaries from pre-existing blood vessels is known as angiogenesis or neovascularization. See Folkman, J. Scientific American 275,150-154 (1996). Angiogenesis during wound healing is an example of pathophysiological neovascularization during adult life. During wound healing, the additional capillaries provide a supply of oxygen and nutrients, promote granulation tissue, and aid in waste removal. After termination of the healing process, the capillaries normally regress. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999).

Angiogenesis also plays an important role in the growth of cancer cells. It is known that once a nest of cancer cells reaches a certain size, roughly 1 to 2 mm in diameter, the cancer cells must develop a blood supply in order for the tumor to grow larger as diffusion will not be sufficient to supply the cancer cells with enough oxygen and nutrients. Thus, inhibition of angiogenesis is expected to halt the growth of cancer cells.

Receptor tyrosine kinases (RTKs) are transmembrane polypeptides that regulate developmental cell growth and differentiation, remodeling and regeneration of adult tissues. Mustonen, T. et al., J. Cell Biology 129, 895-898 (1995); van der Geer, P. et al. Ann Rev. Cell Biol. 10, 251-337 (1994). Polypeptide ligands known as growth factors or cytokines, are known to activate RTKs. Signaling RTKs involves ligand binding and a shift in conformation in the external domain of the receptor resulting in its dimerization. Lymboussaki, A. "Vascular Endothelial Growth Factors and their Receptors in Embryos, Adults, and in Tumors" Academic Dissertation, University of Helsinki, Molecular/Cancer Biology Laboratory and Department of Pathology, Haartman Institute, (1999); Ullrich, A. et al., Cell 61, 203-212 (1990). Binding of the ligand to the RTK results in receptor trans-phosphorylation at specific tyrosine residues and subsequent activation of the catalytic domains for the phosphorylation of cytoplasmic substrates. Id.

Two subfamilies of RTKs are specific to the vascular endothelium. These include the vascular endothelial growth factor (VEGF) subfamily and the Tie receptor subfamily. Class III RTKs include VEGFR-1, VEGFR-2, and VEGFR-3. Shibuya, M. et al., Oncogene 5, 519-525 (1990); Terman, B. et al., Oncogene 6, 1677-1683 (1991); Aprelikova, O. et al., Cancer Res. 52, 746-748 (1992).

Members of the VEGF subfamily have been described as being able to induce vascular permeability and endothelial cell proliferation and further identified as a major inducer of angiogenesis and vasculogenesis. Ferrara, N. et al., Endocrinol. Rev. 18, 4-25 (1997). VEGF is known to specifically bind to RTKs including VEGFR-1 and VEGFR-2. DeVries, C. et al., Science 255, 989-991 (1992); Quinn, T. et al., Proc. Natl. Acad. Sci. 90, 7533-7537 (1993). VEGF stimulates the migration and proliferation of endothelial cells and induces angiogenesis both in vitro and in vivo. Connolly, D. et al., J. Biol. Chem. 264, 20017-20024 (1989); Connolly, D. et al., J. Clin. Invest. 84, 1470-1478 (1989); Ferrara, N. et al., Endocrino. Rew. 18, 4-25 (1997); Leung, D. et al., Science 246, 1306-1309 (1989); Plouet, J. et al., EMBO J 8, 3801-3806 (1989).

Because angiogenesis is known to be critical to the growth of cancer and to be controlled by VEGF and VEGF-RTK, substantial efforts have been undertaken to develop therapeutics that are antagonists of VEGF-RTK to thereby inhibit or retard angiogenesis, and, hopefully, interfere or stop tumor proliferation.

A wide variety of chemical compounds and compositions have been reported as having activity against one of more the VEGF-RTKs. Examples include quinoline derivatives such as described in WO 98/13350, aminonicotinamide derivatives (see, e.g., WO 01/55114), antisense compounds (see, e.g., WO 01/52904), peptidomimetics (see, e.g., WO 01/52875), quinazoline derivatives (see, e.g., U.S. Pat. No. 6,258,951) monoclonal antibodies (see, e.g., EP 1 086 705 A1), various 5,10,15,20-tetraaryl-porphyrins and 5,10,15-triaryl-corroles (see, e.g., WO 00/27379), heterocyclic alkanesulfonic and alkane carboxylic acid derivatives (see, e.g., DE19841985), oxindolylquinazoline derivatives (see, e.g., WO 99/10349), 1,4-diazaanthracine derivatives (see, e.g., U.S. Pat. No. 5,763,441), and cinnoline derivatives (see, e.g., WO 97/34876), and various indazole compounds (see, e.g., WO 01/02369 and WO 01/53268).

Various indolyl substituted compounds have recently been disclosed in WO 01/29025, WO 01/62251, and WO 01/62252, and various benzimidazolyl compounds have recently been disclosed in WO 01/28993. These compounds are reportedly capable of inhibiting, modulating, and/or regulating signal transduction of both receptor-type and non-receptor tyrosine kinases. Some of the disclosed compounds contain a quinolone fragment bonded to the indolyl or benzimidazolyl group.

The synthesis of 4-hydroxy quinolone and 4-hydroxy quinoline derivatives is disclosed in a number of references. For example, Ukrainets et al. have disclosed the synthesis of 3-(benzimidazol-2-yl)-4-hydroxy-2-oxo-1,2-dihydroquinoline. Ukrainets, I. et al., Tet. Lett. 42, 7747-7748 (1995); Ukrainets, I. et al., Khimiya Geterotsiklicheskikh Soedinii, 2, 239-241(1992). Ukrainets has also disclosed the synthesis, anticonvulsive and antithyroid activity of other 4-hydroxy quinolones and thio analogs such as 1H-2-oxo-3-(2-benzimidazolyl)-4-hyrdoxyquinoline. Ukrainets, I. et al., Khimiya Geterotsiklicheskikh Soedinii, 1, 105-108 (1993); Ukrainets, I. et al., Khimiya Geterotsiklicheskikh Soedinii, 8, 1105-1108 (1993); Ukrainets, I. et al., Chem. Heterocyclic Comp. 33, 600-604, (1997).

The synthesis of various quinoline derivatives is disclosed in WO 97/48694. These compounds are disclosed as capable of binding to nuclear hormone receptors and being useful for stimulating osteoblast proliferation and bone growth. The compounds are also disclosed as being useful in the treatment or prevention of diseases associated with nuclear hormone receptor families.

Various quinoline derivatives in which the benzene ring of the quinolone is substituted with a sulfur group are disclosed in WO 92/18483. These compounds are disclosed as being useful in pharmaceutical formulations and as medicaments.

Quinolone and coumarin derivatives have been disclosed as having use in a variety of applications unrelated to medicine and pharmaceutical formulations. References that describe the preparation of quinolone derivatives for use in photopolymerizable compositions or for luminescent properties include: U.S. Pat. No. 5,801,212 issued to Okamoto et al.; JP 8-29973; JP 7-43896; JP 6-9952; JP 63-258903; EP 797376; and DE 23 63 459.

Despite the exploration of a variety of chemistries to provide VEGF-RTK-antagonist therapies, a continuing need exists for compounds that inhibit the proliferation of capillaries, inhibit the growth of tumors, and/or inhibit vascular endothelial growth factor receptor tyrosine kinase and pharmaceutical formulations that contain such compounds. A need also exists for methods for administering such compounds and pharmaceutical formulations to patients in need thereof.

SUMMARY OF THE INVENTION

The present invention provides compounds, pharmaceutical formulations including the compounds, methods of preparing the pharmaceutical formulations, and methods of treating patients with the pharmaceutical formulations and compounds.

The present invention provides a first group of compounds having the structure I. The invention also provides tautomers of the compounds, pharmaceutically acceptable salts of the compounds, and pharmaceutically acceptable salts of the tautomers. Structure I has the following formula:

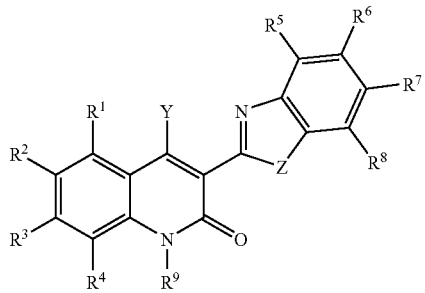

I where, in the first group of compounds:

Y is selected from —$OR^{10}$ groups, —C(=O)—$R^{11}$ groups, —$NR^{12}R^{13}$ groups, substituted or unsubstituted alkynyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted saturated heterocyclyl groups, substituted or unsubstituted heterocyclyloxyalkyl groups, substituted or unsubstituted hydroxyalkyl groups, or substituted or unsubstituted aryloxyalkyl groups;

Z is selected from O, S, or $NR^{14}$ groups;

$R^1$, $R^2$, $R^3$, and $R^4$ may be the same or different and are independently selected from H, Cl, Br, F, I, —CN, —$NO_2$, —OH, —$OR^{15}$ groups, —$NR^{16}R^{17}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, or —C(=O)$R^{18}$ groups;

$R^5$, $R^6$, $R^7$, and $R^8$ may be the same or different and are independently selected from H, Cl, Br, F, I, —$NO_2$, —OH, —$OR^{19}$ groups, —$NR^{20}R^{21}$ groups, —SH, —$SR^{22}$ groups, —S(=O)$R^{23}$ groups, —S(=O)$_2R^{24}$ groups, —CN, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted heterocyclylalkyl groups, —C(=O)$R^{25}$ groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^9$ and $R^{14}$ may be the same or different and are independently selected from H, —OH, substituted or unsubstituted alkoxy groups, substituted or unsubstituted aryloxy groups, —$NH_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{10}$ is selected from substituted or unsubstituted aryl groups, substituted or unsubstituted heterocyclyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —NH(heterocyclyl) groups, —N(heterocyclyl)$_2$ groups, —N(alkyl)(heterocyclyl) groups, —N(aryl)(heterocyclyl), —C(=O)NH(heterocyclyl) groups, —C(=O)N(heterocyclyl)$_2$ groups, —C(=O)N(alkyl)(heterocyclyl) groups, —C(=O)N(aryl)(heterocyclyl) groups, or substituted or unsubstituted heterocyclylalkyl groups;

$R^{11}$ is selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)$_2$ groups, —N(alkyl)(heterocyclyl) groups, —N(aryl)(heterocyclyl) groups, —O-alkyl groups, O-aryl groups, heterocyclyloxyalkyl groups, or substituted or unsubstituted aryl groups;

$R^{12}$ is selected from H, substituted or unsubstituted alkyl groups, substituted or unsubstituted aryl groups, or substituted or unsubstituted heterocyclyl groups;

$R^{13}$ is selected from substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, substituted or unsubstituted heterocyclyloxyalkyl groups, or —C(=O)—N(alkyl)(heterocyclyl) groups;

$R^{15}$ and $R^{19}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH(heterocyclyl) groups, —N(heterocyclyl)$_2$ groups, —N(alkyl)(heterocyclyl) groups, —N(aryl)(heterocyclyl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl, substituted or unsubstituted diheterocyclylaminoalkyl, substituted or unsubstituted (heterocyclyl)(alkyl)aminoalkyl, substituted or unsubstituted (heterocyclyl)(aryl)aminoalkyl, substituted or unsubstituted alkoxyalkyl groups, substituted or unsubstituted hydroxyalkyl groups, substituted or unsubstituted aryloxyalkyl groups, or substituted or unsubstituted heterocyclyloxyalkyl groups;

$R^{16}$ and $R^{20}$ may be the same or different and are independently selected from H, substituted or unsubstituted alkyl groups, substituted or unsubstituted aryl groups, or substituted or unsubstituted heterocyclyl groups;

$R^{17}$ and $R^{21}$ may be the same or different and are independently selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(aryl)(heterocyclyl) groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, substituted or unsubstituted heterocyclyloxyalkyl groups, or —C(=O)—N(alkyl)(heterocyclyl) groups;

$R^{18}$, $R^{23}$, $R^{24}$, and $R^{25}$ may be the same or different and are independently selected from H, —NH$_2$, —NH(alkyl) groups, —NH(aryl) groups, —N(alkyl)$_2$ groups, —N(aryl)$_2$ groups, -N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted heterocyclyl groups, substituted or unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups; and $R^{22}$ is selected from substituted or unsubstituted alkyl groups, substituted or unsubstituted aryl groups, or substituted or unsubstituted heterocyclyl groups.

The invention provides a second group of compounds including compounds having the structure I, tautomers of the compounds, pharmaceutically acceptable salts of the compounds, and pharmaceutically acceptable salts of the tautomers.

In the second group of compounds:

Y is selected from —$OR^{10}$ groups, —C(=O)—$R^{11}$ groups, —$NR^{12}R^{13}$ groups, substituted or unsubstituted alkynyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted saturated heterocyclyl groups, substituted or unsubstituted heterocyclyloxyalkyl groups, substituted or unsubstituted hydroxyalkyl groups, or substituted or unsubstituted aryloxyalkyl groups;

Z is selected from O, S, or $NR^{14}$ groups;

$R^1$, $R^2$, $R^3$, and $R^4$ may be the same or different and are independently selected from H, Cl, Br, F, I, —CN, —$NO_2$, —OH, —$OR^{15}$ groups, —$NR^{16}R^{17}$ groups, substituted or unsubstituted amidinyl groups, substituted or unsubstituted guanidinyl groups, substituted or unsubstituted primary, secondary, and tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, or —C(=O)$R^{18}$ groups;

$R^5$, $R^6$, $R^7$, and $R^8$ may be the same or different and are independently selected from H, Cl, Br, F, I, —$NO_2$, —OH, —$OR^{19}$ groups, —$NR^{20}R^{21}$ groups, —SH, —$SR^{22}$ groups, —S(=O)$R^{23}$ groups, —S(=O)$_2R^{24}$ groups, —CN, substituted or unsubstituted amidinyl groups, substituted or unsubstituted guanidinyl groups, substituted or unsubstituted primary, secondary, and tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted heterocyclylalkyl groups, —C(=O)$R^{25}$ groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^9$ is selected from the group consisting of —OH, substituted or unsubstituted alkoxy groups, substituted or unsubstituted aryloxy groups, —$NH_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{10}$ is selected from substituted or unsubstituted aryl groups, substituted or unsubstituted heterocyclyl groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —$NH_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, —C(=O)N(aryl)(heterocyclyl) groups, or substituted or unsubstituted heterocyclylalkyl groups;

$R^{11}$ is selected from H, —$NH_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)$_2$ groups, —N(alkyl)(heterocyclyl) groups, —O-alkyl groups, O-aryl groups, substituted or unsubstituted alkyl groups, or substituted or unsubstituted aryl groups;

$R^{12}$ is selected from H, substituted or unsubstituted alkyl groups, substituted or unsubstituted aryl groups, or substituted or unsubstituted heterocyclyl groups;

$R^{13}$ is selected from H, substituted or unsubstituted alkyl groups, substituted or unsubstituted aryl groups, substituted or unsubstituted heterocyclyl groups, —OH, alkoxy groups, aryloxy groups, —$NH_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(aryl)(heterocyclyl) groups, —C(=O)—N(alkyl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{14}$ is selected from H, —OH, substituted or unsubstituted alkoxy groups, substituted or unsubstituted aryloxy groups, —$NH_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{15}$ and $R^{19}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl, substituted or unsubstituted diheterocyclylaminoalkyl, substituted or unsubstituted (heterocyclyl)(alkyl)aminoalkyl, substituted or unsubstituted (heterocyclyl)(aryl)aminoalkyl, substituted or unsubstituted alkoxyalkyl groups, substituted or unsubstituted hydroxyalkyl groups, substituted or unsubstituted aryloxyalkyl groups, or substituted or unsubstituted heterocyclyloxyalkyl groups;

$R^{16}$ and $R^{20}$ may be the same or different and are independently selected from H, substituted or unsubstituted alkyl groups, substituted or unsubstituted aryl groups, or substituted or unsubstituted heterocyclyl groups;

$R^{17}$ and $R^{21}$ may be the same or different and are independently selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(aryl)(heterocyclyl) groups, —C(=O)—N(alkyl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{18}$, $R^{23}$, $R^{24}$, and $R^{25}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted heterocyclyl groups, substituted or unsubstituted aryloxy groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups; and $R^{22}$ is selected from substituted or unsubstituted alkyl groups, substituted or unsubstituted aryl groups, or substituted or unsubstituted heterocyclyl groups.

The invention provides a third group of compounds including compounds having the structure I, tautomers of the compounds, pharmaceutically acceptable salts of the compounds, and pharmaceutically acceptable salts of the tautomers.

In the third group of compounds:

Y is selected from —OH, SH, alkylthio groups, arylthio groups, —OR$^{10}$ groups, —C(=O)—R$^{11}$ groups, —NR$^{12}$R$^{13}$ groups, —CN, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted heterocyclyl groups, substituted or unsubstituted aryl groups, substituted or unsubstituted heterocyclyloxyalkyl groups, substituted or unsubstituted hydroxyalkyl groups, substituted or unsubstituted alkoxyalkyl groups, or substituted or unsubstituted aryloxyalkyl groups;

Z is selected from O, S, or NR$^{14}$ groups;

$R^1$, $R^2$, $R^3$, and $R^4$ may be the same or different and are independently selected from H, Cl, Br, F, I, —CN, —NO$_2$, —OH, —OR$^{15}$ groups, —NR$^{16}$R$^{17}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, or —C(=O)R$^{18}$ groups;

$R^5$, $R^6$, $R^7$, and $R^8$ may be the same or different and are independently selected from H, Cl, Br, F, I, —NO$_2$, —OH, —OR$^{19}$ groups, —NR$^{20}$R$^{21}$ groups, —SH, —SR$^{22}$ groups, —S(=O)R$^{23}$ groups, —S(=O)$_2$R$^{24}$ groups, —CN, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, —C(=O)R$^{25}$ groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^9$ and $R^{14}$ may be the same or different and are independently selected from H, —OH, substituted or unsubstituted alkoxy groups, substituted or unsubstituted aryloxy groups, —NH$_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N (alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

$R^{11}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, —NH(heterocyclyl) groups, —N(heterocyclyl)$_2$ groups, —N(alkyl)(heterocyclyl) groups, or substituted or unsubstituted aryl groups;

$R^{12}$ is selected from H, substituted or unsubstituted alkyl groups, substituted or unsubstituted aryl groups, or substituted or unsubstituted heterocyclyl groups;

$R^{13}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)N(heterocyclyl)$_2$ groups, —C(=O)N(alkyl)(heterocyclyl) groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{15}$ and $R^{19}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl, substituted or unsubstituted diheterocyclylaminoalkyl, substituted or unsubstituted (heterocyclyl)(alkyl)aminoalkyl, substituted or unsubstituted (heterocyclyl)(aryl)aminoalkyl, substituted or unsubstituted alkoxyalkyl groups, substituted or unsubstituted hydroxyalkyl groups, substituted or unsubstituted aryloxyalkyl groups, or substituted or unsubstituted heterocyclyloxyalkyl groups;

$R^{16}$ and $R^{20}$ may be the same or different and are independently selected from H, substituted or unsubstituted alkyl groups, substituted or unsubstituted aryl groups, or substituted or unsubstituted heterocyclyl groups;

$R^{17}$ and $R^{21}$ may be the same or different and are independently selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(alkyl)(heterocyclyl) groups, —C(=O)—N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{18}$, $R^{23}$, $R^{24}$, and $R^{25}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted aryloxy groups, substituted or unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups; and $R^{22}$ is selected from substituted or unsubstituted alkyl groups, substituted or unsubstituted aryl groups, or substituted or unsubstituted heterocyclyl groups.

In the third group of compounds, at least one of $R^5$, $R^6$, $R^7$, or $R^8$ is selected from substituted or unsubstituted amidinyl groups, substituted or unsubstituted guanidinyl groups, substituted or unsubstituted saturated heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups; —OR$^{19}$ groups where $R^{19}$ is selected from substituted or unsubstituted aryl groups, substituted or unsubstituted heterocyclyl groups, substituted or unsubstituted heterocyclylalkyl groups, —C(=O)H, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted and unsubstituted heterocyclyloxyalkyl groups; —$NR^{20}R^{21}$ groups where $R^{20}$ is selected from substituted or unsubstituted heterocyclyl groups; —$NR^{20}R^{21}$ groups where $R^{21}$ is selected from substituted or unsubstituted heterocyclyl groups, —C(=O)H, —C(=O)-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, substituted or unsubstituted heterocyclylalkyl groups, or substituted or unsubstituted heterocyclyloxyalkyl groups; or —C(=O)$R^{25}$ groups where $R^{25}$ is selected from H, —$NH_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted aryl groups, substituted or unsubstituted aryloxy groups, or substituted or unsubstituted heterocyclyl groups.

The invention provides a fourth group of compounds having the structure I, tautomers of the compounds, pharmaceutically acceptable salts of the compounds, and pharmaceutically acceptable salts of the tautomers.

In the fourth group of compounds:

Y is selected from —OH, SH, alkylthio groups, arylthio groups, —$OR^{10}$ groups, —C(=O)—$R^{11}$ groups, —$NR^{12}R^{13}$ groups, —CN, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted heterocyclyl groups, substituted or unsubstituted aryl groups, substituted or unsubstituted heterocyclyloxyalkyl groups, substituted or unsubstituted hydroxyalkyl groups, substituted or unsubstituted alkoxyalkyl groups, or substituted or unsubstituted aryloxyalkyl groups;

Z is selected from O, S, or $NR^{14}$ groups;

$R^1$, $R^2$, $R^3$, and $R^4$ may be the same or different and are independently selected from H, Cl, Br, F, I, —CN, —$NO_2$, —OH, —$OR^{15}$ groups, —$NR^{16}R^{17}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, or —C(=O)$R^{18}$ groups;

$R^5$, $R^6$, $R^7$, and $R^8$ may be the same or different and are independently selected from H, Cl, Br, F, I, —$NO_2$, —OH, —$OR^{19}$ groups, —$NR^{20}R^{21}$ groups, —SH, —$SR^{22}$ groups, —S(=O)$R^{23}$ groups, —S(=O)$_2R^{24}$ groups, —CN, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, —C(=O)$R^{25}$ groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^9$ and $R^{14}$ may be the same or different and are independently selected from H, —OH, substituted or unsubstituted alkoxy groups, substituted or unsubstituted aryloxy groups, —$NH_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —$NH_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

$R^{11}$ is selected from H, —OH, alkoxy groups, aryloxy groups, —$NH_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, —NH(heterocyclyl) groups, —N(heterocyclyl)$_2$ groups, —N(alkyl)(heterocyclyl) groups, or substituted or unsubstituted aryl groups;

$R^{12}$ is selected from H, substituted or unsubstituted alkyl groups, substituted or unsubstituted aryl groups, or substituted or unsubstituted heterocyclyl groups;

$R^{13}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)N(heterocyclyl)$_2$ groups, —C(=O)N(alkyl)(heterocyclyl) groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{15}$ and $R^{19}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl, substituted or unsubstituted diheterocyclylaminoalkyl, substituted or unsubstituted (heterocyclyl)(alkyl)aminoalkyl, substituted or unsubstituted (heterocyclyl)(aryl)aminoalkyl, substituted or unsubstituted alkoxyalkyl groups, substituted or unsubstituted hydroxyalkyl groups, substituted or unsubstituted aryloxyalkyl groups, or substituted or unsubstituted heterocyclyloxyalkyl groups;

$R^{16}$ and $R^{20}$ may be the same or different and are independently selected from H, substituted or unsubstituted alkyl groups, substituted or unsubstituted aryl groups, or substituted or unsubstituted heterocyclyl groups;

$R^{17}$ and $R^{21}$ may be the same or different and are independently selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups,—C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{18}$, $R^{23}$, $R^{24}$, and $R^{25}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted aryloxy groups, substituted or unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups; and $R^{22}$ is selected from substituted or unsubstituted alkyl groups, substituted or unsubstituted aryl groups, or substituted or unsubstituted heterocyclyl groups.

In the fourth group of compounds, at least one of $R^1$, $R^2$, $R^3$, or $R^4$ is an —OR$^{15}$ group and $R^{15}$ is selected from substituted or unsubstituted heterocyclylalkyl groups, substituted or unsubstituted dialkylaminoalkyl groups, substituted or unsubstituted alkylaminoalkyl groups, substituted or unsubstituted aminoalkyl groups, substituted or unsubstituted diarylaminoalkyl groups, substituted or unsubstituted arylaminoalkyl groups, substituted or unsubstituted (alkyl)(aryl)aminoalkyl groups, substituted or unsubstituted heterocyclyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, or substituted or unsubstituted (heterocyclyl)(aryl)aminoalkyl groups.

Preferred compounds in any of the first, second, or third groups described above are provided in which Z is an —NR$^4$. Preferred compound of the fourth group are also provided in which Z is an —NR$^{10}$ group.

Preferred compounds according to the first, second, third, and fourth groups of compounds are provided in which Y is an —OR$^{10}$ group, an —NR$^{12}$R$^{13}$ group, or a substituted or unsubstituted alkynyl group.

Other preferred compounds of the first, second, third, and fourth groups are provided in which $R^1$ is selected from H, substituted or unsubstituted alkoxy groups, substituted or unsubstituted heterocyclylalkoxy groups, substituted or unsubstituted heterocyclyloxy groups, or substituted or unsubstituted heterocyclyl groups.

Still further provided are compounds of the first, second, third, and fourth groups in which $R^2$ is selected from the group consisting of H, F, Cl, —NO$_2$, substituted and unsubstituted heterocyclylalkoxy groups, and substituted and unsubstituted heterocyclyl groups.

Still further provided are compounds of the first, second, third, and fourth groups in which $R^6$ or $R^7$ is an alkyl group. Still further preferred compounds of the four groups are those in which $R^6$ or $R^7$ is an —OR$^{19}$ group and $R^{19}$ is an alkyl group, an aryl group, a heterocyclyl group, or a heterocyclylalkyl group.

Preferred compounds of the fourth group of compounds are provided in which $R^1$ is an —$OR^{15}$ group and $R^{15}$ is selected from substituted or unsubstituted heterocyclylalkyl groups, substituted or unsubstituted dialkylaminoalkyl groups, substituted or unsubstituted alkylaminoalkyl groups, substituted or unsubstituted aminoalkyl groups, substituted or unsubstituted diarylaminoalkyl groups, substituted or unsubstituted arylaminoalkyl groups, substituted or unsubstituted (alkyl)(aryl)aminoalkyl groups, substituted or unsubstituted heterocyclyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, or substituted or unsubstituted (heterocyclyl)(aryl)aminoalkyl groups.

The invention further provides compounds having the structure II. The invention provides tautomers of the compounds, pharmaceutically acceptable salts of the compounds, and pharmaceutically acceptable salts of the tautomers. Structure II has the following formula

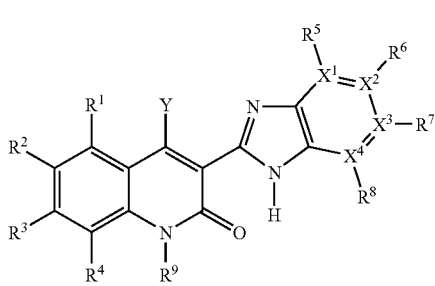

where:

Y is selected from H, —OH, —$OR^{10}$ groups, —SH, —$SR^{11}$ groups, —$NR^{12}R^{13}$ groups, —CN, —C(=O)—$R^{14}$ groups, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted heterocyclyl groups, substituted or unsubstituted aryl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$X^1$, $X^2$, $X^3$, and $X^4$ are selected from C or N, and at least one of $X^1$, $X^2$, $X^3$, and $X^4$ is N;

$R^1$, $R^2$, $R^3$, $R^4$, $R^5$, $R^6$, $R^7$, and $R^8$ may be the same or different and are independently selected from H, Cl, Br, F, I, —$NO_2$, —CN, —OH, —$OR^{15}$ groups, —$NR^{16}R^{17}$ groups, —C(=O)$R^{18}$ groups, —SH, —$SR^{19}$ groups, —S(=O)$R^{20}$ groups, $S(=O)_2R^{21}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups; $R^5$ is absent or is H if $X^1$ is N; $R^6$ is absent or is H if $X^2$ is N; $R^7$ is absent or is H if $X^3$ is N; and $R^8$ is absent or is H if $X^4$ is N;

$R^9$ is selected from H, —OH, substituted or unsubstituted alkoxy groups, substituted or unsubstituted aryloxy groups, —$NH_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —$NH_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

$R^{11}$ and $R^{19}$ may be the same or different and are independently selected from substituted or unsubstituted alkyl groups, or substituted or unsubstituted aryl groups;

$R^{12}$ is selected from H, substituted or unsubstituted alkyl groups, substituted or unsubstituted aryl groups, or substituted or unsubstituted heterocyclyl groups;

$R^{13}$ is selected from H, substituted or unsubstituted alkyl groups, substituted or unsubstituted aryl groups, substituted or unsubstituted heterocyclyl groups, —OH, alkoxy groups, aryloxy groups, —$NH_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)N(heterocyclyl)$_2$ groups, —C(=O)N(alkyl)(heterocyclyl) groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{14}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —NH(heterocyclyl) groups, —N(heterocyclyl)$_2$ groups, —N(alkyl)(heterocyclyl) groups, or —N(aryl)(heterocyclyl) groups;

$R^{12}$ and $R^{13}$ may join together to form a 5 to 7 membered saturated or unsaturated, substituted or unsubstituted N-containing ring;

$R^{15}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted alkoxyalkyl groups, substituted or unsubstituted aryloxyalkyl groups, substituted or unsubstituted hydroxyalkyl groups, or substituted or unsubstituted heterocyclyloxyalkyl groups;

$R^{16}$ is selected from H, substituted or unsubstituted alkyl groups, substituted or unsubstituted aryl groups, or substituted or unsubstituted heterocyclyl groups;

$R^{17}$ is selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (aryl)(alkyl)aminoalkyl groups, substituted or unsubstituted heterocyclylalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, substituted or unsubstituted heterocyclyloxyalkyl groups, —OH, substituted or unsubstituted alkoxy groups, substituted or unsubstituted aryloxy groups, or —NH$_2$ groups;

$R^{16}$ and $R^{17}$ may join together to form a 5 to 7 membered saturated or unsaturated, substituted or unsubstituted N-containing ring; and $R^{18}$, $R^{20}$, and $R^{21}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —OH, substituted or unsubstituted alkoxy groups, substituted or unsubstituted aryloxy groups, substituted or unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups.

Preferred compounds having structure II are also provided where Y is selected from H, —OH, —OR$^{10}$ groups, or —NR$^{12}$R$^{13}$ groups.

Still other preferred compounds having structure II are provided where at least two of $X^1$, $X^2$, $X^3$, and $X^4$ are C and the corresponding substituents $R^5$, $R^6$, $R^7$, and $R^8$ are hydrogen, and at least one of $X^1$, $X^2$, $X^3$, and $X^4$ is N, and the rest of the compound is consistent with any of the above-described compounds.

Still other more preferred compounds of structure II are provided in which $R^6$ or $R^7$ is an alkyl group and the rest of the compound is consistent with any of the above-described compounds.

Still other compounds of structure II are provided in which $R^5$ or $R^7$ is an —OR$^{15}$ group and $R^{15}$ is an alkyl, aryl, heterocyclyl, or heterocyclylalkyl group and the rest of the molecule is consistent with any of the above-described compounds.

Still further compounds having the formula of structure II are provided in which $R^1$ is selected from H, substituted or unsubstituted alkoxy groups, substituted or unsubstituted heterocyclylalkoxy groups, substituted or unsubstituted heterocyclyloxy groups, or substituted or unsubstituted heterocyclyl groups.

Still other compounds having the Structure II are provided in which In other compounds having the structure II, $R^2$ is selected from H, F, Cl, —NO$_2$, substituted or unsubstituted heterocyclyl groups, or substituted or unsubstituted heterocyclylalkoxy groups.

Pharmaceutical formulations according to the present invention are provided which include any of the compounds described above in combination with a pharmaceutically acceptable carrier.

A method of treating a patient in need of an inhibitor of vascular endothelial growth factor receptor tyrosine kinase is provided which includes administering an effective amount of the pharmaceutical formulation according to the present invention to a patient in need thereof.

Further objects, features and advantages of the invention will be apparent from the following detailed description.

DETAILED DESCRIPTION OF THE INVENTION

The present invention provides novel compounds that act as antagonists of receptor tyrosine kinases, and, more particularly, as inhibitors of bFGF and/or VEGF-RTK function. The compounds provided herein can be formulated into pharmaceutical formulations that are useful in treating patients with a need for an inhibitor of VEGF-RTK, especially, in particular embodiments, to provide compositions and methods for reducing capillary proliferation and in the treatment of cancer.

The following abbreviations and definitions are used throughout this application:

"VEGF" is an abbreviation that stands for vascular endothelial growth factor.

"RTK" is an abbreviation that stands for receptor tyrosine kinase.

"VEGF-RTK" is an abbreviation that stands for vascular endothelial growth factor receptor tyrosine kinase.

"Flt-1" is an abbreviation that stands for fms-like tyrosine kinase-1, also known as vascular endothelial growth factor receptor-1 or "VEGFR1".

"KDR" is an abbreviation that stands for kinase-insert domain-containing receptor, also known as vascular endothelial growth factor receptor-2 or "VEGFR2".

"bFGF" is an abbreviation that stands for basic fibroblast growth factor.

"bFGFR" is an abbreviation that stands for basic fibroblast growth factor receptor.

Generally, reference to a certain element such as hydrogen or H is meant to include all isotopes of that element. For example, if an R group is defined to include hydrogen or H, it also includes deuterium and tritium.

The phrase "unsubstituted alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH($CH_3$)$_2$, —CH($CH_3$)($CH_2CH_3$), —CH($CH_2CH_3$)$_2$, —C($CH_3$)$_3$, —C($CH_2CH_3$)$_3$, —$CH_2CH$($CH_3$)$_2$, —$CH_2CH$($CH_3$)($CH_2CH_3$), —$CH_2CH$($CH_2CH_3$)$_2$, —$CH_2C$($CH_3$)$_3$, —$CH_2C$($CH_2CH_3$)$_3$, —CH($CH_3$)CH($CH_3$)($CH_2CH_3$), —$CH_2CH_2CH$($CH_3$)$_2$, —$CH_2CH_2CH$($CH_3$)($CH_2CH_3$), —$CH_2CH_2CH$($CH_2CH_3$)$_2$, —$CH_2CH_2C$($CH_3$)$_3$, —$CH_2CH_2C$($CH_2CH_3$)$_3$, —CH($CH_3$)$CH_2CH$($CH_3$)$_2$, —CH($CH_3$)CH($CH_3$)CH($CH_3$)$_2$, —CH($CH_2CH_3$)CH($CH_3$)CH($CH_3$)($CH_2CH_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Preferred unsubstituted alkyl groups include straight and branched chain alkyl groups and cyclic alkyl groups having 1 to 20 carbon atoms. More preferred such unsubstituted alkyl groups have from 1 to 10 carbon atoms while even more preferred such groups have from 1 to 5 carbon atoms. Most preferred unsubstituted alkyl groups include straight and branched chain alkyl groups having from 1 to 3 carbon atoms and include methyl, ethyl, propyl, and —CH($CH_3$)$_2$.

The phrase "substituted alkyl" refers to an unsubstituted alkyl group as defined above in which one or more bonds to a carbon(s) or hydrogen(s) are replaced by a bond to non-hydrogen and non-carbon atoms such as, but not limited to, a halogen atom in halides such as F, Cl, Br, and I; and oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Preferred substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted aryl" refers to aryl groups that do not contain heteroatoms. Thus the phrase includes, but is not limited to, groups such as phenyl, biphenyl, anthracenyl, naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH═C(H)($CH_3$), —CH═C($CH_3$)$_2$, —C($CH_3$)═C(H)$_2$, —C($CH_3$)═C(H)($CH_3$), —C($CH_2CH_3$)═$CH_2$, cyclohexenyl, cyclopentenyl, cyclohexadienyl, butadienyl, pentadienyl, and hexadienyl among others.

The phrase "substituted alkenyl" has the same meaning with respect to unsubstituted alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "unsubstituted alkynyl" refers to straight and branched chain groups such as those described with respect to unsubstituted alkyl groups as defined above, except that at least one triple bond exists between two carbon atoms.

Examples include, but are not limited to —C≡C(H), —C≡C(CH₃), —C≡C(CH₂CH₃), —C(H₂)C≡C(H), —C(H)₂C≡C(CH₃), and —C(H)₂C≡C(CH₂CH₃) among others.

The phrase "substituted alkynyl" has the same meaning with respect to unsubstituted alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl (—CH₃) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group). Thus the phrase includes, but is not limited to, groups such as benzyl, diphenylmethyl, and 1-phenylethyl (—CH(C₆H₅)(CH₃)) among others.

The phrase "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom. Examples of substituted aralkyl groups include, but are not limited to, —CH₂C(=O)(C₆H₅), and —CH₂(2-methylphenyl) among others.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an unsubstituted heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—CH₃) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups had with respect to unsubstituted aralkyl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

The phrase "unsubstituted alkylaminoalkyl" refers to an unsubstituted alkyl group as defined above in which a carbon or hydrogen bond is replaced by a bond to a nitrogen atom that is bonded to a hydrogen atom and an unsubstituted alkyl group as defined above. For example, methyl (—$CH_3$) is an unsubstituted alkyl group. If a hydrogen atom of the methyl group is replaced by a bond to a nitrogen atom that is bonded to a hydrogen atom and an ethyl group, then the resulting compound is —$CH_2$—N(H)($CH_2CH_3$) which is an unsubstituted alkylaminoalkyl group.

The phrase "substituted alkylaminoalkyl" refers to an unsubstituted alkylaminoalkyl group as defined above except where one or more bonds to a carbon or hydrogen atom in one or both of the alkyl groups is replaced by a bond to a non-carbon or non-hydrogen atom as described above with respect to substituted alkyl groups except that the bond to the nitrogen atom in all alkylaminoalkyl groups does not by itself qualify all alkylaminoalkyl groups as being substituted. However, substituted alkylaminoalkyl groups does include groups in which the hydrogen bonded to the nitrogen atom of the group is replaced with a non-carbon and non-hydrogen atom.

The phrase "unsubstituted dialkylaminoalkyl" refers to an unsubstituted alkyl group as defined above in which a carbon bond or hydrogen bond is replaced by a bond to a nitrogen atom which is bonded to two other similar or different unsubstituted alkyl groups as defined above.

The phrase "substituted dialkylaminoalkyl" refers to an unsubstituted dialkylaminoalkyl group as defined above in which one or more bonds to a carbon or hydrogen atom in one or more of the alkyl groups is replaced by a bond to a non-carbon and non-hydrogen atom as described with respect to substituted alkyl groups. The bond to the nitrogen atom in all dialkylaminoalkyl groups does not by itself qualify all dialkylaminoalkyl groups as being substituted.

The phrase "unsubstituted heterocyclyloxyalkyl" refers to an unsubstituted alkyl group as defined above in which a carbon bond or hydrogen bond is replaced by a bond to an oxygen atom which is bonded to an unsubstituted heterocyclyl group as defined above.

The phrase "substituted heterocyclyloxyalkyl" refers to an unsubstituted heterocyclyloxyalkyl group as defined above in which a bond to a carbon or hydrogen group of the alkyl group of the heterocyclyloxyalkyl group is bonded to a non-carbon and non-hydrogen atom as described above with respect to substituted alkyl groups or in which the heterocyclyl group of the heterocyclyloxyalkyl group is a substituted heterocyclyl group as defined above.

The phrase "unsubstituted arylaminoalkyl" refers to an unsubstituted alkyl group as defined above in which a carbon bond or hydrogen bond is replaced by a bond to a nitrogen atom which is bonded to at least one unsubstituted aryl group as defined above.

The phrase "substituted arylaminoalkyl" refers to an unsubstituted arylaminoalkyl group as defined above except where either the alkyl group of the arylaminoalkyl group is a substituted alkyl group as defined above or the aryl group of the arylaminoalkyl group is a substituted aryl group except that the bonds to the nitrogen atom in all arylaminoalkyl groups does not by itself qualify all arylaminoalkyl groups as being substituted. However, substituted arylaminoalkyl groups does include groups in which the hydrogen bonded to the nitrogen atom of the group is replaced with a non-carbon and non-hydrogen atom.

The phrase "unsubstituted heterocyclylaminoalkyl" refers to an unsubstituted alkyl group as defined above in which a carbon or hydrogen bond is replaced by a bond to a nitrogen atom which is bonded to at least one unsubstituted heterocyclyl group as defined above.

The phrase "substituted heterocyclylaminoalkyl" refers to unsubstituted heterocyclylaminoalkyl groups as defined above in which the heterocyclyl group is a substituted heterocyclyl group as defined above and/or the alkyl group is a substituted alkyl group as defined above. The bonds to the nitrogen atom in all heterocyclylaminoalkyl groups does not by itself qualify all heterocyclylaminoalkyl groups as being substituted. However, substituted heterocyclylaminoalkyl groups do include groups in which the hydrogen bonded to the nitrogen atom of the group is replaced with a non-carbon and non-hydrogen atom.

The phrase "unsubstituted alkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to a hydrogen atom and an unsubstituted alkyl group as defined above.

The phrase "substituted alkylaminoalkoxy" refers to unsubstituted alkylaminoalkoxy groups as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if the hydrogen bonded to the amino group is bonded to a non-carbon and non-hydrogen atom and/or if the alkyl group bonded to the nitrogen of the amine is bonded to a non-carbon and non-hydrogen atom as described above with respect to substituted alkyl groups. The presence of the amine and alkoxy functionality in all alkylaminoalkoxy groups does not by itself qualify all such groups as substituted alkylaminoalkoxy groups.

The phrase "unsubstituted dialkylaminoalkoxy" refers to an unsubstituted alkyl group as defined above in which a carbon or hydrogen bond is replaced by a bond to an oxygen atom which is bonded to the parent compound and in which another carbon or hydrogen bond of the unsubstituted alkyl group is bonded to a nitrogen atom which is bonded to two other similar or different unsubstituted alkyl groups as defined above.

The phrase "substituted dialkylaminoalkoxy" refers to an unsubstituted dialkylaminoalkoxy group as defined above in which a bond to a carbon or hydrogen atom of the alkyl group bonded to the oxygen atom which is bonded to the parent compound is replaced by one or more bonds to a non-carbon and non-hydrogen atoms as discussed above with respect to substituted alkyl groups and/or if one or more of the alkyl groups bonded to the nitrogen of the amine is bonded to a non-carbon and non-hydrogen atom as described above with respect to substituted alkyl groups. The presence of the amine and alkoxy functionality in all dialkylaminoalkoxy groups does not by itself qualify all such groups as substituted dialkylaminoalkoxy groups.

The phrase "unsubstituted heterocyclyloxy" refers to a hydroxyl group (—OH) in which the bond to the hydrogen atom is replaced by a bond to a ring atom of an otherwise unsubstituted heterocyclyl group as defined above.

The phrase "substituted heterocyclyloxy" refers to a hydroxyl group (—OH) in which the bond to the hydrogen atom is replaced by a bond to a ring atom of an otherwise substituted heterocyclyl group as defined above.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethyichlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

Generally, the invention provides compounds including having the structure I. The invention also provides tautomers of the compounds, pharmaceutically acceptable salts of the compounds, and pharmaceutically acceptable salts of the tautomers. Structure I has the following formula:

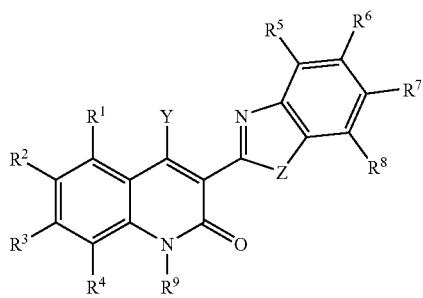

I

Preferred compounds having structure I are those within one of four groups.

In the first group of compounds:

Y is selected from $-OR^{10}$ groups, $-C(=O)-R^{11}$ groups, $-NR^{12}R^{13}$ groups, substituted or unsubstituted alkynyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted saturated heterocyclyl groups, substituted or unsubstituted heterocyclyloxyalkyl groups, substituted or unsubstituted hydroxyalkyl groups, or substituted or unsubstituted aryloxyalkyl groups;

Z is selected from O, S, or $NR^{14}$ groups;

$R^1$, $R^2$, $R^3$, and $R^4$ may be the same or different and are independently selected from H, Cl, Br, F, I, —CN, —$NO_2$, —OH, —$OR^{15}$ groups, —$NR^{16}R^{17}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, or —$C(=O)R^{18}$ groups;

$R^5$, $R^6$, $R^7$, and $R^8$ may be the same or different and are independently selected from H, Cl, Br, F, I, —$NO_2$, —OH, —$OR^{19}$ groups, —$NR^{20}R^{21}$ groups, —SH, —$SR^{22}$ groups, —$S(=O)R^{23}$ groups, —$S(=O)_2R^{24}$ groups, —CN, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted heterocyclylalkyl groups, —$C(=O)R^{25}$ groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^9$ and $R^{14}$ may be the same or different and are independently selected from H, —OH, substituted or unsubstituted alkoxy groups, substituted or unsubstituted aryloxy groups, —$NH_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{10}$ is selected from substituted or unsubstituted aryl groups, substituted or unsubstituted heterocyclyl groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH (aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —NH(heterocyclyl) groups, —N(heterocyclyl)$_2$ groups, —N(alkyl)(heterocyclyl) groups, —N(aryl)(heterocyclyl), —C(=O)NH(heterocyclyl) groups, —C(=O)N(heterocyclyl)$_2$ groups, —C(=O)N(alkyl)(heterocyclyl) groups, —C(=O)N(aryl)(heterocyclyl) groups, or substituted or unsubstituted heterocyclylalkyl groups;

$R^{11}$ is selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)$_2$ groups, —N(alkyl)(heterocyclyl) groups, —N(aryl)(heterocyclyl) groups, —O-alkyl groups, O-aryl groups, heterocyclyloxyalkyl groups, or substituted or unsubstituted aryl groups;

$R^{12}$ is selected from H, substituted or unsubstituted alkyl groups, substituted or unsubstituted aryl groups, or substituted or unsubstituted heterocyclyl groups;

$R^{13}$ is selected from substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, substituted or unsubstituted heterocyclyloxyalkyl groups, or —C(=O)—N(alkyl)(heterocyclyl) groups;

$R^{15}$ and $R^{19}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH(heterocyclyl) groups, —N(heterocyclyl)$_2$ groups, —N(alkyl)(heterocyclyl) groups, —N(aryl)(heterocyclyl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl, substituted or unsubstituted diheterocyclylaminoalkyl, substituted or unsubstituted (heterocyclyl)(alkyl)aminoalkyl, substituted or unsubstituted (heterocyclyl)(aryl)aminoalkyl, substituted or unsubstituted alkoxyalkyl groups, substituted or unsubstituted hydroxyalkyl groups, substituted or unsubstituted aryloxyalkyl groups, or substituted or unsubstituted heterocyclyloxyalkyl groups;

$R^{16}$ and $R^{20}$ may be the same or different and are independently selected from H, substituted or unsubstituted alkyl groups, substituted or unsubstituted aryl groups, or substituted or unsubstituted heterocyclyl groups;

$R^{17}$ and $R^{21}$ may be the same or different and are independently selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(aryl)(heterocyclyl) groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, substituted or unsubstituted heterocyclyloxyalkyl groups, or —C(=O)—N(alkyl)(heterocyclyl) groups;

$R^{18}$, $R^{23}$, $R^{24}$, and $R^{25}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted heterocyclyl groups, substituted or unsubstituted aryloxy groups, heterocyclyloxy groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups; and $R^{22}$ is selected from substituted or unsubstituted alkyl groups, substituted or unsubstituted aryl groups, or substituted or unsubstituted heterocyclyl groups.

In other embodiments of the invention, compounds of formula I above include a second group of compounds having the substituents described below:

Y is selected from —OR$^{10}$ groups, —C(=O)—R$^{11}$ groups, —NR$^{12}$R$^{13}$ groups, substituted or unsubstituted alkynyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted saturated heterocyclyl groups, substituted or unsubstituted heterocyclyloxyalkyl groups, substituted or unsubstituted hydroxyalkyl groups, or substituted or unsubstituted aryloxyalkyl groups;

Z is selected from O, S, or $NR^{14}$ groups;

$R^1$, $R^2$, $R^3$, and $R^4$ may be the same or different and are independently selected from H, Cl, Br, F, I, —CN, —NO₂, —OH, —$OR^{15}$ groups, —$NR^{16}R^{17}$ groups, substituted or unsubstituted amidinyl groups, substituted or unsubstituted guanidinyl groups, substituted or unsubstituted primary, secondary, and tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, or —C(=O)$R^{18}$ groups;

$R^5$, $R^6$, $R^7$, and $R^8$ may be the same or different and are independently selected from H, Cl, Br, F, I, —NO₂, —OH, —$OR^{19}$ groups, —$NR^{20}R^{21}$ groups, —SH, —$SR^{22}$ groups, —S(=O)$R^{23}$ groups, —S(=O)₂$R^{24}$ groups, —CN, substituted or unsubstituted amidinyl groups, substituted or unsubstituted guanidinyl groups, substituted or unsubstituted primary, secondary, and tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted heterocyclylalkyl groups, —C(=O)$R^{25}$ groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^9$ is selected from the group consisting of —OH, substituted or unsubstituted alkoxy groups, substituted or unsubstituted aryloxy groups, —NH₂, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{10}$ is selected from substituted or unsubstituted aryl groups, substituted or unsubstituted heterocyclyl groups, —C(=O)H, —C(=O)-alkyl groups, —C(=O)-aryl groups, —C(=O)O-alkyl groups, —C(=O)O-aryl groups, —C(=O)NH₂, —C(=O)NH(alkyl) groups, —C(=O)NH(aryl) groups, —C(=O)N(alkyl)₂ groups, —C(=O)N(aryl)₂ groups, —C(=O)N(alkyl)(aryl) groups, —NH₂, —NH(alkyl) groups, —NH(aryl) groups, —N(alkyl)₂ groups, —N(alkyl)(aryl) groups, —N(aryl)₂ groups, —C(=O)NH(heterocyclyl) groups, —C(=O)N(heterocyclyl)₂ groups, —C(=O) N(alkyl)(heterocyclyl) groups, —C(=O)N(aryl)(heterocyclyl) groups, or substituted or unsubstituted heterocyclylalkyl groups;

$R^{11}$ is selected from H, —NH₂, —NH(alkyl) groups, —NH(aryl) groups, —N(alkyl)₂ groups, —N(aryl)₂ groups, —N(alkyl)(aryl) groups, —NH(heterocyclyl) groups, —N(heterocyclyl)₂ groups, —N(alkyl)(heterocyclyl) groups, —O-alkyl groups, O-aryl groups, substituted or unsubstituted alkyl groups, or substituted or unsubstituted aryl groups;

$R^{12}$ is selected from H, substituted or unsubstituted alkyl groups, substituted or unsubstituted aryl groups, or substituted or unsubstituted heterocyclyl groups;

$R^{13}$ is selected from H, substituted or unsubstituted alkyl groups, substituted or unsubstituted aryl groups, substituted or unsubstituted heterocyclyl groups, —OH, alkoxy groups, aryloxy groups, —NH₂, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH₂, —C(=O)NH(alkyl) groups, —C(=O)NH(aryl) groups, —C(=O)N(alkyl)₂ groups, —C(=O)N(aryl)₂ groups, —C(=O)N(alkyl)(aryl) groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)N (heterocyclyl)₂ groups, —C(=O)N(aryl)(heterocyclyl) groups, —C(=O)N(alkyl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{14}$ is selected from H, —OH, substituted or unsubstituted alkoxy groups, substituted or unsubstituted aryloxy groups, —NH₂, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{15}$ and $R^{19}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH₂, —C(=O) NH(alkyl) groups, —C(=O)NH(aryl) groups, —C(=O)N (alkyl)₂ groups, —C(=O)N(aryl)₂ groups, —C(=O)N (alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl, substituted or unsubstituted diheterocyclylaminoalkyl, substituted or unsubstituted (heterocyclyl)(alkyl)aminoalkyl, substituted or unsubstituted (heterocyclyl)(aryl)aminoalkyl, substituted or unsubstituted alkoxyalkyl groups, substituted or unsubstituted hydroxyalkyl groups, substituted or unsubstituted aryloxyalkyl groups, or substituted or unsubstituted heterocyclyloxyalkyl groups;

$R^{16}$ and $R^{20}$ may be the same or different and are independently selected from H, substituted or unsubstituted alkyl groups, substituted or unsubstituted aryl groups, or substituted or unsubstituted heterocyclyl groups;

$R^{17}$ and $R^{21}$ may be the same or different and are independently selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups,—C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(aryl)(heterocyclyl) groups, —C(=O)—N(alkyl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{18}$, $R^{23}$, $R^{24}$, and $R^{25}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted heterocyclyl groups, substituted or unsubstituted aryloxy groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups; and $R^{22}$ is selected from substituted or unsubstituted alkyl groups, substituted or unsubstituted aryl groups, or substituted or unsubstituted heterocyclyl groups.

In another embodiment, the present invention provides a third group of compounds having the general formula I above with substituents selected from the following:

Y is selected from —OH, SH, alkylthio groups, arylthio groups, —OR$^{10}$ groups, —C(=O)—R$^{11}$ groups, —NR$^{12}$R$^{13}$ groups, —CN, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted heterocyclyl groups, substituted or unsubstituted aryl groups, substituted or unsubstituted heterocycly loxyalkyl groups, substituted or unsubstituted hydroxyalkyl groups, substituted or unsubstituted alkoxyalkyl groups, or substituted or unsubstituted aryloxyalkyl groups;

Z is selected from O, S, or NR$^{14}$ groups;

$R^1$, $R^2$, $R^3$, and $R^4$ may be the same or different and are independently selected from H, Cl, Br, F, I, —CN, —NO$_2$, —OH, —OR$^{15}$ groups, —NR$^{16}$R$^{17}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, or —C(=O)R$^{18}$;

$R^5$, $R^6$, $R^7$, and $R^8$ may be the same or different and are independently selected from H, Cl, Br, F, I, —NO$_2$, —OH, —OR$^{19}$ groups, —NR$^{20}$R$^{21}$ groups, —SH, —SR$^{22}$ groups, —S(=O)R$^{23}$ groups, —S(=O)$_2$R$^{24}$ groups, —CN, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, —C(=O)R$^{25}$ groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^9$ and $R^{14}$ may be the same or different and are independently selected from H, —OH, substituted or unsubstituted alkoxy groups, substituted or unsubstituted aryloxy groups, —NH$_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

$R^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

$R^{11}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, —NH(heterocyclyl) groups, —N(heterocyclyl)$_2$ groups, —N(alkyl)(heterocyclyl) groups, or substituted or unsubstituted aryl groups;

$R^{12}$ is selected from H, substituted or unsubstituted alkyl groups, substituted or unsubstituted aryl groups, or substituted or unsubstituted heterocyclyl groups;

$R^{13}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH (aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)N(heterocyclyl)$_2$ groups, —C(=O)N(alkyl)(heterocyclyl) groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{15}$ and $R^{19}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl, substituted or unsubstituted diheterocyclylaminoalkyl, substituted or unsubstituted (heterocyclyl)(alkyl)aminoalkyl, substituted or unsubstituted (heterocyclyl)(aryl)aminoalkyl, substituted or unsubstituted alkoxyalkyl groups, substituted or unsubstituted hydroxyalkyl groups, substituted or unsubstituted aryloxyalkyl groups, or substituted or unsubstituted heterocyclyloxyalkyl groups;

$R^{16}$ and $R^{20}$ may be the same or different and are independently selected from H, substituted or unsubstituted alkyl groups, substituted or unsubstituted aryl groups, or substituted or unsubstituted heterocyclyl groups;

$R^{17}$ and $R^{21}$ may be the same or different and are independently selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups,—C(=O) NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)N(heterocyclyl)$_2$ groups, —C(=O)N(alkyl)(heterocyclyl) groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^8$, $R^{23}$, $R^{24}$, and $R^{25}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted aryloxy groups, substituted or unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups; and $R^{22}$ is selected from substituted or unsubstituted alkyl groups, substituted or unsubstituted aryl groups, or substituted or unsubstituted heterocyclyl groups.

In the third group of compounds, at least one of $R^5$, $R^6$, $R^7$, or $R^8$ is selected from substituted or unsubstituted amidinyl groups, substituted or unsubstituted guanidinyl groups, substituted or unsubstituted saturated heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups; —OR$^{19}$ groups where $R^{19}$ is selected from substituted or unsubstituted aryl groups, substituted or unsubstituted heterocyclyl groups, substituted or unsubstituted heterocyclylalkyl groups, —C(=O)H, —C(=O)-aryl groups, —C(=O)NH$_2$, —C(=O)NH(alkyl) groups, —C(=O)NH (aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted hydroxyalkyl groups, substituted or unsubstituted alkoxyalkyl groups, substituted or unsubstituted aryloxyalkyl groups, or substituted and unsubstituted heterocyclyloxyalkyl groups; —NR$^{20}$R$^{21}$ groups where $R^{20}$ is selected from substituted or unsubstituted heterocyclyl groups; —NR$^{20}$R$^{21}$ groups where $R^{21}$ is selected from substituted or unsubstituted heterocyclyl groups, —C(=O)H, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, substituted or unsubstituted heterocyclylalkyl groups, or substituted or unsubstituted heterocyclyloxyalkyl groups; or —C(=O)R$^{25}$ groups where R$^{25}$ is selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted aryl groups, substituted or unsubstituted aryloxy groups, or substituted or unsubstituted heterocyclyl groups.

In yet another embodiment, the present invention encompasses compounds of formula I in which the substituents described below define a fourth group of compounds:

Y is selected from —OH, SH, alkylthio groups, arylthio groups, —OR$^{10}$ groups, —C(=O)—R$^{11}$ groups, —NR$^{12}$R$^{13}$ groups, —CN, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted heterocyclyl groups, substituted or unsubstituted aryl groups, substituted or unsubstituted heterocyclyloxyalkyl groups, substituted or unsubstituted hydroxyalkyl groups, substituted or unsubstituted alkoxyalkyl groups, or substituted or unsubstituted aryloxyalkyl groups;

Z is selected from O, S, or NR$^{14}$ groups;

R$^1$, R$^2$, R$^3$, and R$^4$ may be the same or different and are independently selected from H, Cl, Br, F, I, —CN, —NO$_2$, —OH, —OR$^{15}$ groups, —NR$^{16}$R$^{17}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, or —C(=O)R$^{18}$ groups;

R$^5$, R$^6$, R$^7$, and R$^8$ may be the same or different and are independently selected from H, Cl, Br, F, I, —NO$_2$, —OH, —OR$^{19}$ groups, —NR$^{20}$R$^{21}$ groups, —SH, —SR$^{22}$ groups, —S(=O)R$^{23}$ groups, —S(=O)$_2$R$^{24}$ groups, —CN, substituted or unsubstituted amidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, —C(=O)R$^{25}$ groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

R$^9$ and R$^{14}$ may be the same or different and are independently selected from H, —OH, substituted or unsubstituted alkoxy groups, substituted or unsubstituted aryloxy groups, —NH$_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups;

R$^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —NH$_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

R$^{11}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, —NH(heterocyclyl) groups, —N(heterocyclyl)$_2$ groups, —N(alkyl)(heterocyclyl) groups, or substituted or unsubstituted aryl groups;

R$^{12}$ is selected from H, substituted or unsubstituted alkyl groups, substituted or unsubstituted aryl groups, or substituted or unsubstituted heterocyclyl groups;

R$^{13}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH (aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)N(heterocyclyl)$_2$ groups, —C(=O)—N(alkyl)(heterocyclyl) groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{15}$ and $R^{19}$ may be the same or different and are independently selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl, substituted or unsubstituted diheterocyclylaminoalkyl, substituted or unsubstituted (heterocyclyl)(alkyl)aminoalkyl, substituted or unsubstituted (heterocyclyl)(aryl)aminoalkyl, substituted or unsubstituted alkoxyalkyl groups, substituted or unsubstituted hydroxyalkyl groups, substituted or unsubstituted aryloxyalkyl groups, or substituted or unsubstituted heterocyclyloxyalkyl groups;

$R^{16}$ and $R^{20}$ may be the same or different and are independently selected from H, substituted or unsubstituted alkyl groups, substituted or unsubstituted aryl groups, or substituted or unsubstituted heterocyclyl groups;

$R^{17}$ and $R^{21}$ may be the same or different and are independently selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups,—C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups;

$R^{18}$, $R^{23}$, $R^{24}$, and $R^{25}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, substituted or unsubstituted alkyl groups, substituted or unsubstituted aryl groups, —OH, substituted or unsubstituted alkoxy groups, substituted or unsubstituted aryloxy groups, substituted or unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups; and $R^{22}$ is selected from substituted or unsubstituted alkyl groups, substituted or unsubstituted aryl groups, or substituted or unsubstituted heterocyclyl groups.

In the fourth group of compounds, at least one of $R^1$, $R^2$, $R^3$, or $R^4$ is an —OR$^{15}$ group and $R^{15}$ is selected from substituted or unsubstituted heterocyclylalkyl groups, substituted or unsubstituted dialkylaminoalkyl groups, substituted or unsubstituted alkylaminoalkyl groups, substituted or unsubstituted aminoalkyl groups, substituted or unsubstituted diarylaminoalkyl groups, substituted or unsubstituted arylaminoalkyl groups, substituted or unsubstituted (alkyl)(aryl)aminoalkyl groups, substituted or unsubstituted heterocyclyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, or substituted or unsubstituted (heterocyclyl)(aryl)aminoalkyl groups.

In the first, second, or third group of compounds Z is preferably an —NR$^{14}$ group, more preferably where R$^{14}$ is H. Preferred compounds of the fourth group include those compounds in which Z is an —NR$^{10}$ group, more preferably where R$^{10}$ is H.

Y is preferably an —OR$^{10}$ group, an —NR$^{12}$R$^{13}$ group, or a substituted or unsubstituted alkynyl group, or more preferably is an —1NR$^{12}$N$^{13}$ group in the first, second, third, and fourth groups of compounds. In more preferred compounds of the first group, Y is a NR$^{12}$R$^{13}$ group and R$^{12}$ is H. In more preferred compounds of the second and third groups, Y is a NR$^{12}$R$^{13}$ group and one or both of R$^{12}$ and R$^{13}$ are H.

Other preferred compounds of the first, second, and third groups include those where Y is selected from —N(CH$_3$)$_2$, —NH(CH$_3$), —NH(CH$_2$CH$_3$), —N(CH$_2$CH$_3$)$_2$, —NH(aryl) groups, —N(aryl)$_2$ groups, —NHNH$_2$, —NHN(CH$_3$)$_2$, —N(CH$_3$)NH(CH$_3$), —NH(CH$_2$)$_m$NH$_2$ groups, —NH(CH$_2$)$_m$NH(alkyl) groups, —NH(CH$_2$)$_m$N(alkyl)$_2$ groups, —N(alkyl)(CH$_2$)$_m$NH$_2$ groups, —N(alkyl)(CH$_2$)$_m$—NH(alkyl) groups, —N(alkyl)(CH$_2$)$_m$N(alkyl)$_2$ groups, —NH(CH$_2$)$_n$(heterocyclyl) groups, —N(alkyl)[(CH$_2$)$_n$(heterocyclyl)] groups, —NH(CH$_2$)$_m$OH groups, —NH(CH$_2$)$_m$OCH$_3$ groups, —NHCH$_2$CH(NH$_2$)CH(CH$_3$)$_2$, —NH(2-aminocyclohexyl), —NH(cyclohexyl), —NHOCH$_3$, —NH(N-morpholinyl), —NH(quinuclidyl), especially —NH(quinuclid-3-yl), or groups where R$^{12}$ and R$^{13}$ join to form a substituted or unsubstituted saturated 5 or 6 membered N-containing ring, where m is an integer ranging from 2 to 4 such as 2, 3, or 4 and n is an integer ranging from 0 to 3 such as 0, 1, 2, or 3.

More preferred compounds of the first, second, and third also include those in which Y is selected from —NH(5-benzimidazolyl), —NH(CH$_2$)$_2$N(CH$_3$)$_2$, —NH(CH$_2$)$_2$OH, —NH(CH$_2$)(4-imidazolyl), —NH(CH$_2$)(3-imidazolyl), —NH(CH$_2$)(4-pyridyl), —NH(CH$_2$)(2-pyridyl), —NH(CH$_2$)(3-pyridyl), —NH(CH$_2$)(2-tetrahydrofuranyl), —NH(CH$_2$)(4-piperidinyl), —NH(CH$_2$)(3-piperidinyl), —NH(CH$_2$)$_2$[2-(N-methylpyrrolidinyl)], —NH(CH$_2$)$_2$(2-pyrrolidinyl), —NH(CH$_2$)[2-(N-methylpyrrolidinyl)], —NH(CH$_2$)(2-pyrrolidinyl), —NH(3-piperidinyl), or —NH(3-pyrrolidinyl).

Preferred compounds of the first and second groups include those compounds where R$^1$, R$^2$, R$^3$, R$^4$, R$^6$, R$^7$, and R$^8$ are all H. Other preferred compounds of the first, second, third, and fourth groups include those where $R^1$ is selected from H, substituted or unsubstituted alkoxy groups, substituted or unsubstituted heterocyclylalkoxy groups, substituted or unsubstituted heterocyclyloxy groups, substituted or unsubstituted heterocyclyl groups, substituted or unsubstituted alkyl-, heterocyclyl-, or aryl-aminoalkyl groups, substituted or unsubstituted dialkylaminoalkyl groups, substituted or unsubstituted diarylaminoalkyl groups, substituted or unsubstituted (alkyl)(aryl)aminoalkyl groups, substituted or unsubstituted alkyl- or aryl-aminoalkoxy groups, substituted or unsubstituted dialkylaminoalkoxy groups, or substituted or unsubstituted diarylaminoalkoxy groups. Still other compounds of the first, second, third, and fourth groups include those in which $R^1$ is selected from F, Cl, substituted or unsubstituted alkoxy groups, substituted or unsubstituted heterocyclylalkoxy groups, substituted or unsubstituted heterocyclyl groups, substituted or unsubstituted alkyl-, heterocyclyl-, or aryl-aminoalkyl groups, substituted or unsubstituted dialkylaminoalkyl groups, substituted or unsubstituted diarylaminoalkyl groups, substituted or unsubstituted (alkyl)(aryl)aminoalkyl groups, substituted or unsubstituted alkylaminoalkoxy groups, substituted or unsubstituted arylaminoalkoxy groups, substituted or unsubstituted dialkylaminoalkoxy groups, substituted or unsubstituted diarylaminoalkoxy groups, or substituted or unsubstituted (alkyl)(aryl) aminoalkoxy groups. Particular examples include: —OCH$_3$, —OCH$_2$CH$_2$(N-morpholinyl), —N-morpholinyl, —N-cis-dialkylmorpholinyl, —N-(4-alkyl)piperazinyl, —OCH$_2$CH$_2$N(alkyl)$_2$ groups, —OCH$_2$CH$_2$NH(alkyl) groups, —OCH$_2$CH$_2$NH$_2$, —OCH$_2$CH$_2$NH(aryl) groups, —OCH$_2$CH$_2$N(aryl)$_2$ groups, —OCH$_2$CH$_2$N(alkyl)(aryl) groups, alkoxy groups, —O(4-piperidinyl), —O[4-(1-alkyl) piperidinyl] groups, —O[3-(1-alkyl)piperidinyl] groups, —O[3-quinuclidinyl], —OCH$_2$(2-pyridyl), —OCH$_2$(4-pyridyl), —O(3-pyrrolidinyl), or —O[3-(1-alkyl)pyrrolidinyl] groups.

Still other preferred compounds of the first, second, third, and fourth groups include those in which $R^2$ is selected from F, Cl, —NO$_2$, —OCH$_3$, N-morpholinyl, —N-cis-dialkylmorpholinyl, —N-(4-alkyl)piperazinyl, or —OCH$_2$(2-pyridyl). Other preferred compounds of the first, second, third, and fourth groups include those where $R^2$ is selected from H, F, Cl, —NO$_2$, substituted or unsubstituted heterocyclylalkoxy groups, or substituted or unsubstituted heterocyclyl groups. Yet other preferred compounds of the first, second, third, and fourth groups include those where $R^2$ is selected from F, Cl, —NO$_2$, substituted or unsubstituted alkoxy groups, substituted or unsubstituted heterocyclylalkoxy groups, substituted or unsubstituted heterocyclyl groups, substituted or unsubstituted alkyl-, heterocycyl-, and aryl-aminoalkyl groups, substituted or unsubstituted dialkyl- and diaryl-aminoalkyl groups, substituted or unsubstituted alkylarylaminoalkyl groups, substituted or unsubstituted alkyl- and aryl-aminoalkoxy groups, substituted or unsubstituted dialkyl- and diaryl-aminoalkoxy groups, or substituted or unsubstituted alkylarylaminoalkoxy groups.

Still further preferred compounds of the first, second, third, and fourth groups include those where $R^6$ is an alkyl group having from one to four carbon atoms. In other preferred compounds of the first, second, third, and fourth groups, $R^7$ is an alkyl group having from one to four carbon atoms. Still further preferred compounds of the four groups are those in which $R^6$ or $R^7$ is an —OR$^{19}$ group and R$^{19}$ is an alkyl group, an aryl group, a heterocyclyl group, or a heterocyclylalkyl group.

In still other preferred compounds of the first, second, third, and fourth groups, $R^6$ or $R^7$ is a —OCH$_2$(CH$_2$)$_q$(heterocyclyl) group and q is 0, 1, 2, 3, or 4, more preferably where the heterocyclyl group of the —OCH$_2$(CH$_2$)$_q$(heterocyclyl) group is a heterocycle selected from substituted or unsubstituted morpholine, substituted or unsubstituted piperazine, substituted or unsubstituted piperidine, substituted or unsubstituted pyrrolidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted furan, substituted or unsubstituted thiophene, substituted or unsubstituted tetrahydrofuran, substituted or unsubstituted tetrahydrothiophene, substituted or unsubstituted benzimidazole, substituted or unsubstituted benzoxazole, or substituted or unsubstituted benzothiazole.

In groups including heterocyclyl groups, the heterocyclyl may be attached in various ways. For example, in the —OCH$_2$(CH$_2$)$_q$(heterocyclyl) group, the heterocyclyl group may be bonded to a methylene carbon of the —OCH$_2$(CH$_2$)$_q$ group of the —OCH$_2$(CH$_2$)$_q$(heterocyclyl) through various ring members. By way of non-limiting example, where q is 1 and the heterocyclyl group is tetrahydrofuran, the group could be represented by the formula —OCH$_2$CH$_2$(tetrahydrofuranyl) which corresponds to the following two structures:

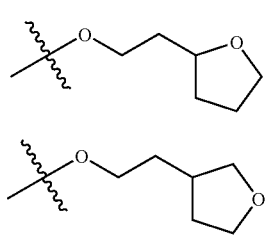

III

IV where structure III represents the group that can be referred to as the —OCH$_2$CH$_2$(2-tetrahydrofuranyl) group and structure IV represents the group that can be referred to as the —OCH$_2$CH$_2$(3-tetrahydrofuranyl) group. When the heterocyclyl group is a N-containing heterocycle, such as, but not limited to piperidine, piperazine, morpholine, or pyrrolidine, the heterocycle can be bonded to the methylene carbon through a ring carbon atom or through a nitrogen atom in the ring of the N-containing heterocycle. Both of these are preferred. Where the heterocyclyl group is a piperidine and q is 2 for an —OCH$_2$(CH$_2$)$_q$(heterocyclyl) group, the following structures are possible and preferred:

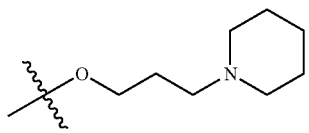

V

VI

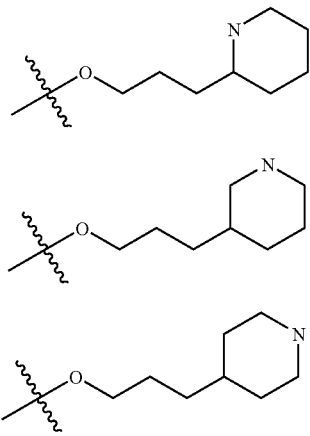

VII

VIII

Structure V is an example of a —O(CH$_2$)$_3$(N-piperidinyl) or —O(CH$_2$)$_3$(1-piperidinyl) group. Structure VI is an example of a —O(CH$_2$)$_3$-(2-piperidinyl) group. Structure VII is an example of a —O(CH$_2$)$_3$(3-piperidinyl) group. Structure VIII is an example of a —O(CH$_2$)$_3$(4-piperidinyl) group. Where the heterocyclyl group is a piperazine and q is 1 for an —OCH$_2$(CH$_2$)$_q$(heterocyclyl) group, the following structures are possible and preferred:

IX

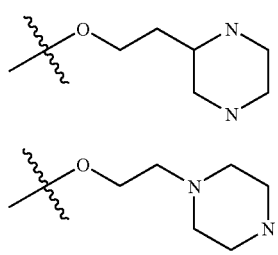

X

Structure IX is an example of a —O(CH$_2$)$_2$(2-piperazinyl) group, and structure X is an example of a —O(CH$_2$)$_2$(1-piperazinyl) or —O(CH$_2$)$_2$(N-piperazinyl)group. Where the heterocyclyl group is a morpholine and q is 1 for an —OCH$_2$(CH$_2$)$_q$(heterocyclyl) group, the following structures are possible and preferred:

XI

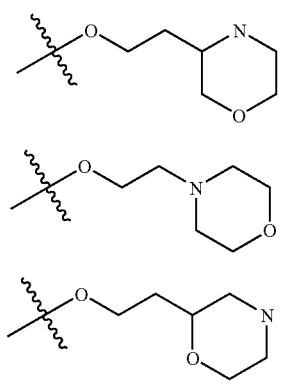

XII

XIII

Structure XI is an example of a —O(CH$_2$)$_2$(3-morpholinyl) group, structure XII is an example of a —O(CH$_2$)$_2$(4-morpholinyl) or —O(CH$_2$)$_2$(N-morpholinyl) group, and structure XIII is an example of a —O(CH$_2$)$_2$(2-morpholinyl) group. It will be observed that where the group is a pyrrolidine, and q is 1, the structures available include —O(CH$_2$)$_2$(1-pyrrolidinyl) or —O(C H$_2$)$_2$(N-pyrrolidinyl), —O(CH$_2$)$_2$(2-pyrrolidinyl), and —O(CH$_2$)$_2$(3-pyrrolidinyl).

Yet other preferred compounds of the first, second, third, and fourth groups include those where at least one of R$^5$, R$^6$, R$^7$, and R$^8$ is a substituted or unsubstituted heterocyclyl group, more specifically a substituted or unsubstituted heterocyclyl group comprising at least one O or N atom, still more particularly a substituted or unsubstituted heterocyclyl group selected from morpholine, piperazine, piperidine, 1,2,3-triazole, 1,2,4-triazole, tetrazole, pyrrolidine, pyrazole, pyrrole, thiomorpholine, thiomorpholine in which the S atom of the thiomorpholine group is bonded to one or more O atoms, homopiperazine, benzimidazole, oxazolidin-2-one, pyrrolidin-2-one, imidazole, isoxazole, oxazole, isothiazole, thiazole, thiophene, furan, pyran, tetrahydrothiophene, tetrahydrofuran, tetrahydropyran, or pyridine.

Other preferred compounds of the first, second, third, and fourth groups include those in which at least one of R$^{19}$ or R$^{21}$ is selected from substituted or unsubstituted aminoalkyl groups, substituted or unsubstituted alkylaminoalkyl groups, substituted or unsubstituted arylaminoalkyl groups, substituted or unsubstituted dialkylaminoalkyl groups, substituted or unsubstituted diarylaminoalkyl groups, (alkyl)(aryl)aminoalkyl groups, or substituted or unsubstituted heterocyclylalkyl groups, including: —CH$_2$(CH$_2$)$_p$NH$_2$ groups, —CH$_2$(CH$_2$)$_p$NH(alkyl) groups, —CH$_2$(CH$_2$)$_p$NH(aryl) groups, —CH$_2$(CH$_2$)$_p$N(alkyl)$_2$ groups, —CH$_2$(CH$_2$)$_p$N(aryl)$_2$ groups, —CH$_2$(CH$_2$)$_p$N(alkyl)(aryl) groups, or —CH$_2$(CH$_2$)$_p$(heterocyclyl) groups, wherein p is an integer ranging from 0 to 4 and the heterocyclyl group of the —CH$_2$(CH$_2$)$_p$(heterocyclyl) group is a N-containing heterocycle selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Still further preferred compounds according to the first, second, third, and fourth groups include those in which R$^{25}$ is selected from substituted or unsubstituted aryl groups, substituted or unsubstituted alkyl groups, —NH$_2$, —NH(alkyl) groups, —N(alkyl)$_2$ groups, —NH(aryl) groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, or N-containing heterocycles. In such compounds, the N-containing heterocycles are bonded to the carbonyl carbon of the —C(=O)—R$^{25}$ group through either a nitrogen atom or a carbon atom in the rings of the N-containing heterocycles. In more preferred such compounds that are provided, the N-containing heterocycle of the R$^{25}$ group is selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Preferred compounds according to the first, third, and fourth groups of compounds are also those where $R^9$ is H.

Preferred compounds of the fourth group of compounds include those where $R^1$ is an —$OR^{15}$ group and $R^{15}$ is selected from substituted or unsubstituted heterocyclylalkyl groups, substituted or unsubstituted dialkylaminoalkyl groups, substituted or unsubstituted alkylaminoalkyl groups, substituted or unsubstituted aminoalkyl groups, substituted or unsubstituted diarylaminoalkyl groups, substituted or unsubstituted arylaminoalkyl groups, substituted or unsubstituted (alkyl)(aryl)aminoalkyl groups, substituted or unsubstituted heterocyclyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, or substituted or unsubstituted (heterocyclyl)(aryl)aminoalkyl groups.

Other particularly preferred inhibitors of VEGF-RTK are compounds having the structure II, tautomers of the compounds, pharmaceutically acceptable salts of the compounds, and pharmaceutically acceptable salts of the tautomers. Structure II has the following formula:

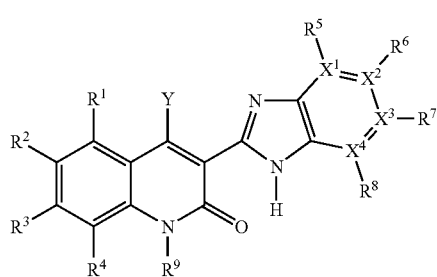

II

In compounds having structure II, Y is selected from H, —OH, —$OR^{10}$ groups, —SH, —$SR^{11}$ groups, —$NR^{12}R^{13}$ groups, —CN, —C(=O)—$R^{14}$ groups, substituted or unsubstituted alkyl groups, substituted or unsubstituted alkenyl groups, substituted or unsubstituted alkynyl groups, substituted or unsubstituted aralkyl groups, substituted or unsubstituted heterocyclylalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted heterocyclyl groups, substituted or unsubstituted aryl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups.

In preferred compounds of structure II, Y is selected from H, —OH, —$OR^9$ groups, or —$NR^{11}R^{12}$ groups. More preferably, Y is a —$NR^{11}R^{12}$ group. Still more preferably, Y is a —$NR^{11}R^{12}$ group and both $R^{11}$ and $R^{12}$ are hydrogen. In other preferred compounds having the structure II, Y is selected from —$N(CH_3)_2$, —$NH(CH_3)$, —$NH(CH_2CH_3)$, —$N(CH_2CH_3)_2$, —NH(aryl) groups, —$N(aryl)_2$ groups, —$NHNH_2$, —$NHN(CH_3)_2$, —$N(CH_3)NH(CH_3)$, —NH$(CH_2)_mNH_2$ groups, —NH$(CH_2)_m$NH(alkyl) groups, —NH$(CH_2)_m$N(alkyl)$_2$ groups, —N(alkyl)$(CH_2)_m$NH$_2$ groups, —N(alkyl)$(CH_2)_m$NH(alkyl) groups, —N(alkyl)$(CH_2)_m$N(alkyl)$_2$ groups, —NH$(CH_2)_n$(heterocyclyl) groups, —N(alkyl)[$(CH_2)_n$(heterocyclyl)] groups, —NH$(CH_2)_m$OH groups, —NH$(CH_2)_m$OCH$_3$ groups, —NHCH$_2$CH(NH$_2$)CH(CH$_3)_2$, —NH(2-aminocyclohexyl), —NH(cyclohexyl), —NHOCH$_3$, —NH(N-morpholinyl), —NH(quinuclidyl), especially —NH(quinuclid-3-yl), and groups where $R^{11}$ and $R^{12}$ join to form a substituted or unsubstituted saturated 5 or 6 membered N-containing ring, where m is 2, 3, or 4 and n is 0, 1, 2, or 3. Still more preferred compounds of this type are those in which Y is selected from —NH(5-benzimidazolyl), —NH(CH$_2)_2$N(CH$_3)_2$, —NH(CH$_2)_2$OH, —NH(CH$_2$)(4-imidazolyl), —NH(CH$_2$)(3-imidazolyl), —NH(CH$_2$)(4-pyridyl), —NH(CH$_2$)(2-pyridyl), —NH(CH$_2$)(3-pyridyl), —NH(CH$_2$)(2-tetrahydrofuranyl), —NH(CH$_2$)(4-piperidinyl), —NH(CH$_2$)(3-piperidinyl), —NH(CH$_2)_2$[2-(N-methyl-pyrrolidinyl)], —NH(CH$_2)_2$(2-pyrrolidinyl), —NH(CH$_2$)[2-(N-methylpyrrolidinyl)], —NH(CH$_2$)(2-pyrrolidinyl), —NH(3-piperidinyl), or —NH(3-pyrrolidinyl).

In compounds of structure II, $X^1$, $X^2$, $X^3$, and $X^4$ are selected from C or N and at least one of $X^1$, $X^2$, $X^3$, and $X^4$ is N. In some preferred compounds of structure II, $X^1$ is N, $R^5$ is absent or H, and $X^2$, $X^3$, and $X^4$ are all C. In other preferred compounds of structure II, $X^2$ is N, $R^6$ is absent or H, and $X^1$, $X^3$, and $X^4$ are C. In other preferred compounds of structure II, $X^3$ is N, $R^7$ is absent or H, and $X^1$, $X^2$, and $X^4$ are all C. In still other preferred compounds of structure II, $X^4$ is N, $R^8$ is absent or H, and $X^1$, $X^2$, and $X^3$ are all C.

In compounds of structure II, $R^1$, $R^2$, $R^3$, $R^4$, $R^5$, $R^6$, $R^7$, and $R^8$ may be the same or different and are independently selected from H, Cl, Br, F, I, —NO$_2$, —CN, —OH, —$OR^{15}$ groups, —$NR^{16}R^{17}$ groups, —C(=O)$R^{18}$ groups, —SH, —$SR^{19}$ groups, —S(=O)$R^{20}$ groups, S(=O)$_2R^{21}$ groups, substituted or unsubstituted amidinyl groups, substituted or unsubstituted guanidinyl groups, substituted or unsubstituted primary, secondary, or tertiary alkyl groups, substituted or unsubstituted aryl groups, substituted or unsubstituted alkenyl groups, substituted or unsubstituted alkynyl groups, substituted or unsubstituted heterocyclyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylalkyl groups, substituted or unsubstituted aminoalkyl groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. In compounds of structure II, $R^5$ is absent or is H if $X^1$ is N, $R^6$ is absent or is H if $X^2$ is N, $R^7$ is absent or is H if $X^3$ is N, and $R^8$ is absent or is H if $X^4$ is N.

Some preferred compounds have the structure II where at least one of $R^1$, $R^2$, $R^3$, $R^4$, $R^5$, $R^6$, $R^7$, or $R^8$ is a substituted or unsubstituted heterocyclyl group, and, in more particular embodiments, a substituted or unsubstituted heterocyclyl group selected from morpholine, piperazine, piperidine, 1,2,3-triazole, 1,2,4-triazole, tetrazole, pyrrolidine, pyrazole, pyrrole, thiomorpholine, homopiperazine, benzimidazole, oxazolidin-2-one, pyrrolidin-2-one, imidazole, isoxazole, oxazole, isothiazole, thiazole, thiophene, furan, pyran, tetrahydrothiophene, tetrahydrofuran, tetrahydropyran, and pyridine.

Still other preferred compounds having structure II are those in which $R^1$, $R^2$, $R^3$, and $R^4$ are H. In some preferred embodiments, $R^1$ is selected from H, substituted or unsubstituted alkoxy groups, substituted or unsubstituted heterocyclylalkoxy groups, substituted or unsubstituted heterocyclyloxy groups, substituted or unsubstituted heterocyclyl groups, substituted or unsubstituted alkyl-, heterocyclyl-, or aryl-aminoalkyl groups, substituted or unsubstituted dialkylaminoalkyl groups, substituted or unsubstituted diarylaminoalkyl groups, substituted or unsubstituted (alkyl)(aryl)aminoalkyl groups, substituted or unsubstituted alkyl- or aryl-aminoalkoxy groups, substituted or unsubstituted dialkylaminoalkoxy groups, or substituted or unsubstituted diarylaminoalkoxy groups. In other preferred compounds, $R^1$ is selected from F, Cl, substituted or unsubstituted alkoxy groups, substituted or unsubstituted heterocyclylalkoxy groups, substituted or unsubstituted heterocyclyl groups, substituted or unsubstituted alkyl-, heterocyclyl-, or aryl-aminoalkyl groups, substituted or unsubstituted dialkylaminoalkyl groups, substituted or unsubstituted diarylaminoalkyl groups, substituted or unsubstituted (alkyl)(aryl)aminoalkyl groups, substituted or unsubstituted alkylaminoalkoxy groups, substituted or unsubstituted arylaminoalkoxy groups, substituted or unsubstituted dialkylaminoalkoxy groups, substituted or unsubstituted diarylaminoalkoxy groups, or substituted or unsubstituted (alkyl)(aryl)aminoalkoxy groups. Particular examples include: —$OCH_3$, —$OCH_2CH_2$(N-morpholinyl), —N-morpholinyl, —N-cis-dimethylmorpholinyl, —N-(4-alkyl)piperazinyl, —$OCH_2CH_2N(alkyl)_2$ groups, —$OCH_2CH_2NH(alkyl)$ groups, —$OCH_2CH_2NH_2$, —$OCH_2CH_2NH(aryl)$ groups, —$OCH_2CH_2N(aryl)_2$ groups, alkoxy groups, —$OCH_2CH_2N(alkyl)(aryl)$ groups, —O(4-piperidinyl), —O[4-(1-alkyl)piperidinyl] groups, —O[3-(1-alkyl)piperidinyl] groups, —O[3-quinuclidinyl], —$OCH_2$(2-pyridyl), —$OCH_2$(4-pyridyl), —O(3-pyrrolidinyl), —O[3-(1-alkyl)pyrrolidinyl], or other —O(heterocyclyl) groups not listed in this paragraph.

In other compounds having the structure II, $R^2$ is selected from F, Cl, —$NO_2$, —$OCH_3$, —N-morpholinyl, —N-cis-dialkylmorpholinyl, —N-(4-alkyl)piperazinyl, or —$OCH_2$(2-pyridyl). In yet other compounds having the structure II, $R^2$ is selected from H, F, Cl, —$NO_2$, substituted or unsubstituted heterocyclylalkoxy groups, or substituted or unsubstituted heterocyclyl groups. Yet other preferred compounds having the structure II include those where $R^2$ is selected from F, Cl, —$NO_2$, substituted or unsubstituted alkoxy groups, substituted or unsubstituted heterocyclylalkoxy groups, substituted or unsubstituted heterocyclyl groups, substituted or unsubstituted alkyl-, heterocycyl-, and aryl-aminoalkyl groups, substituted or unsubstituted dialkyl- and diaryl-aminoalkyl groups, substituted or unsubstituted alkylarylaminoalkyl groups, substituted or unsubstituted alkyl- and aryl-aminoalkoxy groups, substituted or unsubstituted dialkyl- and diaryl-aminoalkoxy groups, or substituted or unsubstituted alkylarylaminoalkoxy groups.

In some preferred compounds having structure II, at least two of $X^1$, $X^2$, $X^3$, and $X^4$ are C and the corresponding substituents $R^5$, $R^6$, $R^7$, and $R^8$ are hydrogen, and at least one of $X^1$, $X^2$, $X^3$, and $X^4$ is N. In yet other preferred compounds having structure II, three of $R^5$, $R^6$, $R^7$, and $R^8$ are hydrogen and one of $X^1$, $X^2$, $X^3$, and $X^4$ is N. In still other more preferred compounds of structure II, $R^6$, $R^7$, or both $R^6$ and $R^7$ are alkyl groups such as those having from one to four carbon atoms. In yet other preferred compounds of structure II, $R^6$ or $R^7$ is an —$OR^{14}$ group and $R^{14}$ is an alkyl, aryl, heterocyclyl, or heterocyclylalkyl group. In still further compounds of structure II, $R^6$ or $R^7$ is a —$OCH_2(CH_2)_q$(heterocyclyl) group and q is 0, 1, 2, 3, or 4. In more preferred compounds in which $R^6$ or $R^7$ is a —$OCH_2(CH_2)_q$-(heterocyclyl) group, the heterocyclyl group of the —$OCH_2(CH_2)_n$(heterocyclyl) group is a heterocycle selected from substituted or unsubstituted morpholine, substituted or unsubstituted piperazine, substituted or unsubstituted piperidine, substituted or unsubstituted pyrrolidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted thiomorpholine in which the S atom of the thiomorpholine group is bonded to one or more O atoms, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted furan, substituted or unsubstituted thiophene, substituted or unsubstituted tetrahydrofuran, substituted or unsubstituted tetrahydrothiophene, substituted or unsubstituted benzimidazole, substituted or unsubstituted benzoxazole, or substituted or unsubstituted benzothiazole.

In compounds of structure II, $R^9$ is selected from H, —OH, substituted or unsubstituted alkoxy groups, substituted or unsubstituted aryloxy groups, —$NH_2$, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, substituted or unsubstituted alkyl groups, substituted or unsubstituted aryl groups, —C(=O)H, —C(=O)-alkyl groups, or —C(=O)-aryl groups. One group of particularly preferred compounds of structure II are those in which $R^9$ is hydrogen.

In compounds of structure II, $R^{10}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)O-alkyl groups, —C(=O)O-aryl groups, —C(=O)$NH_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —$NH_2$, —NH(alkyl) groups, —NH(aryl) groups, —N(alkyl)$_2$ groups, —N(alkyl)(aryl) groups, —N(aryl)$_2$ groups, —C(=O)NH(heterocyclyl) groups, —C(=O)N(heterocyclyl)$_2$ groups, —C(=O)N(alkyl)(heterocyclyl) groups, or —C(=O)N(aryl)(heterocyclyl) groups;

In compounds of structure II, $R^{11}$ and $R^{19}$ may be the same or different and are independently selected from substituted or unsubstituted alkyl groups, or substituted or unsubstituted aryl groups whereas $R^{12}$ is selected from H, substituted or unsubstituted alkyl groups, substituted or unsubstituted aryl groups, or substituted or unsubstituted heterocyclyl groups.

In compounds of structure II, $R^{13}$ is selected from H, substituted or unsubstituted alkyl groups, substituted or unsubstituted aryl groups, substituted or unsubstituted heterocyclyl groups, —OH, alkoxy groups, aryloxy groups, —NH$_2$, substituted or unsubstituted heterocyclylalkyl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted alkylamino groups, substituted or unsubstituted arylamino groups, substituted or unsubstituted dialkylamino groups, substituted or unsubstituted diarylamino groups, substituted or unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)N(alkyl)(heterocyclyl) groups, —C(=O)—N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, or substituted or unsubstituted heterocyclyloxyalkyl groups. $R^{12}$ and $R^{13}$ may join together to form a 5 to 7 membered saturated or unsaturated, substituted or unsubstituted N-containing ring.

In compounds of structure II, $R^{14}$ is selected from H, —OH, alkoxy groups, aryloxy groups, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —NH(heterocyclyl) groups, —N(heterocyclyl)$_2$ groups, —N(alkyl)(heterocyclyl) groups, or —N(aryl)(heterocyclyl) groups.

In compounds of structure II, $R^{15}$ is selected from substituted or unsubstituted alkyl groups, substituted or unsubstituted aryl groups, substituted or unsubstituted heterocyclyl groups, substituted or unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (alkyl)(aryl)aminoalkyl groups, substituted or unsubstituted heterocyclylaminoalkyl groups, substituted or unsubstituted diheterocyclylaminoalkyl groups, substituted or unsubstituted (heterocyclyl)(alkyl)aminoalkyl groups, substituted or unsubstituted (heterocyclyl)(aryl)aminoalkyl groups, substituted or unsubstituted alkoxyalkyl groups, substituted or unsubstituted aryloxyalkyl groups, substituted or unsubstituted hydroxyalkyl groups, or substituted or unsubstituted heterocyclyloxyalkyl groups.

In compounds of structure II, $R^{16}$ is selected from H, substituted or unsubstituted alkyl groups, substituted or unsubstituted aryl groups, or substituted or unsubstituted heterocyclyl groups whereas $R^{17}$ is selected from H, substituted or unsubstituted alkyl groups, substituted or unsubstituted aryl groups, substituted or unsubstituted heterocyclyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted or unsubstituted aminoalkyl groups, substituted or unsubstituted alkylaminoalkyl groups, substituted or unsubstituted dialkylaminoalkyl groups, substituted or unsubstituted arylaminoalkyl groups, substituted or unsubstituted diarylaminoalkyl groups, substituted or unsubstituted (aryl)(alkyl)aminoalkyl groups, substituted or unsubstituted heterocyclylalkyl groups, —C(=O)-heterocyclyl groups, —C(=O)-Oheterocyclyl groups, —C(=O)NH(heterocyclyl) groups, —C(=O)N(heterocyclyl)$_2$ groups, —C(=O)—N(alkyl)(heterocyclyl) groups, —C(=O)N(aryl)(heterocyclyl) groups, substituted or unsubstituted heterocyclylaminoalkyl groups, substituted or unsubstituted hydroxyalkyl groups, substituted or unsubstituted alkoxyalkyl groups, substituted or unsubstituted aryloxyalkyl groups, substituted or unsubstituted heterocyclyloxyalkyl groups, —OH, substituted or unsubstituted alkoxy groups, substituted or unsubstituted aryloxy groups, or —NH$_2$ groups. $R^{16}$ and $R^{17}$ may join together to form a 5 to 7 membered saturated or unsaturated, substituted or unsubstituted N-containing ring.

Finally, in compounds of structure II, $R^{18}$, $R^{20}$, and $R^{21}$ may be the same or different and are independently selected from H, —NH$_2$, —NH(alkyl) groups, —NH(aryl) groups, —N(alkyl)$_2$ groups, —N(aryl)$_2$ groups, —N(alkyl)(aryl) groups, substituted or unsubstituted alkyl groups, substituted or unsubstituted aryl groups, —OH, substituted or unsubstituted alkoxy groups, substituted or unsubstituted aryloxy groups, substituted or unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, or —N(aryl)O-aryl groups.

Compounds having the structure II may include those in which $R^{18}$ is selected from substituted or unsubstituted alkyl groups, substituted or unsubstituted aryl groups, —NH$_2$, —NH(alkyl) groups, —N(alkyl)$_2$ groups, —NH(aryl) groups, —N(aryl)$_2$ groups, —N(alkyl)(aryl) groups, —NH(heterocyclyl) groups, —N(heterocyclyl)(alkyl) groups, —N(heterocyclyl)(aryl) groups, —N(heterocyclyl)$_2$ groups, or N-containing heterocycles, and the N-containing heterocycles are bonded to the carbonyl carbon of the —C(=O)—$R^{18}$ group through either a nitrogen atom or a carbon atom in the rings of the N-containing heterocycles. In still more preferred compounds in which $R^{18}$ is a N-containing heterocycle, the N-containing heterocycle of the $R^{18}$ group is selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Other preferred compounds having structure II are provided in which $R^{15}$ or $R^{17}$ is selected from substituted or unsubstituted aminoalkyl groups, substituted or unsubstituted alkylaminoalkyl groups, substituted or unsubstituted arylaminoalkyl groups, substituted or unsubstituted dialkylaminoalkyl groups, substituted or unsubstituted diarylaminoalkyl groups, substituted or unsubstituted (alkyl)(aryl)aminoalkyl groups, or substituted or unsubstituted heterocyclylaminoalkyl groups including: —$CH_2(CH_2)_p$ $NH_2$ groups, —$CH_2(CH_2)_p$NH(alkyl) groups, —$CH_2(CH_2)_p$ NH(aryl) groups, —$CH_2(CH_2)_p$N(alkyl)$_2$ groups, —$CH_2$ $(CH_2)_p$N(aryl)$_2$ groups, —$CH_2(CH_2)_p$N(alkyl)(aryl) groups, or —$CH_2(CH_2)_p$(heterocyclyl) groups, where p is an integer ranging from 0 to 4 and the heterocyclyl group of the —$CH_2$ $(CH_2)_p$(heterocyclyl) group is a N-containing heterocycle selected from substituted or unsubstituted morpholine, substituted or unsubstituted pyrrolidine, substituted or unsubstituted piperazine, substituted or unsubstituted piperidine, substituted or unsubstituted pyrrole, substituted or unsubstituted imidazole, substituted or unsubstituted pyrazole, substituted or unsubstituted 1,2,3-triazole, substituted or unsubstituted 1,2,4-triazole, substituted or unsubstituted tetrazole, substituted or unsubstituted thiomorpholine, substituted or unsubstituted homopiperazine, substituted or unsubstituted oxazolidin-2-one, substituted or unsubstituted pyrrolidin-2-one, substituted or unsubstituted pyridine, substituted or unsubstituted oxazole, substituted or unsubstituted isoxazole, substituted or unsubstituted thiazole, substituted or unsubstituted isothiazole, substituted or unsubstituted benzimidazole, substituted or unsubstituted benzoxazole, or substituted or unsubstituted benzothiazole.

Compounds of structure I are readily synthesized from simple starting molecules as shown in the following Examples. Compounds of structure I may generally be prepared using benzene substituted with nitrile or carboxylic acid groups in addition to other optional groups.

Compounds of structure I may be synthesized from simple starting molecules as shown in Schemes 1-4 and exemplified in the Examples. As shown in Scheme 1, compounds of structure I may generally be prepared using aromatic compounds substituted with amines and carboxylic acid groups.

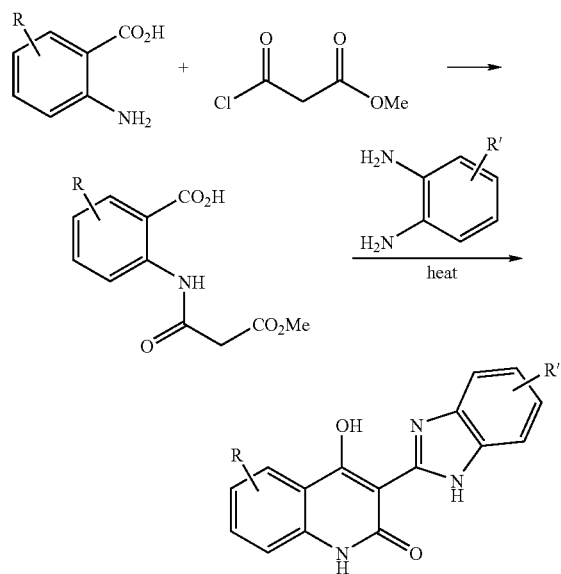

As shown in Scheme 1, a substituted aromatic compound such as a substituted or unsubstituted 2-aminobenzoic acid may be reacted with an acyl halide such as methyl 2-(chlorocarbonyl)acetate to produce an amide that will react with a substituted or unsubstituted 1,2-diaminobenzene. The resulting product is a 4-hydroxy-substituted compound of structure I. One skilled in the art will recognize that the procedure set forth in Scheme 1 may be modified to produce various compounds.

A method for preparing 4-amino substituted compounds of structure I is shown in Scheme 2. As shown in Scheme 2, aromatic compounds substituted with amine and nitrile groups may be used to synthesize 4-amino substituted compounds of structure I. A compound such as ethyl 2-cyanoacetate may be reacted with ethanol to produce ethyl 3-ethoxy-3-iminopropanoate hydrochloride. Subsequent reaction with a substituted or unsubstituted 1,2-phenylenediamine provides substituted or unsubstituted ethyl 2-benzimidazol-2-ylacetate. Reaction of a substituted or unsubstituted ethyl 2-benzimidazol-2-ylacetate with an aromatic compound having an amine and nitrile group such as substituted or unsubstituted 2-aminobenzonitrile with a base such as lithium bis(trimethylsilyl)amide or a Lewis acid such as tin tetrachloride provides the substituted or unsubstituted 4-amino substituted compound of structure I.

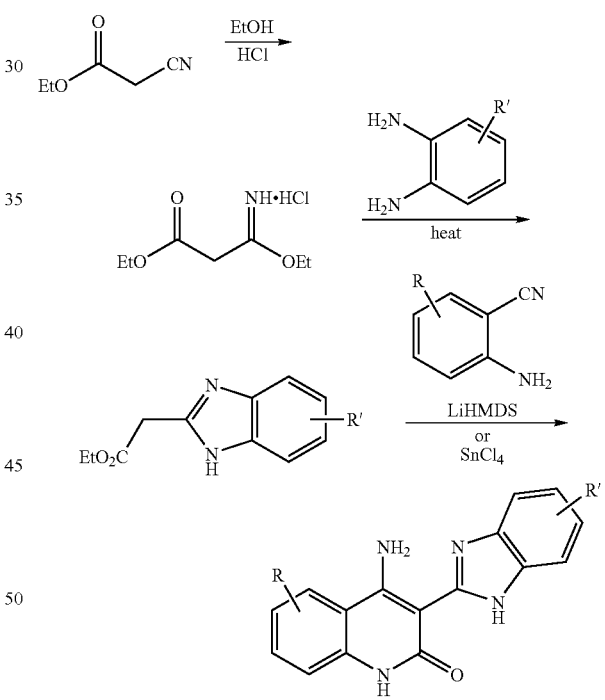

Scheme 3 illustrates a general synthetic route that allows for the synthesis of 4-dialkylamino and 4-alkylamino compounds of structure I. An inspection of Scheme 3 shows that 4-hydroxy substituted compounds of structure I may be converted into the 4-chloro derivative by reaction with phosphorous oxychloride or thionyl chloride. The 4-chloro derivative may then be reacted with an alkylamine or dialkylamine to produce the corresponding 4-alkylamino or 4-dialkylamino derivative. Deprotection affords the final 4-alkylamino or 4-dialkylamino compounds of structure I. Other groups that may be reacted with the 4-chloro derivative in this manner include, but are not limited to, ROH, RSH, and CuCN.

Scheme 3.

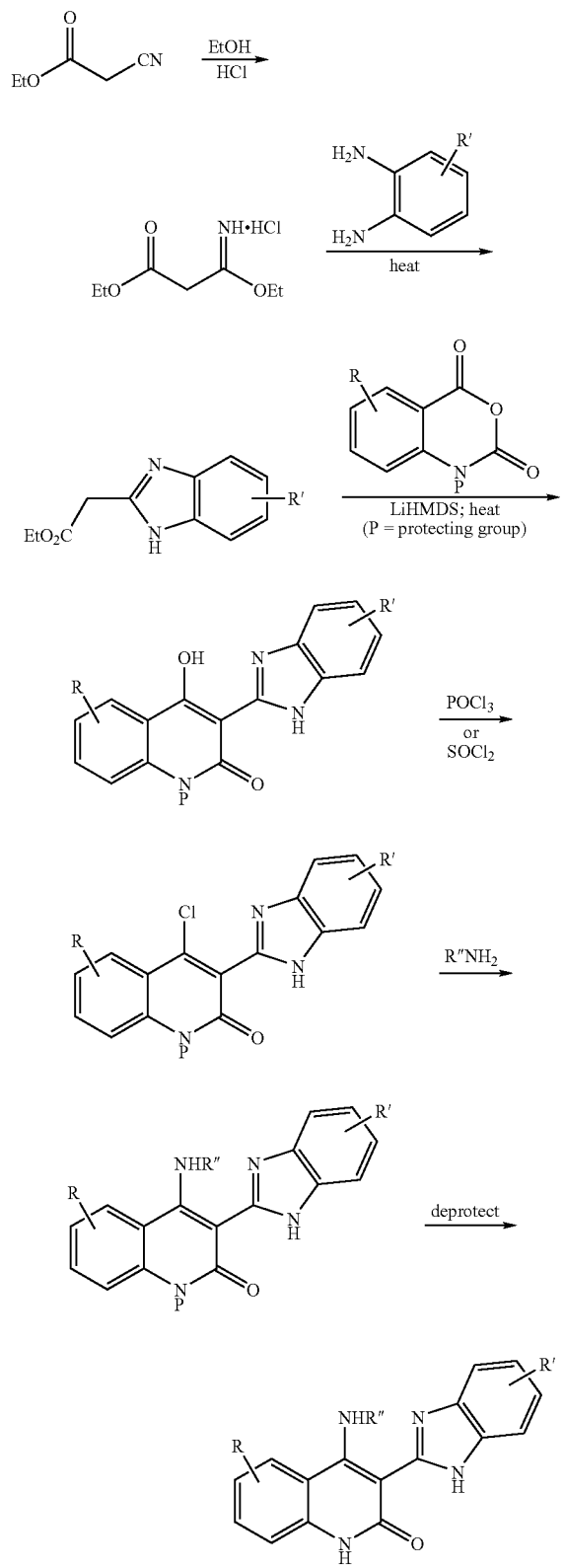

group in the 4-position may be accomplished using a substituted or unsubstituted 2-benzimidazol-2-ylacetate prepared as shown in Schemes 2 and 3.

Scheme 4.

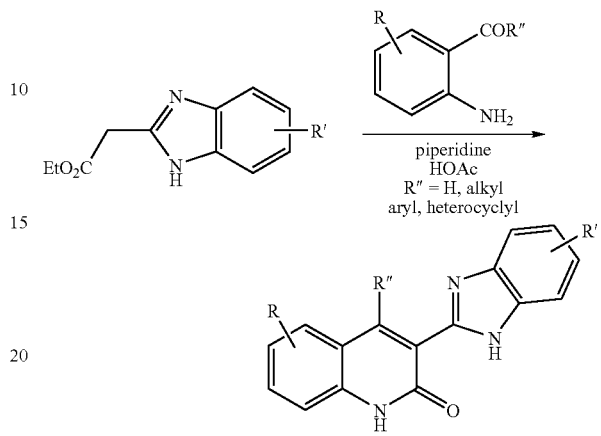

Heteroaromatic diamines may be used as precursors of compounds of structure II. The synthesis of compounds of structure II where Y=NH$_2$ is depicted in Scheme 5.

Scheme 5.

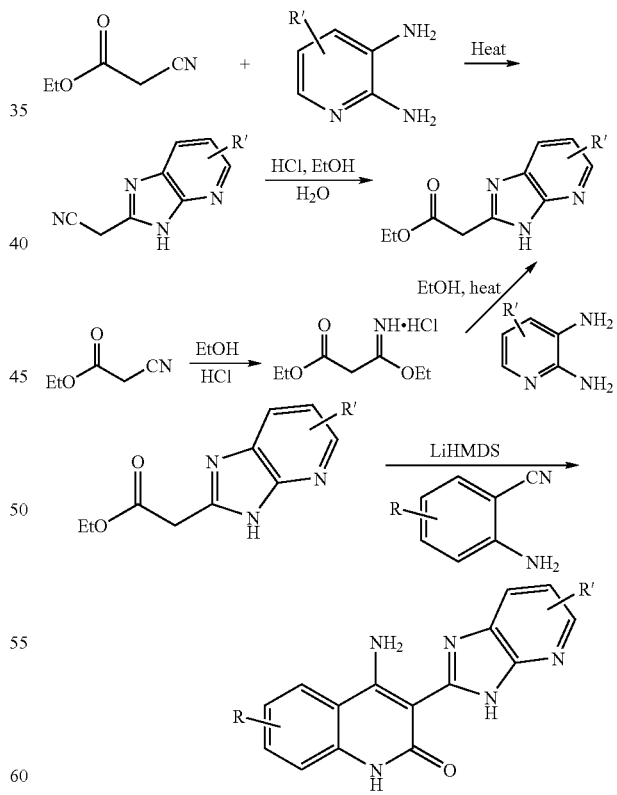

As shown in Scheme 4, the synthesis of compounds of structure I having a H, alkyl group, aryl group, or heterocyclyl A compound such as ethyl cyanoacetate may be condensed with a substituted or unsubstituted heterocycle containing two ortho amino groups such as substituted or unsubstituted 1,2-diaminopyridine to obtain a substituted or unsubstituted 2-imidazolo[5,4-b]pyridin-2-ylethanenitrile, which may subsequently be hydrolyzed in acidic medium to provide a substituted or unsubstituted ethyl 2-imidazolo[5,4-b]pyridin-2-ylacetate. As an alternate route, a substituted or unsubstituted ethyl 2-imidazolo[5,4-b]pyridin-2-ylacetate may be obtained from a compound such as the hydrochloride salt of 3-ethoxy-3-iminopropanoate and a substituted or unsubstituted 1,2-diaminopyridine. Reaction of a substituted or unsubstituted ethyl 2-imidazolo[5,4-b]pyridin-2-ylacetates with an aromatic compound having an amine and nitrile group such as substituted or unsubstituted 2-aminobenzonitrile with a base such as lithium bis(trimethylsilyl)amide provides the substituted or unsubstituted compound of structure II.

The instant invention also provides for compositions which may be prepared by mixing one or more compounds of the instant invention, or pharmaceutically acceptable salts or tautomers thereof, with pharmaceutically acceptable carriers, excipients, binders, diluents or the like, to treat or ameliorate a variety of disorders related to the activity of VEGF-RTK, more particularly angiogenesis associated with cancer. A therapeutically effective dose further refers to that amount of one or more compounds of the instant invention sufficient to result in amelioration of symptoms of the disorder. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations may be a spray or aerosol containing and appropriate solvents and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

"Treating" within the context of the instant invention, means an alleviation of symptoms associated with a disorder or disease, or halt of further progression or worsening of those symptoms, or prevention or prophylaxis of the disease or disorder. For example, within the context of treating patients in need of an inhibitor of VEGF-RTK, successful treatment may include a reduction in the proliferation of capillaries feeding a tumor or diseased tissue, an alleviation of symptoms related to a cancerous growth or tumor, proliferation of capillaries, or diseased tissue, a halting in capillary proliferation, or a halting in the progression of a disease such as cancer or in the growth of cancerous cells. Treatment may also include administering the pharmaceutical formulations of the present invention in combination with other therapies. For example, the compounds and pharmaceutical formulations of the present invention may be administered before, during, or after surgical procedure and/or radiation therapy. The compounds of the invention can also be administered in conjunction with other anti-cancer drugs including those used in antisense and gene therapy.

A method of treating a patient in need of an inhibitor of vascular endothelial growth factor receptor tyrosine kinase includes administering an effective amount of a pharmaceutical formulation according to the invention to a patient in need thereof.

A method for inhibiting tumor growth in a patient includes administering an effective amount of the compound or a pharmaceutically acceptable salt thereof to a patient having a tumor.

A method for inhibiting the proliferation of capillaries in a patient includes administering an effective amount of the compound or a pharmaceutically acceptable salt thereof according to a patient in need.

A method of preparing pharmaceutical formulations includes mixing any of the above-described compounds with a pharmaceutically acceptable carrier and water or an aqueous solution.

The present invention, thus generally described, will be understood more readily by reference to the following examples, which are provided by way of illustration and are not intended to be limiting of the present invention.

EXAMPLES

The following abbreviations are used in the Examples:

| | |
|---|---|
| ATP: | Adenosine triphosphate |
| BSA: | Bovine Serum Albumin |
| DMA: | N,N-Dimethylacetamide |
| DMF: | N,N-Dimethylformamide |
| dppf: | 1,1'(diphenylphosphino)ferrocene |
| DTT: | DL-Dithiothreitol |
| EDTA: | Ethylene diamine tetraacetic acid |
| EtOAc: | Ethyl acetate |
| EtOH: | Ethanol |
| HBTU: | O-Benzotriazol-1-yl-N,N,N',N'-tetramethyluronium hexafluorophosphate |
| $IC_{50}$ value: | The concentration of an inhibitor that causes a 50% reduction in a measured activity. |
| LiHMDS: | Lithium bis(trimethylsilyl)amide |
| MeOH: | Methanol |
| NMP: | N-methylpyrrolidone |
| THF: | Tetrahydrofuran |

The compounds were named using Nomenclator (v. 3.0 & v. 5.0) from CmemInovation Software, Inc. and ACD/Name v. 4.53.

The various aryl diamine starting materials used to synthesize benzimidazole acetates may be obtained from commercial sources, prepared by methods know to one of skill in the art, or prepared by the following general Methods 1-15.

Method 1

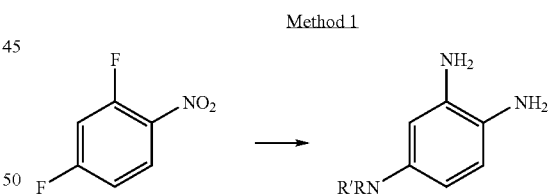

2,4-Difluoronitrobenzene (1.0 eq) was placed in a dry round-bottomed flask equipped with a dry ice condenser charged with acetone and dry ice. Ammonia was condensed into the flask and the resulting solution was stirred at reflux for 7 hours. A yellow precipitate formed within 1 hour. After 7 hours, the condenser was removed and the liquid ammonia was allowed to evaporate over several hours. The crude product was purified by flash chromatography on silica gel (85:15 hexanes:ethyl acetate, product at $R_f$=0.32, contaminant at $R_f$=0.51); GC/MS m/z 156.1 (M+), $R_t$11.16 minutes.

The resulting 5-fluoro-2-nitrophenylamine (1.0 eq) and an amine (1.1 eq) e.g. N-methyl piperazine, were dissolved in NMP and triethylamine (2.0 eq) was added. The reaction mixture was heated at 100° C. for 3 hours. The solution was then cooled to room temperature and diluted with water. The resulting precipitate was filtered and dried under vacuum to provide the 2-nitro-diamino product. Alternatively, the same product may be obtained from commercially available 5-chloro-2-nitrophenylamine under identical conditions except heating at 130° C. for 1-2 days. In some examples, the displacement on either 5-fluoro-2-nitrophenylamine or 5-chloro-2-nitrophenylamine can be conducted in neat amine (5 eq) at 100° C. or 130° C., respectively. The product is isolated in an identical manner. LC/MS m/z 237.1 (MH+), $R_t$ 1.304 minutes.

The nitroamine (1.0 eq) and 10% Pd/C (0.1 eq) was suspended in anhydrous ethanol at room temperature. The reaction flask was evacuated and subsequently filled with $H_2$. The resulting mixture was then stirred under a hydrogen atmosphere overnight. The resulting solution was filtered through Celite and concentrated under vacuum to provide the crude product which was used without further purification.

Method 2

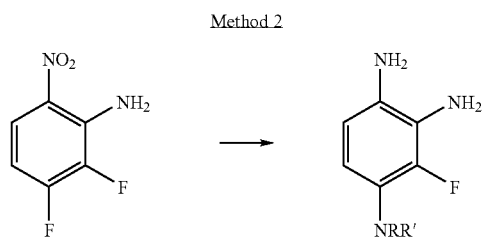

A round-bottom flask was charged with 2,3-difluoro-6-nitrophenylamine (1 eq) and enough NMP to make a viscous slurry. An amine (5 eq), e.g. N-methyl piperazine, was added and the solution was heated at 100° C. After 2 hours, the solution was cooled and poured into water. A bright yellow solid formed which was filtered and dried. The nitroamine was reduced as in Method 1 to provide the crude product which was used without further purification. LC/MS m/z 225.1 (MH+), $R_t$ 0.335 minutes.

Method 3

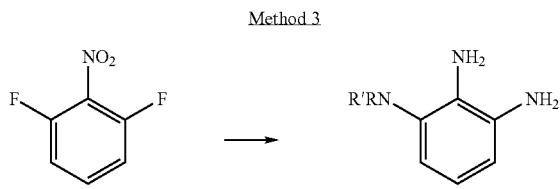

To a 0.1 M DMF solution of 1,3-difluoro-2-nitrobenzene was added $Et_3N$ (2 eq) followed by an amine (1 eq), e.g. morpholine. The mixture was stirred for 18 hours and then diluted with water and extracted with ethyl acetate. LC/MS m/z 227.2 (MH+), $R_t$ 2.522 minutes. The combined organic layers were dried over $MgSO_4$, filtered, and concentrated. Ammonia was condensed into a bomb containing the crude product. The bomb was sealed and heated to 100° C. (over 400 psi). After 72 hours the bomb was allowed to cool and the ammonia was evaporated to provide a reddish solid. The nitroamine was reduced as in Method 1 to provide the crude product which was used without further purification. LC/MS m/z 194.1 (MH+), $R_t$ 1.199 minutes.

Method 4

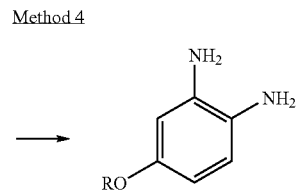

To a stirred NMP solution containing NaH (1.3 eq) was added an alcohol (1.0 eq), e.g. 2-methyloxyethanol. The resulting mixture was then stirred for 30 minutes. A slurry of 5-fluoro-2-nitrophenylamine in NMP was then added slowly. The mixture was then heated to 100° C. After 2 hours, the reaction mixture was cooled and water was added. The mixture was then filtered and the captured solid was washed with water and purified by silica gel chromatography (1:1 ethyl acetate:hexane). LC/MS m/z 213.2 (MH+), $R_t$ 2.24 minutes. The nitroamine was reduced as in Method 1 to provide the crude product which was used without further purification. LC/MS m/z 183.1 (MH+), $R_t$ 0.984 minutes.

Method 5

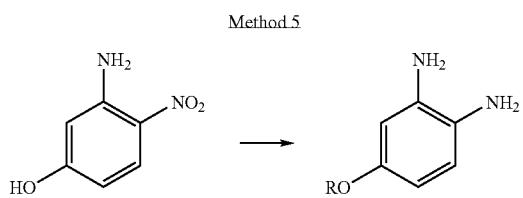

Diisopropyl azodicarboxylate (1.1 eq) was added dropwise to a stirred solution of 4-amino-3-nitrophenol (1.0 eq), triphenylphosphine (1.1 eq), and an alcohol, e.g. N-(2-hydroxyethyl)morpholine (1.0 eq), in tetrahydrofuran at 0° C. The mixture was allowed to warm to room temperature and stirred for 18 hours. The solvent was evaporated, and the product was purified by silica gel chromatography (98:2 $CH_2Cl_2$:methanol) to yield 4-(2-morpholin-4-ylethoxy)-2-nitrophenylamine as a dark reddish-brown oil. LC/MS m/z 268.0 (MH+), $R_t$ 1.01 minutes. The nitroamine was reduced as in Method 1 to give the crude product which was used without further purification. LC/MS m/z 238.3 (MH+), $R_t$ 0.295 minutes.

Method 6

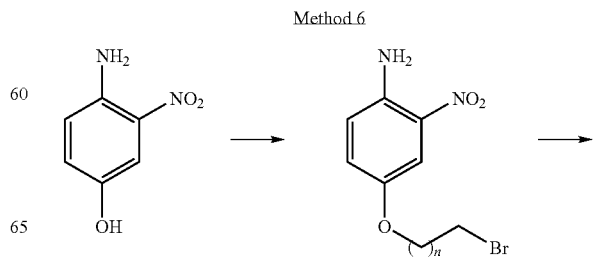

-continued

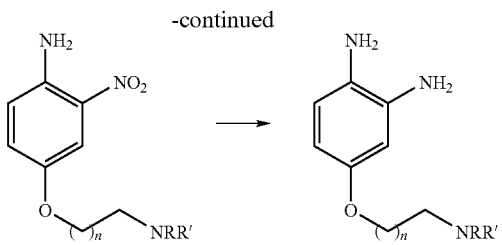

To a flask charged with 4-amino-3-nitrophenol (1 eq), K₂CO₃ (2 eq), and 2-butanone was added an alkyl dibromide, e.g. 1,3-dibromopropane (1.5 eq). The resulting mixture was then heated at 80° C. for 18 hours. After cooling, the mixture was filtered, concentrated, and diluted with water. The solution was then extracted with CH₂Cl₂ (3×) and the combined organic layers were concentrated to give a solid that was then washed with pentane. LCMS m/z 275.1 (MH+), $R_t$ 2.74 minutes.

An acetonitrile solution of the bromide prepared above, an amine, e.g. pyrrolidine (5 eq), Cs₂CO₃ (2 eq) and Bu₄NI (0.1 eq) was heated at 70° C. for 48 hours. The reaction mixture was cooled, filtered, and concentrated. The residue was dissolved in CH₂Cl₂, washed with water, and concentrated to give the desired nitroamine, 2-nitro-4-(3-pyrrolidin-1-ylpropoxy)phenylamine. LCMS m/z 266.2 (MH+), $R_t$ 1.51 minutes. The nitroamine was reduced as in Method 1 to provide the crude product which was used without further purification.

Method 7

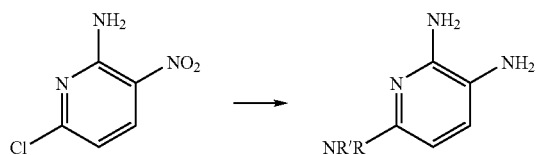

To a suspension of 6-chloro-3-nitropyridin-2-amine (1 eq) in acetonitrile was added an amine, e.g. morpholine (4 eq). The resulting reaction mixture was stirred at 70° C. for 5 hours. The solvent was evaporated under reduced pressure, and the residue triturated with ether to provide the desired compound as a bright yellow powder. LC/MS m/z 225.0 (MH+), $R_t$ 1.79 minutes. The nitroamine was reduced as in Method 1 to provide the crude product which was used without further purification.

Method 8:

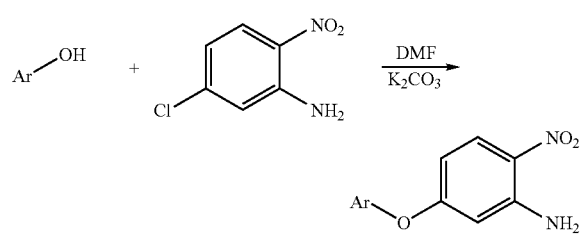

A phenol (1 equivalent) and 5-chloro-2-nitro aniline (1 equivalent) were dissolved in DMF, and solid K₂CO₃ (2 equivalents) was added in one portion. The reaction mixture was heated at 120° C. overnight. The reaction mixture was cooled to room temperature, most of the DMF was distilled off, and water was added to the residue to obtain a precipitate. The solid was dried and purified by chromatography on silicagel (2-10% MeOH/CH₂Cl₂) to afford the desired product. The nitroamine was reduced as in method 1 to give the crude product that was used without further purification.

Method 9

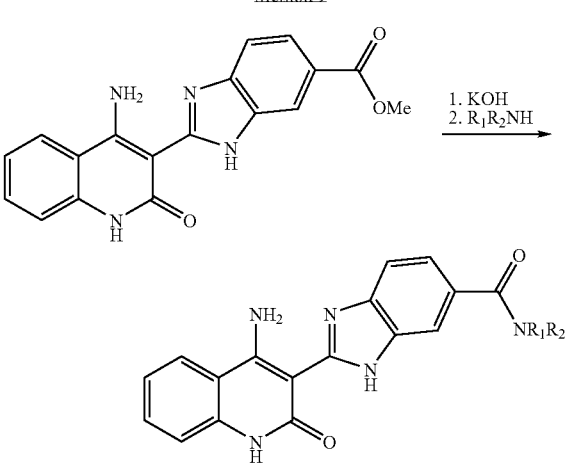

Furthermore, the introduction of substituents on the benzimidazole ring need not be limited to the early stages of the synthesis and may arise after formation of the quinolinone ring. For example, the crude methyl ester shown in the figure above was dissolved in a 1:1 mixture of EtOH and 30% aqueous KOH and stirred overnight at 70° C. The reaction mixture was then cooled and acidified with 1N HCl to give a precipitate. The solid was filtered, washed with water and dried to obtain 2-(4-amino-2-oxo-1,2-dihydroquinolin-3-yl)-1H-benzimidazole-6-carboxylic acid 2-(4-amino-2-oxo-3-hydroquinolyl)benzimidazole-6-carboxylic acid as a brown solid. LC/MS m/z: 321.1 (MH+), $R_t$ 2.26 minutes.

A mixture of 2-(4-amino-2-oxo-1,2-dihydroquinolin-3-yl)-1H-benzimidazole-6-carboxylic acid (1 eq) the amine (1 eq), EDC (1-(3-dimethylaminopropyl)-3-ethylcarbodiimide hydrochloride, 1.2 eq), HOAT (1-hydroxy-7-azabenzotriazole, 1.2 eq) and triethylamine (2.5 eq) in DMF, was stirred at 23° C. for 20 h. The reaction mixture was partitioned between water and ethyl acetate. The combined organic layers were dried (Na₂SO₄) and concentrated. Water was added and the precipitate thus formed was filtered off and dried to afford the desired product.

The various 2-amino benzoic acid starting materials used to synthesize isatoic anhydrides may be obtained from commercial sources, prepared by methods know to one of skill in the art, or prepared by the following general Methods 10-11. General isatoic anhydride synthesis methods are described in *J. Med. Chem.* 1981, 24 (6), 735 and *J. Heterocycl. Chem.* 1975, 12(3), 565.

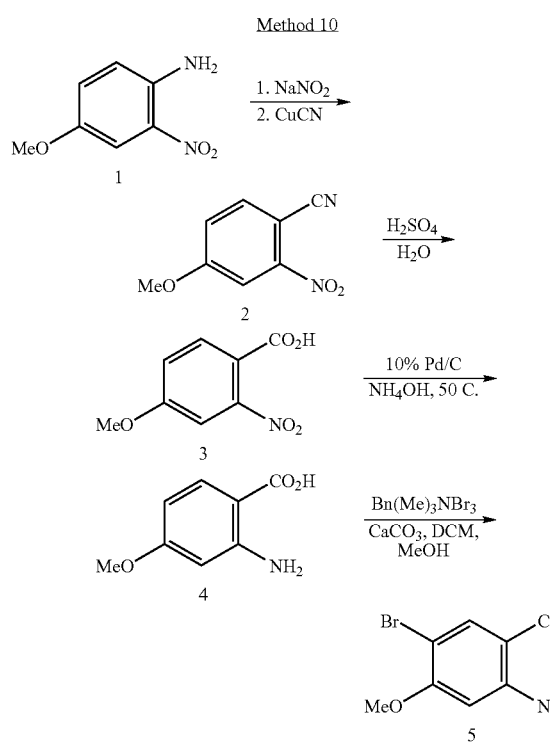

Compounds 1-3 were made using similar procedures as found in U.S. Pat. No. 4,287,341. Compound 3 was reduced using standard hydrogenation conditions of 10% Pd/C in NH$_4$OH at 50° C. over 48 hours. The product was precipitated by neutralizing with glacial acetic acid, filtering, and washing with water and ether. Yields were about 50%. Compound 5 was prepared in a manner similar to that disclosed in U.S. Pat. No. 5,716,993.

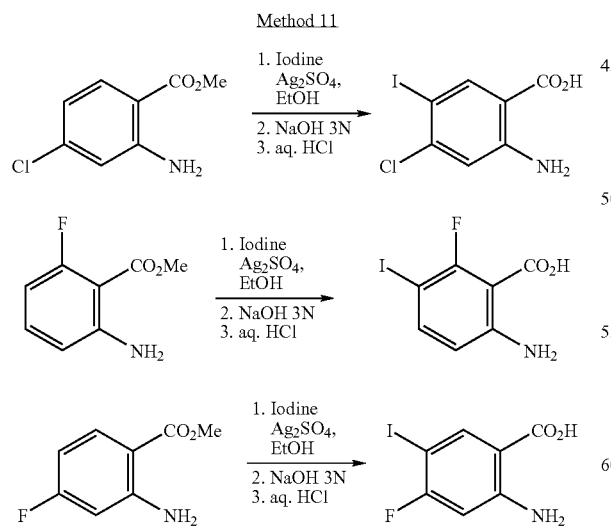

Iodination of aniline containing compounds: Iodination was done by a similar procedure as in *J. Med. Chem.* 2001, 44, 6, 917-922. The anthranilic ester in EtOH was added to a mixture of silver sulfate (1 equivalent) and I$_2$ (1 equivalent). The reaction was typically done after 3 hours at room temperature. The reaction was filtered through celite and concentrated. The residue was taken up in EtOAc and washed with aqueous saturated NaHCO$_3$ (3×), water (3×), brine (1×), dried (MgSO$_4$), filtered, and concentrated. The crude product (~5 g) was dissolved in MeOH (60-100 ml), NaOH 6N (25 ml), and water (250 ml). The reactions were typically done after heating at 70-80° C. for 4 hours. The reaction mixture was extracted with EtOAc (2×), neutralized with aqueous HCl, filtered to collect the solids, and the solid products were washed with water. The products were dried in vacuo.

In various instances, substitutions on the quinolinone ring may also be introduced after coupling as shown in the general methods 12-15.

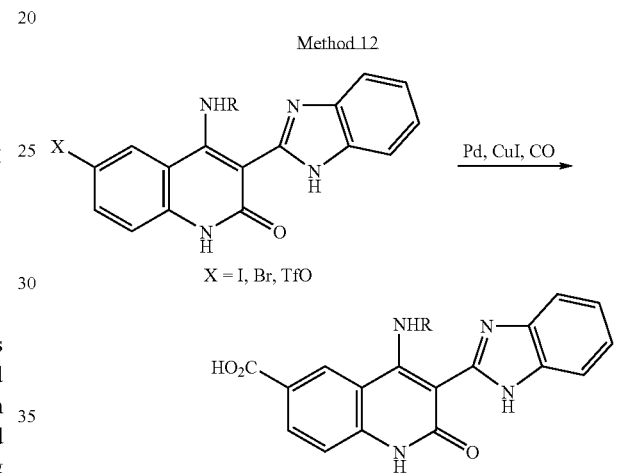

Conversion of the C-6 or C-7 halides to an acid group was accomplished using procedures in the following references— Koga, H.; et al., *Tet. Let.,* 1995, 36, 1, 87-90 and Fukuyama, T.; et al., *J. Am. Chem. Soc.,* 1994, 116, 3125-3126.

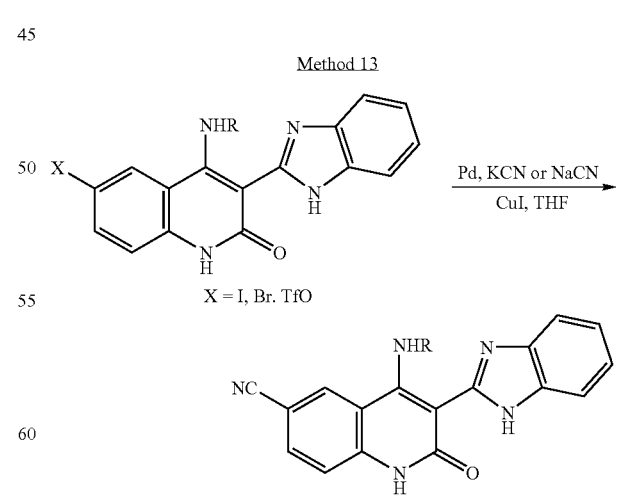

Conversion of the C-6 or C-7 halides to a cyano group was accomplished using procedures in the following reference— Anderson, B. A.; et al., *J. Org. Chem.,* 1998, 63, 8224-828.

Method 14

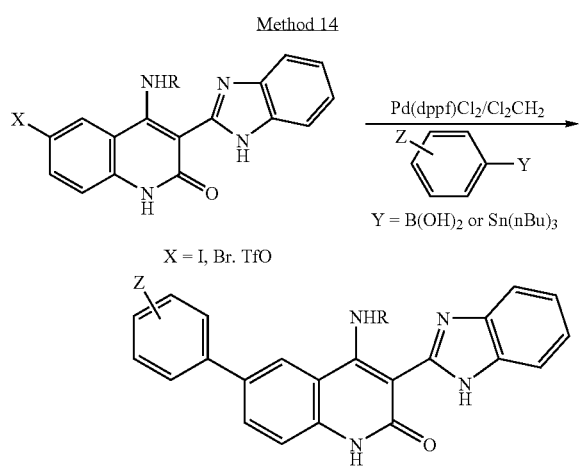

Conversion of the C-6 or C-7 halides to an aryl group was accomplished using standard Suzuki or Stille procedures such as described below.

Suzuki Method: To a 1 dram (4 ml) vial was added sequentially the quinolone (1 equivalent), boronic acid (1.2-1.5 equivalents), Pd(dppf)Cl₂, Cl₂CH₂ (0.2 equivalents), DMF (0.5-1 ml) and TEA (4 equivalents). The reaction was flushed with argon, capped and heated at 85° C. for 12 hours. Once done, the reaction is cooled to room temperature, and filtered with a syringe filter disk. The clear solution is then neutralized with TFA (a couple of drops) and injected directly onto a preparative HPLC. The products are lyophilized to dryness.

Stille Method: To a 1 dram (4 ml) vial was added sequentially the quinolone (1 equivalent), tin reagent (1.8 equivalent), Pd(dppf)Cl₂. Cl₂CH₂ (0.2 equivalents), and DMF (0.5-1 ml). The reaction was flushed with argon, capped and heated at 60-85° C. for 4 hours. Once done, the reaction is cooled to room temperature, and filtered with a syringe filter disk. The clear solution is then neutralized with TFA (a couple of drops) and injected directly onto a preparative HPLC. The products are lyophilized to dryness.

Method 15

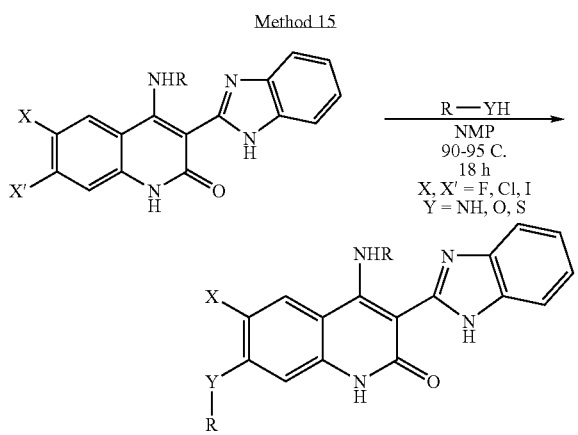

A dihaloquinolone such as a difluoroquinolone (12-15 mg) was placed in a 1 dram (2 ml) vial. NMP (dry and pre-purged with argon for 5 minutes) was added to the vial (0.5 ml). The amine reagent (40-50 mg) was added next. If the amine was an HCl salt, the reaction was neutralized with TEA (~1.2-1.5 equivalents). The reaction was purged again with argon for about 5 seconds, and immediately capped. The reaction was typically heated in a heating block at 90-95° C. for 18 hours. The reaction was followed by HPLC or LCMS. After taking samples for HPLC, the vial was purged with argon again and capped. Some coupling partners took 24 or 48 hours to reach completion. Less nucleophilic amines like pyrrole required the addition of a strong base to reach completion. In these cases, cesium carbonate (2 equivalents based on the amine used) was added to the reaction. Once done, the reaction was cooled to room temperature, and filtered with a syringe filter disk. The clear solution was then neutralized with TFA (a couple of drops) and injected directly onto a preparative HPLC. The products were lyophilized to dryness.

Example 1

Ethyl 2-benzimidazol-2-ylacetate

A solution of 1,2-phenylenediamine (1.0 eq) and ethyl 3-ethoxy-3-iminopropanoate hydrochloride (1.3 eq) in ethanol was stirred at 90° C. overnight. The reaction was cooled to room temperature and the solvent was removed in vacuo. Water and $CH_2Cl_2$ were added to the residue. The organic layer was separated, dried over $Na_2SO_4$ and the solvent removed. The solid recovered was used without purification. LC/MS m/z 205.2 (MH+), $R_t$ 1.44 minutes.

5-(4-Methylpiperazinyl)-2-nitrobenzenecarbonitrile

5-Fluoro-2-nitrobenzenecarbonitrile (1.02 eq) and N-methylpiperazine (1.0 eq) were dissolved in NMP. Triethylamine (2.1 eq) was added, and the resulting solution heated at 100° C. for 1 hour. The solution was cooled to room temperature and poured into $H_2O$. A precipitate formed which was filtered to yield the desired product as a green solid. LC/MS m/z 247.3 (MH+), $R_t$ 1.46 minutes.

2-Amino-5-(4-methylpiperazinyl)benzenecarbonitrile 5-(4-Methylpiperazinyl)-2-nitrobenzenecarbonitrile (1.0 eq) was dissolved in EtOAc. The flask was purged with nitrogen, and 10% Pd/C (0.1 eq) was added. The flask was evacuated and purged with $H_2$ three times. The resulting mixture was stirred for three days at room temperature. The mixture was filtered through Celite and the filter pad was washed with EtOAc. The solvent was removed in vacuo to give a yellow solid which was purified by silica gel chromatography (5:1: 95 MeOH:$Et_3$N:EtOAc) to give the desired product as a yellow solid. LC/MS m/z 217.3 (MH+), $R_t$ 0.95 minutes.

Method A

4-Amino-3-benzimidazol-2-yl-6-(4-methylpiperazinyl)hydroquinolin-2-one

Ethyl 2-benzimidazol-2-ylacetate (1.1 eq) and 2-amino-5-(4-methylpiperazinyl)benzenecarbonitrile (1.0 eq) were dissolved in 1,2-dichloroethane, and then $SnCl_4$ (11 eq) was added. The mixture was heated at reflux overnight. Upon cooling, the mixture was concentrated in vacuo. NaOH (3 M) was added to the solid, and the mixture heated at 80° C. for 0.5 hours. The solid was filtered and washed sequentially with $H_2O$, $CH_2Cl_2$, and acetone. LC/MS indicated that the product was present in the acetone layer and the solid. These fractions were combined and purified by silica gel chromatography (5-10% MeOH in $CH_2Cl_2$ with 1% $Et_3$N) to give the desired product. LC/MS m/z 375.4 (MH+), $R_t$ 1.65 minutes.

Example 2

6-Amino-2-(2-morpholin-4-ylethoxy)benzenecarbonitrile 4-(Hydroxyethyl)morpholine (1.02 eq) was added to NaH (1.2 eq) in NMP. After 10 minutes, 6-amino-2-fluorobenzenecarbonitrile (1.0 eq) was added in NMP. The resulting mixture was heated at 100° C. for 1 hour. The mixture was then cooled and poured into $H_2O$. The aqueous layer was extracted with EtOAc. The combined organic layers were washed with brine, dried over $Na_2SO_4$, filtered, and concentrated in vacuo to a yield a brown gum. The crude material was purified by silica gel chromatography (5:1:95 MeOH:$Et_3$N:EtOAc) to give the desired product. LC/MS m/z 248.3 (MH+), $R_t$ 1.26 minutes.

4-Amino-3-benzimidazol-2-yl-5-(2-morpholin-4-ylethoxy)hydroquinolin-2-one

The title compound was synthesized as described in Example 1, Method A using 6-amino-2-(2-morpholin-4-ylethoxy)benzenecarbonitrile. LC/MS m/z 406.4 (MH+), $R_t$ 1.67 minutes.

Example 3

4-(2-Morpholin-4-ylethoxy)-2-nitrophenylamine

Diisopropyl azodicarboxylate (1.1 eq) was added dropwise to a stirred solution of 4-amino-3-nitrophenol (1.0 eq), triphenylphosphine (1.1 eq), and N-(2-hydroxyethyl)morpholine (1.0 eq), in THF at 0° C. The mixture was allowed to warm to room temperature and left to stir for 18 hours. The solvent was evaporated and the product was purified by silica gel chromatography (98:2 $CH_2Cl_2$:MeOH) to yield a dark reddish-brown oil. LC/MS m/z 268.0 (MH+), $R_t$ 1.01 minutes.

4-(2-Morpholin-4-ylethoxy)benzene-1,2-diamine

To a solution 4-(2-morpholin-4-ylethoxy)-2-nitrophenylamine (1.0 eq) in EtOH was added Pd/C (0.1 eq). The reaction vessel was repeatedly purged with nitrogen, then stirred under a hydrogen atmosphere (1 atm) for 18 hours. The product was filtered through a Celite plug, and the plug washed with EtOH. The diamine was used without purification. LC/MS m/z 238.3 (MH+), $R_t$ 0.295 minutes.

Ethyl 2-[5-(2-morpholin-4-ylethoxy)benzimidazol-2-yl]acetate

The title compound was synthesized as described in Example 1 using 4-(2-morpholin-4-ylethoxy)benzene-1,2-diamine. The organic layer was concentrated and the residue was purified by silica gel chromatography (10:1:2 $CH_2Cl_2$:MeOH:EtOAc) to yield a dark reddish brown oil. LC/MS m/z 334.4 (MH+) $R_t$ 1.08 minutes.

4-Amino-3-[5-(2-morpholin-4-ylethoxy)benzimidazol-2-yl]-6-nitrohydroquinolin-2-one The title compound was synthesized as described in Example 1, Method A using ethyl 2-[5-(2-morpholin-4-ylethoxy)benzimidazol-2-yl]acetate and 5-nitroanthranilonitrile. The crude product was purified by silica gel chromatography (5-10% MeOH in $CH_2Cl_2$ with 1% $Et_3$N) to give the desired product. LC/MS m/z 451.2 (MH+), $R_t$ 1.89 minutes.

Example 4

4-Amino-5-(2-morpholin-4-ylethoxy)-3-[5-(2-morpholin-4-ylethoxy)-benzimidazol-2-yl]hydroquinolin-2-one The title compound was synthesized as described in Example 1, Method A using ethyl 2-[5-(2-morpholin-4-ylethoxy)benzimidazol-2-yl]acetate and 6-amino-2-(2-morpholin-4-ylethoxy)benzenecarbonitrile. LC/MS m/z 535.4 (MH+), $R_t$ 1.44 minutes.

Example 5

2-[(Ethoxycarbonyl)methyl]benzimidazole-5-carboxylic acid

The title compound was synthesized as described in Example 1 using 3,4-diaminobenzoic acid. The crude material was purified by silica gel chromatography (5:95 MeOH:$CH_2Cl_2$) to afford the desired product as a white to off-white solid. LC/MS m/z 249.1 (MH+), $R_t$ 1.35 minutes.

Ethyl 2-[5-(N,N-dimethylcarbamoyl)benzimidazol-2-yl]acetate

2-[(Ethoxycarbonyl)methyl]benzimidazole-5-carboxylic acid (1.0 eq) was dissolved in THF. HBTU (1.1 eq) and diisopropylethylamine (2.0 eq) were added, followed by dimethylamine (2.0 M in THF, 1.1 eq). The reaction was stirred at room temperature overnight then concentrated and the resulting residue was purified by silica gel chromatography (5:95 MeOH:$CH_2Cl_2$) to afford the desired compound. LC/MS m/z 276.2 (MH+), $R_t$ 1.18 minutes.

[2-(4-amino-2-oxo(3-hydroquinolyl))benzimidazol-5-yl]-N,N-dimethylcarboxamide The title compound was synthesized as described in Example 1, Method A using ethyl 2-[5-(N,N-dimethylcarbamoyl)benzimidazol-2-yl]acetate and anthranilonitrile. The resulting solid was collected by filtration and washed with water followed by acetone to afford the desired product as a white solid. LC/MS m/z 348.3 (MH+), $R_t$ 1.87 minutes.

Example 6

4-Amino-3-[5-(morpholin-4-ylcarbonyl)benzimidazol-2-yl]hydroquinolin-2-one

2-[(Ethoxycarbonyl)methyl]benzimidazole-5-carboxylic acid (1.0 eq) was dissolved in THF. HBTU (1.1 eq) and diisopropylethylamine (2.0 eq) were added, followed by morpholine (1.1 eq). The reaction was stirred at room temperature for 3 days then concentrated and purified by silica gel chromatography (5-10% methanol/dichloromethane). The product-containing fractions were concentrated and dissolved in anhydrous 1,2-dichloroethane. Anthranilonitrile (1.0 eq) was added followed by $SnCl_4$ (5.0 eq) and the reaction was heated at 90° C. overnight. The reaction mixture was concentrated and the resulting residue was re-dissolved in NaOH (2 M) and heated at 90° C. for 4 hours. After cooling to room temperature, the resulting solid was collected and washed with water followed by acetone to afford the desired product. LC/MS m/z 390.2 (MH+), $R_t$ 1.95 minutes.

Example 7

4-Bromobenzene-1,2-diamine

A solution of 4-bromo-2-nitroaniline (1.0 eq) and $SnCl_2$ (2.2 eq) in EtOH was heated at reflux for 3 hours. After this time, the solution was poured onto ice, brought to pH 10 with 2M NaOH and extracted with $Et_2O$. The combined organic layers were dried over $MgSO_4$ and concentrated. The resulting brown oil was purified by silica gel chromatography (0-50% EtOAc:hexanes) to provide a light yellow solid. LC/MS m/z 187.1 (MH+), $R_t$ 1.33 minutes.

2-Nitro-4-(2-thienyl)phenylamine

4-Bromo-2-nitroaniline (1.0 eq) and $Na_2CO_3$ (2.0 eq) were dissolved in $DMF/H_2O$ (5:1) at room temperature. Nitrogen was bubbled through the reaction mixture for 5 minutes and $PdCl_2(dppf)_2$ (0.1 eq) was added. After stirring at 23° C. for approximately 10 minutes, 2-thiopeneboronic acid (1.1 eq) in DMF was added and the reaction was heated at 90° C. for 12 hours. After this time, the solution was concentrated and partitioned between EtOAc and $H_2O$. The layers were separated and the aqueous layer was extracted with EtOAc. The combined organic layers were dried over $MgSO_4$ and concentrated under reduced pressure. The resulting black residue was purified by silica gel chromatography (0-20% EtOAc: hexanes) to yield an orange solid. LC/MS m/z 221.1 (MH+), $R_t$ 2.67 minutes.

Ethyl 2-[5-(2-thienyl)benzimidazol-2-yl]acetate

2-Nitro4-(2-thienyl)phenylamine (1.0 eq) and 10% Pd/C (0.1 eq) were suspended in anhydrous EtOH at room temperature. The reaction flask was evacuated and subsequently filled with $H_2$. The resulting mixture was allowed to stir under a hydrogen atmosphere for 3 hours. Ethyl 3-ethoxy-3-iminopropanoate hydrochloride (2.0 eq) was then added and the resulting mixture was heated at reflux for 12 hours. After this time, the solution was filtered through a plug of Celite, concentrated, dissolved in 50 ml of 2N HCl and washed with $CH_2Cl_2$. The aqueous layer was brought to pH 12 with concentrated $NH_4OH$(aq) and extracted with $CH_2Cl_2$. The combined organic layers were dried with $MgSO_4$ and concentrated to yield a brown oil which was purified by silica gel chromatography (5:95 $MeOH:CH_2Cl_2$) to provide a yellow solid. LC/MS m/z 287.1 (MH+), $R_t$ 1.98 minutes.

4-Amino-3-[5-(2-thienyl)benzimidazol-2-yl]hydroquinolin-2-one

The title compound was synthesized as described in Example 1, Method A using ethyl 2-[5-(2-thienyl)benzimidazol-2-yl]acetate and anthranilonitrile. LC/MS m/z 359.2 (MH+), $R_t$ 2.68 minutes.

Example 8

5-Fluoro-2-nitrophenylamine 2,4-Difluoronitrobenzene (1.0 eq) was placed in a dry round-bottomed flask equipped with a dry ice condenser charged with acetone/dry ice. Ammonia was condensed into the flask and the resulting solution was stirred at reflux for 7 hours. A yellow precipitate was formed within 1 hours. After 7 hours, the condenser was removed and the liquid ammonia was allowed to evaporate over several hours. The crude product was purified by flash chromatography on silica gel (85:15 hexanes:EtOAc, product at $R_f$=0.32, contaminant at $R_f$=0.51). GC/MS m/z 156.1 (M+), $R_t$ 11.16 minutes.

2-Nitro-5-[1-(1,2,4-triazolyl)]phenylamine

5-Fluoro-2-nitrophenylamine (1.0 eq), 1H-1,2,4-triazole (3.0 eq) and NaH (3.0 eq) in NMP were heated at 100° C. for 1 hour. The solution was cooled to room temperature and slowly poured onto ice water. The resulting precipitate was filtered and dried under vacuum to yield the desired product. The resulting solid was recrystallized from EtOH to afford pure product as a bright yellow solid. LC/MS m/z 206.2 (MH+), $R_t$ 1.88 minutes.

Ethyl 2-{5-[1-(1,2,4-triazolyl)]benzimidazol-2-yl}acetate

The title compound was synthesized as described in Example 7 using 2-nitro-5-[1-(1,2,4-triazolyl)]phenylamine. LC/MS m/z 272.1 (MH+), $R_t$ 1.19 minutes.

4-Amino-3-{5-[1-(1,2,4-triazolyl)]benzimidazol-2-yl}hydroquinolin-2-one

The title compound was synthesized as described in Example 1, Method A using ethyl 2-{5-[1-(1,2,4-triazolyl)]benzimidazol-2-yl}acetate and anthranilonitrile. The crude solid was collected and purified by silica gel chromatography (92:7:1 $CH_2Cl_2$:MeOH:$Et_3N$). LC/MS m/z 344.3 (MH+), $R_t$ 2.01 minutes.

Example 9

Method B

N-(4-Chloro-2-cyanophenyl)-2-(5-morpholin-4-yl-benzimidazol-2-yl)acetamide

LiHMDS (2.5 eq) was added to ethyl 2-[5-(2-morpholin-4-ylethoxy)benzimidazol-2-yl]acetate (1.0 eq) in THF at −78° C. After 1 hour, 2-amino-5-chlorobenzenecarbonitrile (0.82 eq) in THF was added. The reaction was allowed to warm to 23° C. and stirred overnight. The resulting mixture was quenched with $NH_4Cl$ (aqueous saturated solution) and extracted with EtOAc. The combined organic layers were washed with $H_2O$ and brine, dried over $Na_2SO_4$, filtered and concentrated in vacuo to yield a brown solid. The crude material was purified by silica gel chromatography (5:1 EtOAc: hexane) to give the desired product. LC/MS m/z 396.1 (MH+), $R_t$ 1.79 minutes.

4-Amino-6-chloro-3-(5-morpholin-4-ylbenzimidazol-2-yl)hydroquinolin-2-one

N-(4-chloro-2-cyanophenyl)-2-(5-morpholin-4-ylbenzimidazol-2-yl)acetamide (1.0 eq) was heated in NaOMe (0.5 M in MeOH, 18 eq) at 70° C. for 2 hours. The resulting mixture was cooled, and the resulting solid was filtered and washed with water to give the desired product. LC/MS m/z 396.4 (MH+), $R_t$ 2.13 minutes.

Example 10

2-Nitro-5-piperidylphenylamine

The title compound was synthesized as described in Example 8 using piperidine (3.0 eq, excess acts as base in place of NaH). The desired product was obtained as a yellow, crystalline solid. LC/MS m/z 222.2 (MH+), $R_t$ 2.53 minutes.

Ethyl 2-(5-piperidylbenzimidazol-2-yl)acetate

The title compound was synthesized as described in Example 7 using 2-nitro-5-piperidylphenylamine. The desired product was obtained as a yellow oil. LC/MS m/z 288.3 (MH+), $R_t$ 1.31 minutes.

4-amino-3-(5-piperidylbenzimidazol-2-yl)hydroquinolin-2-one

The title compound was synthesized as described in Example 9, Method B using ethyl 2-(5-piperidylbenzimidazol-2-yl)acetate and anthranilonitrile. The acyclic amide was used crude in the NaOMe cyclization step. The desired product was obtained following purification by silica gel chromatography (96.5:3.0:0.5 $CH_2Cl_2$:MeOH:$Et_3N$, $R_f$ 0.2). LC/MS m/z 360.4 (MH+), $R_t$ 1.83 minutes.

Example 11

[1-(3-Amino-4-nitrophenyl)pyrrolidin-3-yl]dimethylamine

The title compound was synthesized as described in Example 8 using 3-(dimethylamino)pyrrolidine (3.0 eq, excess amine was used as the base in place of NaH). LC/MS m/z 251.3 (MH+), $R_t$ 1.25 minutes.

Ethyl 2-{5-[3-(dimethylamino)pyrrolidinyl]benzimidazol-2-yl}acetate

The title compound was synthesized as described in Example 7 using [1-(3-amino-4-nitrophenyl)pyrrolidin-3-yl]dimethylamine. The desired product was obtained as a yellow oil. LC/MS m/z 317.4 (MH+), $R_t$ 1.36 minutes.

2-{5-[3-(Dimethylamino)pyrrolidinyl]benzimidazol-2-yl}-N-(4-chloro-2-cyanophenyl)acetamide The title compound was synthesized as described in Example 9, Method B using ethyl 2-{5-[3-(dimethylamino)pyrrolidinyl]benzimidazol-2-yl}acetate. LC/MS m/z 423.4 (MH+), $R_t$ 1.67 minutes.

4-Amino-3-{5-[3-(dimethylamino)pyrrolidinyl]benzimidazol-2-yl}-6-chlorohydroquinolin-2-one The title compound was synthesized as described in Example 9, Method B using 2-{5-[3-(dimethylamino)pyrrolidinyl]benzimidazol-2-yl}-N-(4-chloro-2-cyanophenyl)acetamide. LC/MS m/z 423.4 (MH+), $R_t$ 1.71 minutes.

Example 12

Ethyl 2-[5-(dimethylamino)benzimidazol-2-yl]acetate

The title compound was synthesized as described in Example 7 using (3-amino-4-nitrophenyl)dimethylamine. The resulting tan film was purified by silica gel chromatography (5:1:94 MeOH:$Et_3N$:$CH_2Cl_2$) to give the desired product. LC/MS 248.3 m/z (MH+), $R_t$ 1.24 minutes.

2-[5-(Dimethylamino)benzimidazol-2-yl]-N-(2-cyanophenyl)acetamide

The title compound was synthesized as described in Example 9, Method B using ethyl 2-[5-(dimethylamino)benzimidazol-2-yl]acetate and anthranilonitrile. LC/MS m/z 320.2 (MH+), $R_t$ 1.68 minutes.

4-Amino-3-[5-(dimethylamino)benzimidazol-2-yl]hydroquinolin-2-one

The title compound was synthesized as described in Example 9, Method B using 2-[5-(dimethylamino)benzimidazol-2-yl]-N-(2-cyanophenyl)acetamide. LC/MS m/z 320.2 (MH+), $R_t$ 1.72 minutes.

Example 13

Ethyl 2-(5-cyanobenzimidazol-2-yl)acetate

The title compound was synthesized as described in Example 7 using 4-amino-3-nitro-benzonitrile. LC/MS m/z 230.2 (MH+), $R_t$ 1.29 minutes.

2-(4-Amino-2-oxo-3-hydroquinolyl)benzimidazole-5-carbonitrile

The title compound was synthesized as described in Example 9, Method B using ethyl 2-(5-cyanobenzimidazol-2-yl)acetate and anthranilonitrile (no acyclic amide observed so the NaOMe step was not needed). LC/MS m/z 302.3 (MH+), $R_t$ 2.62 minutes.

Example 14

2-(4-Amino-2-oxo-3-hydroquinolyl)benzimidazole-5-carboxamidine 2-(4-Amino-2-oxo-3-hydroquinolyl)benzimidazole-5-carbonitrile (1.0 eq) in EtOH was placed into a glass bomb, cooled to 0° C. and HCl (g) was bubbled through for 15 minutes. The bomb was then sealed, brought to room temperature and stirred overnight. The solvent was removed in vacuo. The residue was dissolved in EtOH in a glass bomb and cooled to 0° C. $NH_3$ (g) was bubbled through for 15 minutes and the bomb was sealed and heated to 80° C. for 5 hours. The solvent was removed in vacuo and the crude product was purified by reversed-phase HPLC. LC/MS m/z 319.2 (MH+), $R_t$ 1.70 minutes.

Example 15

4-Amino-3-[5-(2-morpholin-4-ylethoxy)-benzimidazol-2-yl]hydroquinolin-2-one The title compound was synthesized as described in Example 9, Method B using anthranilonitrile. The crude acyclic amide was used without purification in the NaOMe cyclization step. The crude final product was purified by reversed-phase HPLC (DMSO/5% TFA). LC/MS m/z 406.4 (MH+), $R_t$ 1.56 minutes.

Example 16

5-Morpholin-4-yl-2-nitrophenylamine

The title compound was synthesized as described in Example 8 using morpholine (3.0 eq, excess amine was used as the base in place of NaH). LC/MS m/z 224.1 (MH+), $R_t$ 1.89 minutes.

Ethyl 2-(5-morpholin-4-ylbenzimidazol-2-yl)acetate

The title compound was synthesized as described in Example 7 using 5-morpholin-4-yl-2-nitrophenylamine. The crude yellow oil was purified by silica gel chromatography (89.5:10:0.5 $CH_2Cl_2$:MeOH:$Et_3N$) to yield the desired product as a yellow solid. LC/MS m/z 290.3 (MH+), $R_t$ 1.31 minutes.

Method C

4-Hydroxy-3-(5-morpholin-4-ylbenzimidazol-2-yl)-1-benzylhydroquinolin-2-one To a solution of ethyl 2-(5-morpholin-4-ylbenzimidazol-2-yl)acetate (1.0 eq) in anhydrous THF at −78° C. under an atmosphere of nitrogen was added LiHMDS (1 M in THF, 3.1 eq) and the solution was stirred for 1 hour. A solution of 1-benzylbenzo[d]1,3-oxazaperhydroine-2,4-dione (1.05 eq) in anhydrous THF was then added dropwise and the resulting solution was allowed to warm to 0° C. over 1 hour. The resulting mixture was quenched with a saturated aqueous solution of ammonium chloride and the organic layer was separated. The aqueous layer was extracted with $CH_2Cl_2$ (4 times). The combined organic layers were dried over $Na_2SO_4$, concentrated in vacuo, and the crude material was dissolved in toluene and heated at reflux for 16 hours. The toluene was removed in vacuo and the crude material was used without further purification. The product was obtained as a white solid. LC/MS m/z 453.1 (MH+), $R_t$ 2.91 minutes.

4-Hydroxy-3-(5-morpholin-4-ylbenzimidazol-2-yl) hydroquinolin-2-one

Crude 4-hydroxy-3-(5-morpholin-4-ylbenzimidazol-2-yl)-1-benzylhydroquinolin-2-one (1.0 eq) was dissolved in trifluoromethanesulfonic acid and heated at 40° C. for 16 hours. The resulting solution was diluted with water and neutralized with 6 N NaOH (aq), whereupon a yellow precipitate formed. The crude solid was isolated by centrifugation and purified by reversed-phase HPLC to produce the desired product as a bright yellow solid. LC/MS m/z 363.3 (MH+), $R_t$ 1.77 minutes.

Example 17

N-[1-(3-Amino-4-nitrophenyl)pyrrolidin-3-yl](tert-butoxy)carboxamide

The title compound was synthesized as described in Example 8 using 3-(tert-butoxycarbonylamino)pyrrolidine (1.01 eq) with diisopropylethylamine (2.0 eq) as the base (in place of NaH). The product was obtained as an orange, crystalline solid. LC/MS m/z 323.3 (MH+), $R_t$ 2.53 minutes.

Ethyl 2-(5-{3-[(tert-butoxy)carbonylamino] pyrrolidinyl}benzimidazol-2-yl)acetate The title compound was synthesized as described in Example 7 using N-[1-(3-amino-4-nitrophenyl)pyrrolidin-3-yl](tert-butoxy)carboxamide. The product was obtained as a yellow oil. LC/MS m/z 323.3 (MH+), $R_t$ 2.53 minutes.

3-[5-(3-aminopyrrolidinyl)benzimidazol-2-yl]-4-hydroxyhydroquinolin-2-one

The title compound was synthesized following the procedure described in Example 16, Method C using ethyl 2-(5-{3-[(tert-butoxy)carbonylamino]pyrrolidinyl}benzimidazol-2-yl)acetate. The product was obtained as a yellow solid following cleavage of the benzyl group (see procedure in Example 15). LC/MS m/e 362.3 (MH+), $R_t$ 1.55 minutes.

Example 18

(3-Amino-4-nitrophenyl)[2-(dimethylamino)ethyl] methylamine

The title compound was synthesized as described in Example 8 using 1,1,4-trimethylethylenediamine (1.01 eq) with diisopropylethylamine (2.0 eq) as the base (in place of NaH). The product was obtained as a bright yellow, crystalline solid. LC/MS m/z 239.3 (MH+), $R_t$ 1.29 minutes.

Ethyl 2-(5-{[2-(dimethylamino)ethyl] methylamino}benzimidazol-2-yl)acetate

The title compound was synthesized as described in Example 7 using (3-amino-4-nitrophenyl)[2-(dimethylamino)ethyl]methylamine. The desired product was obtained as a yellow oil. LC/MS m/z 305.2 (MH+), $R_t$ 1.17 minutes.

3-(5-{[2-(Dimethylamino)ethyl] methylamino}benzimidazol-2-yl)-4-hydroxy-1-benzylhydroquinolin-2-one The title compound was synthesized as described in Example 16, Method C using ethyl 2-(5-{[2-(dimethylamino)ethyl]methylamino}benzimidazol-2-yl)acetate. The product was obtained as a pale yellow solid. LC/MS m/z 468.4 (MH+), $R_t$ 2.26 minutes.

3-(5-{[2-(Dimethylamino)ethyl] methylamino}benzimidazol-2-yl)-4-hydroxyhydroquinolin-2-one The title compound was synthesized as described in Example 16, Method C using 3-(5-{[2-(dimethylamino)ethyl]methylamino}benzimidazol-2-yl)-4-hydroxy-1-benzylhydroquinolin-2-one. The crude material was purified by reversed-phase HPLC to yield the product as a yellow solid. LC/MS m/z 378.4 (MH+), $R_t$ 1.99 minutes.

Example 19

Method D

4-Chloro-3-(5-morpholin4-ylbenzimidazol-2-yl)-1-benzylhydroquinolin-2-one

A solution of 4-hydroxy-3-(5-morpholin-4-ylbenzimidazol-2-yl)-1-benzylhydroquinolin-2-one (1.0 eq) and POCl$_3$ in a dry, round-bottomed flask was heated at 80° C. for 2 hours. The excess POCl$_3$ was removed in vacuo and the crude material was quenched with water. The crude product was collected by filtration and purified by silica gel chromatography (1:9 MeOH: CH$_2$Cl$_2$). 4-Chloro-3-(5-morpholin-4-yl-benzimidazol-2-yl)-1-benzylhydroquinolin-2-one was isolated as a red solid. LC/MS m/z 471.4 (MH+), R$_t$ 2.35 minutes.

4-[(2-Methoxyethyl)amino]-3-(5-morpholin-4-ylbenzimidazol-2-yl)-1-benzylhydroquinolin-2-one A solution of 4-chloro-3-(5-morpholin4-ylbenzimidazol-2-yl)-1-benzylhydroquinolin-2-one (1.0 eq) and EtOH was treated with 2-methoxyethyl-amine (10 eq) at room temperature. The resulting solution was heated at reflux for 16 hours and then the solvent was removed in vacuo. The crude solid was sonicated in water, filtered, sonicated in hexanes, and filtered again. The crude product was used without further purification. LC/MS m/z 510.4 (MH+), R$_t$ 2.20 minutes.

4-[(2-Methoxyethyl)amino]-3-(5-morpholin-4-ylbenzimidazol-2-yl)hydroquinolin-2-one 4-[(2-methoxyethyl)amino]-3-(5-morpholin-4-ylbenzimidazol-2-yl)-1-benzylhydroquinolin-2-one was debenzylated using the procedure described in Example 16 to produce the title compound. LC/MS m/z 420.2 (MH+), R$_t$ 1.57 minutes. 4-[(2-hydroxyethyl)amino]-3-(5-morpholin-4-ylbenzimidazol-2-yl)hydroquinolin-2-one was produced as a side product (see below).

4-[(2-hydroxyethyl)amino]-3-(5-morpholin-4-ylbenzimidazol-2-yl)hydroquinolin-2-one The title compound was obtained as a side-product of the debenzylation of 4-[(2-methoxyethyl)amino]-3-(5-morpholin-4-ylbenzimidazol-2-yl)-1-benzylhydroquinolin-2-one using the procedure described in Example 16 and was isolated by reversed-phase HPLC as a yellow solid. LC/MS m/z 406.2 (MH+), R$_t$ 1.39 minutes.

Example 20

4-(Methoxyamino)-3-(5-morpholin-4-ylbenzimidazol-2-yl)-1-benzylhydroquinolin-2-one The title compound was synthesized as described in Example 19, Method D using O-methylhydroxylamine. The product was used without purification.

4-(Methoxyamino)-3-(5-morpholin-4-ylbenzimidazol-2-yl)hydroquinolin-2-one

The title compound was obtained as a yellow solid after debenzylation of 4-(methoxyamino)-3-(5-morpholin-4-yl-benzimidazol-2-yl)-1-benzylhydroquinolin-2-one using the procedure described in Example 16. LC/MS m/z 392.2 (MH+), R$_t$ 1.82 minutes.

Example 21 tert-Butyl-3-{[3-(5-morpholin-4-ylbenzimidazol-2-yl)-2-oxo-1-benzyl-4-hydroquinolyl]amino}piperidinecarboxylate The title compound was synthesized as described in Example 19, Method D using 1-tert-butoxycarbonyl-3-aminopiperidine. The product was used without purification.

3-(5-Morpholin-4-ylbenzimidazol-2-yl)-4-(3-piperidylamino)hydroquinolin-2-one The product was obtained as a yellow solid after debenzylation of tert-butyl-3-{[3-(5-morpholin-4-ylbenzimidazol-2-yl)-2-oxo-1-benzyl-4-hydroquinolyl]amino}piperidinecarboxylate using the procedure described in Example 16. The t-butoxycarbonyl group is removed under the reaction conditions. LC/MS m/z 445.4 (MH+), R$_t$ 1.73 minutes.

Example 22 tert-Butyl-3-({[3-(5-morpholin-4-ylbenzimidazol-2-yl)-2-oxo-1-benzyl-4-hydroquinolyl]amino}methyl)piperidinecarboxylate The title compound was synthesized as described in Example 19. Method D using 1-tert-butoxycarbonyl-3-aminomethylpiperidine. The product was used without purification.

3-(5-Morpholin-4-ylbenzimidazol-2-yl)-4-[(3-piperidylmethyl)amino]-hydroquinolin-2-one The title compound was obtained as a yellow solid after debenzylation of tert-butyl-3-({[3-(5-morpholin-4-ylbenzimidazol-2-yl)-2-oxo-1-benzyl-4-hydroquinolyl]amino}methyl)piperidinecarboxylate using the procedure described in Example 16. LC/MS m/z 459.6 (MH+), R$_t$ 1.71 minutes.

Example 23

4-{[2-(Dimethylamino)ethyl]amino}-3-(5-morpholin-4-ylbenzimidazol-2-yl)-1-benzylhydroquinolin-2-one The title compound was synthesized as described in Example 19, Method D using 1,1-dimethylethylenediamine. The product was used without purification.

4-{[2-(Dimethylamino)ethyl]amino}-3-(5-morpholin-4-ylbenzimidazol-2-yl)hydroquinolin-2-one The title compound was obtained as a yellow solid after debenzylation of 4-{[2-(dimethylamino)ethyl]amino}-3-(5-morpholin-4-ylbenzimidazol-2-yl)-1-benzylhydroquinolin-2-one using the procedure described in Example 16. LC/MS m/z 433.4 (MH+), R$_t$ 1.55 minutes.

Example 24

3-(5-Morpholin-4-ylbenzimidazol-2-yl)-4-[(oxolan-2-ylmethyl)amino]-1-benzylhydroquinolin-2-one The title compound was synthesized as described in Example 19, Method D using 2-aminomethyltetrahydrofuran. The product was used without purification.

3-(5-Morpholin-4-ylbenzimidazol-2-yl)-4-[(oxolan-2-ylmethyl)amino]-hydroquinolin-2-one The title compound was obtained as a yellow solid after debenzylation of 3-(5-morpholin-4-ylbenzimidazol-2-yl)-4-[(oxolan-2-ylmethyl)amino]-1-benzylhydroquinolin-2-one using the procedure described in Example 16. LC/MS m/z 446.5 (MH+), $R_t$ 2.19 minutes.

Example 25

4-{[2-(Methylamino)ethyl]amino}-3-(5-morpholin-4-ylbenzimidazol-2-yl)-1-benzylhydroquinolin-2-one The title compound was synthesized as described in Example 19, Method D using 1-tert-butoxycarbonyl-1-methylethylenediamine. The product was used without purification.

4-{[2-(Methylamino)ethyl]amino}-3-(5-morpholin-4-ylbenzimidazol-2-yl)hydroquinolin-2-one The title compound was obtained as a yellow solid after debenzylation of 4-{[2-(methylamino)ethyl]amino}-3-(5-morpholin-4-ylbenzimidazol-2-yl)-1-benzylhydroquinolin-2-one using the procedure described in Example 16. The t-butoxycarbonyl group is removed under the reaction conditions. LC/MS m/z 419.4 (MH+), $R_t$ 1.50 minutes.

Example 26 tert-Butyl-3-{[3-(5-morpholin-4-ylbenzimidazol-2-yl)-2-oxo-1-benzyl-4-hydroquinolyl]amino}pyrrolidinecarboxylate The title compound was synthesized as described in Example 19, Method D using 1-tert-butoxycarbonyl-3-aminopyrrolidine. The product was used without purification.

3-(5-Morpholin-4-ylbenzimidazol-2-yl)-4-(pyrrolidin-3-ylamino)hydroquinolin-2-one The title compound was obtained as a yellow solid after debenzylation of tert-butyl-3-{[3-(5-morpholin-4-ylbenzimidazol-2-yl)-2-oxo-1-benzyl-4-hydroquinolyl]amino}pyrrolidinecarboxylate using the procedure described in Example 16. LC/MS m/z 431.4 (MH+), $R_t$ 1.50 minutes.

Example 27

4-[((2S)-2-Amino-4-methylpentyl)amino]-3-(5-morpholin-4-ylbenzimidazol-2-yl)-1-benzylhydroquinolin-2-one The title compound was synthesized as described in Example 19, Method D using (2S)-2-tert-butoxycarbonylamino-4-methylpentylamine. The product was used without purification.

4-[((2S)-2-Amino-4-methylpentyl)amino]-3-(5-morpholin-4-ylbenzimidazol-2-yl)hydroquinolin-2-one The title compound was obtained as a yellow solid after debenzylation of 4-[((2S)-2-amino-4-methylpentyl)amino]-3-(5-morpholin-4-ylbenzimidazol-2-yl)-1-benzylhydroquinolin-2-one using the procedure described in Example 16. LC/MS m/z 461.4 (MH+), $R_t$ 1.78 minutes.

Example 28 t-Butoxycarbonyl protected 4-[((2S)-2-amino-3-methylbutyl)amino]-3-(5-morpholin-4-ylbenzimidazol-2-yl)-1-benzylhydroquinolin-2-one The title compound was synthesized as described in Example 19, Method D using (2S)-2-tert-butoxycarbonylamino-3-methylbutylamine. The product was used without purification.

4-[((2S)-2-Amino-3-methylbutyl)amino]-3-(5-morpholin-4-ylbenzimidazol-2-yl)hydroquinolin-2-one The title compound was obtained as a yellow solid after debenzylation of 4-[((2S)-2-amino-3-methylbutyl)amino]-3-(5-morpholin-4-ylbenzimidazol-2-yl)-1-benzylhydroquinolin-2-one using the procedure described in Example 16. The t-butoxycarbonyl group is removed under the reaction conditions. LC/MS m/z 447.5 (MH+), $R_t$ 2.96 minutes.

Example 29

4-Amino-3-(5-morpholin-4-ylbenzimidazol-2-yl)-1-benzylhydroquinolin-2-one

The title compound was synthesized as described in Example 19, Method D using ammonia in a sealed glass tube. The product was used without purification.

4-Amino-3-(5-morpholin-4-ylbenzimidazol-2-yl)hydroquinolin-2-one

The title compound was obtained as a bright yellow solid after debenzylation of 4-amino-3-(5-morpholin-4-ylbenzimidazol-2-yl)-1-benzylhydroquinolin-2-one using the procedure described in Example 16 and purification by reversed-phase HPLC. LC/MS m/z 362.3 (MH+), $R_t$ 1.61 minutes.

Example 30

3-Benzimidazol-2-yl-4-hydroxy-1-benzylhydroquinolin-2-one

The title compound was synthesized as described in Example 16, Method C using ethyl 2-benzimidazol-2-ylacetate. The product was obtained as a white solid and used without further purification. LC/MS m/z 368.4 (MH+), $R_t$ 2.99 minutes.

3-(Benzimidazol-2-yl)-4-chloro-1-benzylhydroquinolin-2-one

The title compound was synthesized as described in Example 19, Method D using 3-benzimidazol-2-yl-4-hydroxy-1-benzylhydroquinolin-2-one. The crude product was used without purification.

Example 31

3-Benzimidazol-2-yl-4-(methylamino)hydroquinolin-2-one

The benzylated title compound was synthesized as described in Example 19, Method D using methylamine and 3-(benzimidazol-2-yl)-4-chloro-1-benzylhydroquinolin-2-one. The product was obtained after debenzylation as a yellow solid using the procedure described in Example 16. LC/MS m/z 291.3 (MH+), $R_t$ 1.64 minutes.

Example 32

3-Benzimidazol-2-yl-4-(ethylamino)hydroquinolin-2-one

The benzylated title compound was synthesized as described in Example 19, Method D using ethylamine and 3-(benzimidazol-2-yl)-4-chloro-1-benzylhydroquinolin-2-one. The title compound was obtained after debenzylation as a yellow solid using the procedure described in Example 16. LC/MS m/z 305.3 (MH+), $R_t$ 2.01 minutes.

Example 33

3-Benzimidazol-2-yl-4-[(oxolan-2-ylmethyl)amino]hydroquinolin-2-one

The benzylated title compound was synthesized as described in Example 19, Method D using 2-aminomethyltetrahydrofuran and 3-(benzimidazol-2-yl)-4-chloro-1-benzylhydroquinolin-2-one. The title compound was obtained after debenzylation as a yellow solid using the procedure described in Example 16. LC/MS m/z 361.2 (MH+), $R_t$ 1.74 minutes.

Example 34

3-Benzimidazol-2-yl-4-[(4-piperidylmethyl)amino]hydroquinolin-2-one

The protected title compound was synthesized as described in Example 19, Method D using 1-tert-butoxycarbonyl-4-aminomethylpiperidine and 3-(benzimidazol-2-yl)-4-chloro-1-benzylhydroquinolin-2-one. The title compound was obtained after deprotection and debenzylation as a yellow solid using the procedure described in Example 16. LC/MS m/z 374.3 (MH+), $R_t$ 1.29 minutes.

Example 35

3-Benzimidazol-2-yl-4-[(4-fluorophenyl)amino]hydroquinolin-2-one

The benzylated title compound was synthesized as described in Example 19, Method D using 4-fluoroaniline and 3-(benzimidazol-2-yl)-4-chloro-1-benzylhydroquinolin-2-one. The title compound was obtained after debenzylation as a yellow solid using the procedure described in Example 16. LC/MS m/z 371.2 (MH+), $R_t$ 1.92 minutes.

Example 36

3-Benzimidazol-2-yl-4-(methoxyamino)hydroquinolin-2-one

The benzylated title compound was synthesized as described in Example 19, Method D using O-methylhydroxylamine and 3-(benzimidazol-2-yl)-4-chloro-1-benzylhydroquinolin-2-one. The title compound was obtained after debenzylation as a yellow solid using the procedure described in Example 16. LC/MS m/z 307.3 (MH+), $R_t$ 1.77 minutes.

Example 37

3-Benzimidazol-2-yl-4-(benzimidazol-6-ylamino)hydroquinolin-2-one

The benzylated title compound was synthesized as described in Example 19, Method D using 5-aminobenzimidazole and 3-(benzimidazol-2-yl)-4-chloro-1-benzylhydroquinolin-2-one. The title compound was obtained after debenzylation as a yellow solid using the procedure described in Example 16. LC/MS m/z 393.4 (MH+), $R_t$ 1.41 minutes.

Example 38

3-Benzimidazol-2-yl-4-(phenylamino)hydroquinolin-2-one

The benzylated title compound was synthesized as described in Example 19, Method D using aniline and 3-(benzimidazol-2-yl)-4-chloro-1-benzylhydroquinolin-2-one. The title compound was obtained after debenzylation as a yellow solid using the procedure described in Example 16. LC/MS m/z 353.4 (MH+), $R_t$ 2.38 minutes.

Example 39

3-Benzimidazol-2-yl-4-(quinuclidin-3-ylamino)hydroquinolin-2-one

The benzylated title compound was synthesized as described in Example 19, Method D using 3-aminoquinuclidine and 3-(benzimidazol-2-yl)-4-chloro-1-benzylhydroquinolin-2-one. The title compound was obtained after debenzylation as a yellow solid using the procedure described in Example 16. LC/MS m/z 386.4 (MH+), $R_t$ 1.82 minutes.

Example 40

3-Benzimidazol-2-yl-4-[(imidazol-5-ylmethyl)amino]hydroquinolin-2-one

The benzylated title compound was synthesized as described in Example 19, Method D using 4-aminomethyl-1H-imidazole and 3-(benzimidazol-2-yl)-4-chloro-1-benzylhydroquinolin-2-one. The title compound was obtained after debenzylation as a yellow solid using the procedure described in Example 16. LC/MS m/z 357.4 (MH+), $R_t$ 1.34 minutes.

Example 41

3-Benzimidazol-2-yl-4-(morpholin-4-ylamino)hydroquinolin-2-one

The benzylated title compound was synthesized as described in Example 19, Method D using 4-aminomorpholine and 3-(benzimidazol-2-yl)-4-chloro-1-benzylhydroquinolin-2-one. The title compound was obtained after debenzylation as a yellow solid using the procedure described in Example 16. LC/MS m/z 362.4 (MH+), $R_t$ 1.42 minutes.

Example 42

3-Benzimidazol-2-yl-4-hydrazinohydroquinolin-2-one

The benzylated title compound was synthesized as described in Example 19, Method D using hydrazine and 3-(benzimidazol-2-yl)-4-chloro-1-benzylhydroquinolin-2-one. The title compound was obtained as a yellow solid after debenzylation using the procedure described in Example 16. LC/MS m/z 292.3 (MH+), $R_t$ 1.19 minutes.

Example 43

3-Benzimidazol-2-yl-2-oxohydroquinoline-4-carbonitrile

3-Benzimidazol-2-yl-4-chloro-1-benzylhydroquinolin-2-one (1 eq) was dissolved in DMA, and CuCN (10 eq) was added in one portion. The reaction mixture was stirred at 90° C. overnight. The resulting mixture was allowed to cool to room temperature, water was added, and the orange precipitate was removed by filtration. The solid was treated with a solution of hydrated $FeCl_3$ at 70° C. for 1 hour. The suspension was centrifuged and the solution removed. The remaining solid was washed with 6N HCl (2 times), sat. $Na_2CO_3$ (2 times), water (2 times) and lyophilized. The resulting powder was dissolved in 1 mL of triflic acid and heated at 60° C. overnight. The resulting mixture was cooled to 0° C. and water was slowly added. Saturated LiOH was added dropwise to the suspension to a pH of 8, then the solid was filtered and washed with water (3 times). Purification by reversed-phase HPLC afforded the desired product. LC/MS m/z 287.1 (MH+), $R_t$ 1.89 minutes.

Example 44

Ethyl 2-(5,6-dimethylbenzimidazol-2-yl)acetate

The title compound was synthesized as described in Example 1 using 4,5-dimethylbenzene-1,2-diamine. The crude yellow oil was purified first by silica gel chromatography (96.5:3.0:0.5, $CH_2Cl_2$:MeOH:$Et_3N$), and then by recrystallization from toluene to yield the title compound as a pale, yellow solid. LC/MS m/z 233.1 (MH+), $R_t$ 1.73 minutes.

3-(5,6-Dimethylbenzimidazol-2-yl)-4-hydroxy-1-benzylhydroquinolin-2-one

The title compound was synthesized as described in Example 16, Method C using ethyl 2-(5,6-dimethylbenzimidazol-2-yl)acetate. The crude material was purified by silica gel chromatography (98.5:1.5, $CH_2Cl_2$:MeOH) to yield the title compound as a yellow solid. LC/MS m/z 396.2 (MH+), $R_t$ 3.60 minutes.

3-(5,6-Dimethylbenzimidazol-2-yl)-4-chloro-1-benzylhydroquinolin-2-one

The title compound was synthesized as described in Example 19, Method D using 3-(5,6-dimethylbenzimidazol-2-yl)-4-hydroxy-1-benzylhydroquinolin-2-one. The title compound was obtained as an orange-yellow solid. LC/MS m/z 414.2 (MH+), $R_t$ 2.47 minutes.

tert-Butyl 3-{[3-(5,6-dimethylbenzimidazol-2-yl)-2-oxo-1-benzyl-4-hydroquinolyl]amino}piperidinecarboxylate The title compound was synthesized as described in Example 19, Method D using 1-tert-butoxycarbonyl-3-aminopiperidine. The crude material was purified by silica gel chromatography (99:1 $CH_2Cl_2$:MeOH) to yield the title compound as a yellow solid. LC/MS m/z 578.5 (MH+), $R_t$ 3.05 minutes.

3-(5,6-Dimethylbenzimidazol-2-yl)-4-(3-piperidylamino)hydroquinolin-2-one tert-Butyl 3-{[3-(5,6-dimethylbenzimidazol-2-yl)-2-oxo-1-benzyl-4-hydroquinolyl]amino}piperidine-carboxylate was debenzylated as described in Example 16. The crude material was purified by reversed-phase HPLC to yield the title compound as a light yellow solid. LC/MS m/z 388.4 (MH+), $R_t$ 1.61 minutes.

Example 45

3H-Imidazo[4,5-b]pyridin-2-ylacetonitrile

Ethyl cyanoacetate (1.5 eq) and 2,3-diaminopyridine (1 eq) were heated at 185° C. for 30 minutes. The reaction mixture was cooled to room temperature and the black solid was triturated with ether. The desired product was thus obtained as a dark brown powder. LC/MS m/z 159.1 (MH+), $R_t$ 0.44 minutes.

Ethyl 3H-imidazo[4,5-b]pyridin-2-ylacetate

3H-Imidazo[4,5-b]pyridin-2-ylacetonitrile was suspended in EtOH, and gaseous HCl was bubbled through for 3 hours. The suspension initially seemed to dissolve, but a precipitate started forming almost immediately. The reaction mixture was cooled to 0° C. and a cold saturated $NaHCO_3$ solution was carefully added. Solid $NaHCO_3$ was also added to bring the pH to a value of 7.6. The aqueous phase was then extracted with EtOAc, and the organic extracts were dried ($Na_2SO_4$). After evaporation of the solvent under reduced pressure, the residue was purified by chromatography on silicagel (10% MeOH in $CH_2Cl_2$ with 1% $Et_3N$) providing the desired product as a light brown solid. LC/MS m/z 206.1 (MH+), $R_t$ 0.97 minutes.

4-Amino-3-(3H-imidazo[4,5-b]pyridin-2-yl)quinolin-2(1H)-one

LiHMDS (3.0 eq) was added to ethyl 3H-imidazo[4,5-b]pyridin-2-ylacetate (1.0 eq) in THF at −78° C. After 20 minutes, a solution of 2-aminobenzenecarbonitrile (1.1 eq) in THF was added. The resulting mixture was allowed to warm to room temperature, stirred for 3 hours, and then refluxed overnight. The mixture was cooled to 0° C. and quenched with an aqueous saturated $NH_4Cl$ solution. A precipitate formed, was filtered off, and was washed repeatedly with ether to yield the desired compound as a light brown solid. LC/MS m/z 278.2 (MH+), $R_t$ 1.82 minutes.

Example 46

6-Morpholin-4-yl-3-nitropyridin-2-amine

Morpholine (4 eq) was added to a suspension of 6-chloro-3-nitropyridin-2-amine (1 eq) in $CH_3CN$, and the reaction mixture was stirred at 70° C. for 5 hours. The solvent was evaporated under reduced pressure, and the residue was triturated with ether to afford the desired compound as a bright yellow powder. LC/MS m/z 225.0 (MH+), $R_t$ 1.79 minutes.

Ethyl (5-morpholin-4-yl-3H-imidazo[4,5-b]pyridin-2-yl)acetate

To a solution 6-chloro-3-nitropyridin-2-amine (1.0 eq) in EtOH was added Pd/C (0.1 eq). The reaction vessel was repeatedly purged with hydrogen and then stirred under a hydrogen atmosphere (1 atm) for 18 hours. Ethyl 3-ethoxy-3-iminopropanoate hydrochloride (2.0 eq) was added in one portion, and the reaction mixture was refluxed overnight. The reaction mixture was cooled to room temperature, filtered through a celite plug, and the plug was washed with EtOH. After evaporation of the solvent under reduced pressure, the residue was purified by silica gel chromatography (5% MeOH in $CH_2Cl_2$ with 1% $Et_3N$) providing the desired product as a brown solid. LC/MS m/z 291.3 (MH+), $R_t$ 1.71 minutes.

4-Amino-3-(5-morpholin-4-yl-3H-imidazo[4,5-b]pyridin-2-yl)quinolin-2(1H)-one

The title compound was synthesized as described in Example 45, Method E using ethyl 2-(5-morpholin-4-ylimidazolo[5,4-b]pyridin-2-yl)acetate and 2-aminobenzenecarbonitrile, with a modified workup procedure. After quenching with a saturated aqueous ammonium chloride solution, the two phases were separated and the aqueous phase extracted with EtOAc. Upon standing, a solid formed and precipitated out of the organic extracts. The precipitate, a dark brown solid, was filtered off and dried. Purification by reverse phase chromatography afforded the desired product as a reddish solid. LC/MS m/z 363.2 (MH+), $R_t$ 2.20 minutes.

Example 47

4-Amino-5-[(2R,6S)-2,6-dimethylmorpholin-4-yl]-3-(3H-imidazo[4,5-b]pyridin-2-yl)quinolin-2(1H)-one LiHMDS (3.0 eq) was added to ethyl 3H-imidazo[4,5-b]pyridin-2-ylacetate (1.0 eq) in THF at −78° C. After 20 minutes, a solution of 2-amino-6-[(2R,6S)-2,6-dimethylmorpholin-4-yl]benzonitrile (1.1 eq) in THF was added. The resulting mixture was allowed to warm to room temperature, stirred for 2 hours and then heated to 60° C. overnight. The mixture was cooled to 0° C. and quenched with an aqueous saturated $NH_4Cl$ solution. The aqueous phase was extracted with $CH_2Cl_2$ (5 times) and the organic extracts were collected, dried ($Na_2SO_4$), and concentrated. The crude product was purified by HPLC. LC/MS m/z 391.2 (MH+), $R_t$ 2.35 minutes.

Example 48

Ethyl {5-[3-(dimethylamino)pyrrolidin-1-yl]-3H-imidazo[4,5-b]pyridin-2-yl}acetate 6-chloro-3-nitro-2-aminopyridine (1.0 eq) and 3-(dimethylamino)pyrrolidine (1.1 eq) were dissolved in $CH_3CN$ and diisopropylethylamine(2.0 eq) was added. The reaction mixture was heated at 70° C. overnight. The solution was cooled to room temperature, and the solvent was evaporated. The residue was triturated with ether and water and dried under vacuum (LC/MS m/z 252.2 (MH+), $R_t$ 1.09 minutes). The isolated product (1.0 eq) and 10% Pd/C (0.1 eq) were suspended in anhydrous EtOH at room temperature. The reaction flask was evacuated and subsequently filled with $H_2$. The resulting mixture was allowed to stir under a hydrogen atmosphere overnight. Ethyl 3-ethoxy-3-iminopropanoate hydrochloride (2.0 eq) was then added and the resulting mixture was heated at reflux overnight. The solution was then filtered through Celite and evaporated under reduced pressure. The residue was suspended in $CH_2Cl_2$ and concentrated $NH_4OH$ was added until a pH of 11 was achieved. The $NH_4Cl$ thus formed was filtered off. The two phases were separated, and the organic phase was dried ($Na_2SO_4$). Evaporation of the solvent and trituration of the residue with ether gave a light green powder. LC/MS m/z 318.1 (MH+), $R_t$ 1.11 minutes.

4-Amino-3-{5-[3-(dimethylamino)pyrrolidin-1-yl]-3H-imidazo[4,5-b]pyridin-2-yl}quinolin-2(1H)-one LiHMDS (3.5 eq) was added to ethyl {5-[3-(dimethylamino)pyrrolidin-1-yl]-3H-imidazo[4,5-b]pyridin-2-yl}acetate (1.0 eq) in THF at −40° C. After 10 minutes, a solution of 2-aminobenzenecarbonitrile (1.1 eq) in THF was added. The resulting mixture was allowed to warm to room temperature, stirred for 1 h and then heated to 60° C. overnight. The mixture was cooled to room temperature and quenched with $NH_4Cl$ (aq, saturated). The aqueous phase was extracted with $CH_2Cl_2$ (5 times). The product crashes out of the organic solution during the extractions. Evaporation of the solvent under reduced pressure afforded a brown solid that was triturated repeatedly with MeOH and acetone to obtain a yellow greenish powder. LC/MS m/z 390.2 (MH+), $R_t$ 1.48 minutes.

Example 49

2-(4-Ethyl piperazinyl)-6-nitrobenzenecarbonitrile 2,6-Dinitrobenzenecarbonitrile (1.0 eq) and ethylpiperazine (3.6 eq) were dissolved in DMF. The resulting solution heated at 90° C. for 2 hours. The solution was cooled to room temperature and poured into $H_2O$. A precipitate formed which was filtered to yield the desired product as a brown solid. LC/MS m/z 260.1 (MH+), $R_t$ 1.69 minutes.

6-Amino-2-(4-ethylpiperazinyl)benzenecarbonitrile 2-(4-Ethylpiperazinyl)-6-nitrobenzenecarbonitrile (1.0 eq) was dissolved in EtOH and EtOAc. The flask was purged with $N_2$, and 10% Pd/C (0.1 eq) was added. The flask was evacuated and purged with $H_2$ three times. The resulting mixture was stirred overnight at room temperature. The mixture was filtered through Celite, and the filter pad was washed with EtOAc. The solvent was removed in vacuo to provide the desired product as a yellow solid. LC/MS m/z 231.2 (MH+), $R_t$ 1.42 minutes.

4-Amino-3-(1H-benzimidazol-2-yl)-5-(4-ethylpiperazin-1-yl)quinolin-2(1H)-one t-BuLi (3.1 eq) was added to ethyl 2-benzimidazol-2-ylacetate (1.0 eq) and 6-amino-2-(4-ethylpiperazinyl)benzenecarbonitrile (1.0 eq) in THF at 0° C. The reaction was stirred overnight. The resulting mixture was quenched with NH₄Cl (aq, saturated) and extracted with EtOAc. The combined organic layers were washed with H₂O and brine, dried over Na₂SO₄, filtered, and concentrated in vacuo to yield a brown solid. The crude material was triturated with CH₂Cl₂ and MeOH to provide a tan solid. LC/MS m/z 389.1 (MH+), R$_t$ 1.80 minutes.

Examples 50-154

The 2-aminobenzonitriles or isatoic anhydride starting materials used to synthesize Examples 50-154 are readily recognizable by one skilled in the art. They were either commercially available or synthesized following the examples shown above (e.g. Examples 1, 2, and 49). The anhydride 6-chloro-1-(phenylmethyl)-2H-3, 1-benzoxazine-2,4(1H)-dione was synthesized following the general isatoic anhydride synthesis methods described in *J. Med. Chem.* 1981, 24 (6), 735 and *J. Heterocycl. Chem.* 1975, 12(3), 565.

The benzimidazole acetates were formed by reacting aryl diamines with ethyl 3-ethoxy-3-iminopropanoate hydrochloride as shown in Example 1. The requisite diamines used in the syntheses are also readily recognizable by one skilled in the art and may be synthesized following Methods 1-9. The isatoic anhydrides were coupled with the benzimidazole acetates using methods C and D. The 2-aminobenzonitriles were coupled with the benzimidazole acetates using method B, the coupling method of example 49, or the general procedure set forth below.

Method E

LiHMDS (3-4 eq) was added to the benzimidazole acetate (1.0 eq) in THF (at a constant temperature ranging from −78° C. to 0C). After 20 minutes, a solution of the 2-aminobenzonitrile (1.1 eq) in THF was then added. The resulting mixture was allowed to warm to room temperature, stirred for 1-3 hours and was then heated to approx. 40° C.-65° C. (1 hour to 12 hours). The mixture was cooled to 0° C. and quenched with NH₄Cl (aq, saturated). The aqueous phase was extracted with CH₂Cl₂ or EtOAc, and the organic extracts were collected, dried (Na₂SO₄), and filtered. Evaporation of the solvent under reduced pressure and purification of the residue by silica gel chromatography or HPLC provided the 4-amino quinolinone products.

| Example | Name | LC/MS m/z (MH+) |
|---|---|---|
| 50 | 4-amino-3-{5-[(3S)-3-(dimethylamino)pyrrolidin-1-yl]-1H-benzimidazol-2-yl}quinolin-2(1H)-one | 389.4 |
| 51 | 4-[(3S)-1-azabicyclo[2.2.2]oct-3-ylamino]-3-(1H-benzimidazol-2-yl)-6-chloroquinolin-2(1H)-one | 420 |
| 52 | 4-[(3R)-1-azabicyclo[2.2.2]oct-3-ylamino]-3-(1H-benzimidazol-2-yl)-6-chloroquinolin-2(1H)-one | 420 |
| 53 | 3-(1H-benzimidazol-2-yl)-4-[(3R)-3-(dimethylamino)pyrrolidin-1-yl]quinolin-2(1H)-one | 374.2 |
| 54 | 3-(1H-benzimidazol-2-yl)-6-chloro-4-[(3R)-3-(dimethylamino)pyrrolidin-1-yl]quinolin-2(1H)-one | 408.1 |
| 55 | 4-amino-3-[5-(4-ethylpiperazin-1-yl)-1H-benzimidazol-2-yl]-1-methylquinolin-2(1H)-one | 403.2 |
| 56 | 4-amino-3-(6-piperazin-1-yl-1H-benzimidazol-2-yl)quinolin-2(1H)-one | 361.2 |
| 57 | 4-amino-3-[6-(pyridin-4-ylmethyl)-1H-benzimidazol-2-yl]quinolin-2(1H)-one | 368.2 |
| 58 | 4-amino-3-{5-[(3R,5S)-3,5-dimethylpiperazin-1-yl]-1H-benzimidazol-2-yl}quinolin-2(1H)-one | 389.4 |
| 59 | 4-amino-3-[5-(4-methylpiperazin-1-yl)-1H-benzimidazol-2-yl]quinolin-2(1H)-one | 375.2 |
| 60 | 4-amino-3-(6-methyl-5-morpholin-4-yl-1H-benzimidazol-2-yl)quinolin-2(1H)-one | 376 |
| 61 | 4-amino-3-{5-[(1-methylpiperidin-3-yl)oxy]-1H-benzimidazol-2-yl}quinolin-2(1H)-one | 390.1 |
| 62 | 4-amino-3-{5-[(2R,6S)-2,6-dimethylmorpholin-4-yl]-6-fluoro-1H-benzimidazol-2-yl}quinolin-2(1H)-one | 408.2 |
| 63 | 4-amino-3-{5-[(1-methylpyrrolidin-3-yl)oxy]-1H-benzimidazol-2-yl}quinolin-2(1H)-one | 376.2 |
| 64 | 4-amino-3-[5-(4-methyl-1,4-diazepan-1-yl)-1H-benzimidazol-2-yl]quinolin-2(1H)-one | 389.2 |
| 65 | 4-amino-3-{5-[(3R)-3-(dimethylamino)pyrrolidin-1-yl]-1H-benzimidazol-2-yl}quinolin-2(1H)-one | 389.2 |
| 66 | 4-amino-6-chloro-3-{5-[(3R)-3-(dimethylamino)pyrrolidin-1-yl]-1H-benzimidazol-2-yl}quinolin-2(1H)-one | 423 |
| 67 | ethyl {4-[2-(4-amino-2-oxo-1,2-dihydroquinolin-3-yl)-1H-benzimidazol-6-yl]piperazin-1-yl}acetate | 447.2 |
| 68 | 4-amino-3-{6-[methyl(1-methylpiperidin-4-yl)amino]-1H-benzimidazol-2-yl}quinolin-2(1H)-one | 403.1 |
| 69 | 3-[6-(4-acetylpiperazin-1-yl)-1H-benzimidazol-2-yl]-4-aminoquinolin-2(1H)-one | 403.3 |
| 70 | 4-amino-3-[6-(1,4'-bipiperidin-1'-yl)-1H-benzimidazol-2-yl]quinolin-2(1H)-one | 443.3 |
| 71 | 2-(4-amino-2-oxo-1,2-dihydroquinolin-3-yl)-1H-benzimidazole-6-carboxylic acid | 321.2 |
| 72 | 4-amino-5-(methyloxy)-3-[6-(4-methylpiperazin-1-yl)-1H-benzimidazol-2-yl]quinolin-2(1H)-one | 405.3 |
| 73 | 4-amino-3-{6-[4-(1-methylethyl)piperazin-1-yl]-1H-benzimidazol-2-yl}quinolin-2(1H)-one | 403.3 |
| 74 | {4-[2-(4-amino-2-oxo-1,2-dihydroquinolin-3-yl)-1H-benzimidazol-6-yl]piperazin-1-yl}acetic acid | 419.2 |
| 75 | 4-[(3S)-1-azabicyclo[2.2.2]oct-3-ylamino]-3-(1H-benzimidazol-2-yl)quinolin-2(1H)-one | 386.1 |
| 76 | 4-[(3R)-1-azabicyclo[2.2.2]oct-3-ylamino]-3-(1H-benzimidazol-2-yl)quinolin-2(1H)-one | 386.1 |
| 77 | 4-amino-3-[5-(4-ethylpiperazin-1-yl)-1H-benzimidazol-2-yl]quinolin-2(1H)-one | 389.1 |
| 78 | 4-amino-3-(5-{(2S,5S)-2-[(dimethylamino)methyl]-5-methylmorpholin-4-yl}-1H-benzimidazol-2-yl)quinolin-2(1H)-one | 433.3 |
| 79 | 4-amino-6-chloro-3-[5-(4-methylpiperazin-1-yl)-1H-benzimidazol-2-yl]quinolin-2(1H)-one | 409.2 |
| 80 | 4-amino-6-chloro-3-{5-[(3S)-3-(dimethylamino)pyrrolidin-1-yl]-1H-benzimidazol-2-yl}quinolin-2(1H)-one | 423.1 |
| 81 | 4-amino-5,6-dichloro-3-{5-[(3S)-3-(dimethylamino)pyrrolidin-1-yl]-1H-benzimidazol-2-yl}quinolin-2(1H)-one | 457.2 |
| 82 | 4-amino-5,6-dichloro-3-[5-(4-methylpiperazin-1-yl)-1H-benzimidazol-2-yl]quinolin-2(1H)-one | 443.2 |

-continued

| Example | Name | LC/MS m/z (MH+) |
|---|---|---|
| 83 | 4-amino-3-(1H-benzimidazol-2-yl)-6-[(pyridin-2-ylmethyl)oxy]quinolin-2(1H)-one | 384.2 |
| 84 | 4-amino-3-(1H-benzimidazol-2-yl)-6-[(2R,6S)-2,6-dimethylmorpholin-4-yl]quinolin-2(1H)-one | 390.1 |
| 85 | 4-amino-3-(1H-benzimidazol-2-yl)-6-morpholin-4-ylquinolin-2(1H)-one | 362.2 |
| 86 | 4-amino-3-(1H-benzimidazol-2-yl)-5-[(1-methylpiperidin-3-yl)oxy]quinolin-2(1H)-one | 390.2 |
| 87 | 4-amino-3-(1H-benzimidazol-2-yl)-5-[(pyridin-2-ylmethyl)oxy]quinolin-2(1H)-one | 384.1 |
| 88 | 4-amino-3-(5-morpholin-4-yl-1H-benzimidazol-2-yl)-5-[(pyridin-4-ylmethyl)oxy]quinolin-2(1H)-one | 469.2 |
| 89 | 4-amino-3-(1H-benzimidazol-2-yl)-5-(methyloxy)quinolin-2(1H)-one | 307.1 |
| 90 | 4-amino-3-(5-methyl-1H-benzimidazol-2-yl)-5-(methyloxy)quinolin-2(1H)-one | 321.1 |
| 91 | 4-amino-3-{5-[(2R,6S)-2,6-dimethylmorpholin-4-yl]-1H-benzimidazol-2-yl}-5-(methyloxy)quinolin-2(1H)-one | 420.2 |
| 92 | 4-amino-3-(1H-benzimidazol-2-yl)-5-morpholin-4-ylquinolin-2(1H)-one | 362.2 |
| 93 | 4-amino-3-(1H-benzimidazol-2-yl)-5-[(2R,6S)-2,6-dimethylmorpholin-4-yl]quinolin-2(1H)-one | 390.2 |
| 94 | 4-amino-3-(1H-benzimidazol-2-yl)-5-(4-methylpiperazin-1-yl)quinolin-2(1H)-one | 375.1 |
| 95 | 4-amino-5,6-dichloro-3-(5-morpholin-4-yl-1H-benzimidazol-2-yl)quinolin-2(1H)-one | 430 |
| 96 | 3-{5-[(2-morpholin-4-ylethyl)oxy]-1H-benzimidazol-2-yl}quinolin-2(1H)-one | 391.3 |
| 97 | 4-amino-3-{5-[(3-pyrrolidin-1-ylpropyl)oxy]-1H-benzimidazol-2-yl}quinolin-2(1H)-one | 404 |
| 98 | 4-amino-3-{5-[(3-morpholin-4-ylpropyl)oxy]-1H-benzimidazol-2-yl}quinolin-2(1H)-one | 420.4 |
| 99 | 4-amino-6-fluoro-3-(5-morpholin-4-yl-1H-benzimidazol-2-yl)quinolin-2(1H)-one | 380 |
| 100 | 4-amino-3-{5-[3-(dimethylamino)pyrrolidin-1-yl]-1H-benzimidazol-2-yl}-6-fluoroquinolin-2(1H)-one | 407 |
| 101 | 4-amino-3-(1H-benzimidazol-2-yl)-6-fluoroquinolin-2(1H)-one | 295 |
| 102 | 4-amino-3-(6-fluoro-5-morpholin-4-yl-1H-benzimidazol-2-yl)quinolin-2(1H)-one | 380 |
| 103 | 4-amino-3-{5-[(tetrahydrofuran-2-ylmethyl)oxy]-1H-benzimidazol-2-yl}quinolin-2(1H)-one | 377 |
| 104 | 4-amino-6-fluoro-3-(6-fluoro-5-morpholin-4-yl-1H-benzimidazol-2-yl)quinolin-2(1H)-one | 398 |
| 105 | 4-amino-3-[6-fluoro-5-(4-methylpiperazin-1-yl)-1H-benzimidazol-2-yl]quinolin-2(1H)-one | 393 |
| 106 | 4-amino-3-(5-{[2-(methyloxy)ethyl]oxy}-1H-benzimidazol-2-yl)quinolin-2(1H)-one | 351 |
| 107 | 4-amino-3-[4,6-difluoro-5-(4-methylpiperazin-1-yl)-1H-benzimidazol-2-yl]quinolin-2(1H)-one | 411 |
| 108 | 4-amino-3-{5-[3-(dimethylamino)pyrrolidin-1-yl]-1H-benzimidazol-2-yl}-5-fluoroquinolin-2(1H)-one | 407.1 |
| 109 | 4-amino-5-fluoro-3-[5-(4-methylpiperazin-1-yl)-1H-benzimidazol-2-yl]quinolin-2(1H)-one | 393.1 |
| 110 | 4-amino-5-chloro-3-[5-(4-methylpiperazin-1-yl)-1H-benzimidazol-2-yl]quinolin-2(1H)-one | 409.1 |
| 111 | 4-amino-3-{5-[3-(dimethylamino)pyrrolidin-1-yl]-6-fluoro-1H-benzimidazol-2-yl}quinolin-2(1H)-one | 407.1 |
| 112 | 4-amino-5-chloro-3-{5-[3-(dimethylamino)pyrrolidin-1-yl]-1H-benzimidazol-2-yl}quinolin-2(1H)-one | 423.1 |
| 113 | 4-amino-6-chloro-3-{5-[3-(dimethylamino)pyrrolidin-1-yl]-6-fluoro-1H-benzimidazol-2-yl}quinolin-2(1H)-one | 441 |
| 114 | 4-amino-5-[(2R,6S)-2,6-dimethylmorpholin-4-yl]-3-(3H-imidazo[4,5-b]pyridin-2-yl)quinolin-2(1H)-one | 391.2 |
| 115 | 4-amino-3-(6-thiomorpholin-4-yl-1H-benzimidazol-2-yl)quinolin-2(1H)-one | 378.4 |
| 116 | 4-amino-3-[5-(4-cyclohexylpiperazin-1-yl)-1H-benzimidazol-2-yl]quinolin-2(1H)-one | 443.1 |
| 117 | 4-amino-3-{6-[3-(diethylamino)pyrrolidin-1-yl]-1H-benzimidazol-2-yl}quinolin-2(1H)-one | 417.1 |
| 118 | 4-amino-3-[6-(4-pyridin-2-ylpiperazin-1-yl)-1H-benzimidazol-2-yl]quinolin-2(1H)-one | 438.3 |
| 119 | 4-amino-3-[5-(4-methylpiperazin-1-yl)-3H-imidazo[4,5-b]pyridin-2-yl]quinolin-2(1H)-one | 376.3 |
| 120 | 4-amino-6-chloro-3-[5-(4-methylpiperazin-1-yl)-1H-imidazo[4,5-b]pyridin-2-yl]quinolin-2(1H)-one | 410.2 |
| 121 | 2-(4-amino-2-oxo-1,2-dihydroquinolin-3-yl)-N-methyl-N-(1-methylpiperidin-4-yl)-1H-benzimidazole-5-carboxamide | 431.3 |
| 122 | 4-amino-3-(5-{[4-(1-methylethyl)piperazin-1-yl]carbonyl}-1H-benzimidazol-2-yl)quinolin-2(1H)-one | 431.3 |
| 123 | 4-amino-3-[5-(4-methylpiperazin-1-yl)-1H-benzimidazol-2-yl]-6-nitroquinolin-2(1H)-one | 420.2 |
| 124 | 4-amino-3-[5-(1,4'-bipiperidin-1'-ylcarbonyl)-1H-benzimidazol-2-yl]quinolin-2(1H)-one | 471.1 |
| 125 | 4-amino-3-{5-[(4-methylpiperazin-1-yl)carbonyl]-1H-benzimidazol-2-yl}quinolin-2(1H)-one | 403.3 |
| 126 | 4-amino-3-[5-(1-oxidothiomorpholin-4-yl)-1H-benzimidazol-2-yl]quinolin-2(1H)-one | 394.5 |
| 127 | 3-{5-[(4-acetylpiperazin-1-yl)carbonyl]-1H-benzimidazol-2-yl}-4-aminoquinolin-2(1H)-one | 431.3 |
| 128 | 4-amino-3-(5-{[(3R)-3-(dimethylamino)pyrrolidin-1-yl]carbonyl}-1H-benzimidazol-2-yl)quinolin-2(1H)-one | 417.4 |
| 129 | 4-amino-3-(5-{[(3S)-3-(dimethylamino)pyrrolidin-1-yl]carbonyl}-1H-benzimidazol-2-yl)quinolin-2(1H)-one | 417.4 |
| 130 | 4-amino-3-(5-{[4-(dimethylamino)piperidin-1-yl]carbonyl}-1H-benzimidazol-2-yl)quinolin-2(1H)-one | 431.4 |
| 131 | methyl 2-(4-amino-5-fluoro-2-oxo-1,2-dihydroquinolin-3-yl)-1H-benzimidazole-6-carboxylate | 353.2 |
| 132 | 4-amino-3-[5-(1,3'-bipyrrolidin-1'-yl)-1H-benzimidazol-2-yl]quinolin-2(1H)-one | 415.5 |
| 133 | 4-amino-3-[5-(pyridin-3-yloxy)-1H-benzimidazol-2-yl]quinolin-2(1H)-one | 370.2 |
| 134 | 4-amino-5,6-bis(methyloxy)-3-[5-(4-methylpiperazin-1-yl)-1H-benzimidazol-2-yl]quinolin-2(1H)-one | 435.5 |
| 135 | 2-(4-amino-2-oxo-1,2-dihydroquinolin-3-yl)-N-[2-(dimethylamino)ethyl]-N-methyl-1H-benzimidazole-5-carboxamide | 405.3 |
| 136 | 2-(4-amino-2-oxo-1,2-dihydroquinolin-3-yl)-N-methyl-N-(1-methylpyrrolidin-3-yl)-1H-benzimidazole-5-carboxamide | 417.2 |
| 137 | 4-amino-3-{5-[(5-methyl-2,5-diazabicyclo[2.2.1]hept-2-yl)carbonyl]-1H-benzimidazol-2-yl}quinolin-2(1H)-one | 415.2 |
| 138 | 4-amino-3-{5-[(4-cyclohexylpiperazin-1-yl)carbonyl]-1H-benzimidazol-2-yl}quinolin-2(1H)-one | 471.6 |
| 139 | 4-amino-3-{5-[(2-piperidin-1-ylethyl)amino]-1H-benzimidazol-2-yl}quinolin-2(1H)-one | 403.2 |
| 140 | ethyl 4-{[2-(4-amino-2-oxo-1,2-dihydroquinolin-3-yl)-1H-benzimidazol-5-yl]amino}piperidine-1-carboxylate | 447.3 |

-continued

| Example | Name | LC/MS m/z (MH+) |
|---|---|---|
| 141 | 4-amino-3-[5-({(5R)-5-[(methyloxy)methyl]pyrrolidin-3-yl}amino)-1H-benzimidazol-2-yl]quinolin-2(1H)-one | 405.2 |
| 142 | 4-amino-3-{5-[(pyridin-2-ylmethyl)amino]-1H-benzimidazol-2-yl}quinolin-2(1H)-one | 383.3 |
| 143 | 4-amino-3-[5-(piperidin-3-ylamino)-1H-benzimidazol-2-yl]quinolin-2(1H)-one | 375.2 |
| 144 | 4-amino-5-fluoro-3-{5-[(pyridin-2-ylmethyl)amino]-1H-benzimidazol-2-yl}quinolin-2(1H)-one | 401.3 |
| 145 | ethyl 4-{[2-(4-amino-5-fluoro-2-oxo-1,2-dihydroquinolin-3-yl)-1H-benzimidazol-5-yl]amino}piperidine-1-carboxylate | 465.5 |
| 146 | 4-amino-5-fluoro-3-[5-(piperidin-3-ylamino)-1H-benzimidazol-2-yl]quinolin-2(1H)-one | 393.3 |
| 147 | 4-amino-3-(1H-benzimidazol-2-yl)-6-bromoquinolin-2(1H)-one | 357.1 |
| 148 | 4-amino-3-(1H-benzimidazol-2-yl)-7-bromoquinolin-2(1H)-one | 357.1 |
| 149 | 4-amino-3-(5-bromo-1H-benzimidazol-2-yl)quinolin-2(1H)-one | 357.1 |
| 150 | N,N-dimethyl-2-(2-oxo-1,2-dihydroquinolin-3-yl)-1H-benzimidazole-5-carboxamide | 333.1 |
| 151 | 4-amino-3-(5-thien-2-yl-1H-benzimidazol-2-yl)quinolin-2(1H)-one | 359.2 |
| 152 | 2-(4-amino-2-oxo-1,2-dihydroquinolin-3-yl)-N,N-dimethyl-1H-benzimidazole-5-sulfonamide | 384.1 |
| 153 | 4-amino-6-iodo-3-[5-(4-methylpiperazin-1-yl)-1H-benzimidazol-2-yl]quinolin-2(1H)-one | 501.1 |
| 154 | 4-amino-3-(5-{2-[(dimethylamino)methyl]-morpholin-4-yl}-1H-benzimidazol-2-yl)quinolin-2(1H)-one | 419.2 |

Examples 155-270

Examples 155 to 270 shown in the following Table were synthesized using the methods described above such as Methods 1-15 and those set forth in the Schemes and other Examples or modified as apparent to one of reasonable skill in the art using commercially available materials.

| Example | Name | LC/MS m/z (MH+) |
|---|---|---|
| 155 | 4-[(3R)-1-azabicyclo[2.2.2]oct-3-ylamino]-3-(1H-benzimidazol-2-yl)-7-chloro-6-iodoquinolin-2(1H)-one | 547 |
| 156 | 4-[(3R)-1-azabicyclo[2.2.2]oct-3-ylamino]-3-(1H-benzimidazol-2-yl)-6-nitroquinolin-2(1H)-one | 431 |
| 157 | 4-[(3R)-1-azabicyclo[2.2.2]oct-3-ylamino]-3-(1H-benzimidazol-2-yl)-6-methylquinolin-2(1H)-one | 401 |
| 158 | 4-[(3R)-1-azabicyclo[2.2.2]oct-3-ylamino]-3-(1H-benzimidazol-2-yl)-6,7-difluoroquinolin-2(1H)-one | 422 |
| 159 | 4-[(3S)-1-azabicyclo[2.2.2]oct-3-ylamino]-3-(1H-benzimidazol-2-yl)-7-chloroquinolin-2(1H)-one | 421 |
| 160 | 4-[(3R)-1-azabicyclo[2.2.2]oct-3-ylamino]-3-(1H-benzimidazol-2-yl)-6-bromoquinolin-2(1H)-one | 465 |
| 161 | 4-[(3R)-1-azabicyclo[2.2.2]oct-3-ylamino]-3-(1H-benzimidazol-2-yl)-2-oxo-1,2-dihydroquinoline-6-carbonitrile | 411 |
| 162 | 4-[(3R)-1-azabicyclo[2.2.2]oct-3-ylamino]-3-(1H-benzimidazol-2-yl)-6-fluoroquinolin-2(1H)-one | 404 |
| 163 | 4-[(3S)-1-azabicyclo[2.2.2]oct-3-ylamino]-3-(1H-benzimidazol-2-yl)-6,7-bis(methyloxy)quinolin-2(1H)-one | 447 |
| 164 | 4-[(3R)-1-azabicyclo[2.2.2]oct-3-ylamino]-3-(1H-benzimidazol-2-yl)-6,7-dichloroquinolin-2(1H)-one | 455 |
| 165 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxamide | 531 |
| 166 | 4-[(3S)-1-azabicyclo[2.2.2]oct-3-ylamino]-3-(1H-benzimidazol-2-yl)-6-fluoro-7-[(3-hydroxypropyl)amino]quinolin-2(1H)-one | 478 |
| 167 | 4-[(3S)-1-azabicyclo[2.2.2]oct-3-ylamino]-3-(1H-benzimidazol-2-yl)-7-(dimethylamino)-6-fluoroquinolin-2(1H)-one | 448 |
| 168 | 4-[(3R)-1-azabicyclo[2.2.2]oct-3-ylamino]-3-(1H-benzimidazol-2-yl)-5-fluoroquinolin-2(1H)-one | 404 |
| 169 | 4-[(3R)-1-azabicyclo[2.2.2]oct-3-ylamino]-3-(1H-benzimidazol-2-yl)-6-(4-nitrophenyl)quinolin-2(1H)-one | 508 |
| 170 | 4-[(3R)-1-azabicyclo[2.2.2]oct-3-ylamino]-3-(1H-benzimidazol-2-yl)-7-{[2-(dimethylamino)ethyl]amino}-6-fluoroquinolin-2(1H)-one | 491 |
| 171 | 4-[(3S)-1-azabicyclo[2.2.2]oct-3-ylamino]-3-(1H-benzimidazol-2-yl)-6-fluoro-7-(1H-imidazol-1-yl)quinolin-2(1H)-one | 471 |
| 172 | 4-[(3R)-1-azabicyclo[2.2.2]oct-3-ylamino]-3-(1H-benzimidazol-2-yl)-6-[4-(methyloxy)phenyl]quinolin-2(1H)-one | 493 |
| 173 | 4-[(3S)-1-azabicyclo[2.2.2]oct-3-ylamino]-3-(1H-benzimidazol-2-yl)-6-fluoro-7-morpholin-4-ylquinolin-2(1H)-one | 490 |
| 174 | 4-[(3R)-1-azabicyclo[2.2.2]oct-3-ylamino]-6,7-difluoro-3-(3H-imidazo[4,5-b]pyridin-2-yl)quinolin-2(1H)-one | 423 |
| 175 | 4-[(3R)-1-azabicyclo[2.2.2]oct-3-ylamino]-3-(1H-benzimidazol-2-yl)-6-(3-nitrophenyl)quinolin-2(1H)-one | 508 |
| 176 | 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxamide | 531 |
| 177 | 4-[(3S)-1-azabicyclo[2.2.2]oct-3-ylamino]-3-(1H-benzimidazol-2-yl)-5-methylquinolin-2(1H)-one | 401 |
| 178 | 6-(3-acetylphenyl)-4-[(3R)-1-azabicyclo[2.2.2]oct-3-ylamino]-3-(3H-imidazo[4,5-b]pyridin-2-yl)quinolin-2(1H)-one | 506 |
| 179 | 4-[(3S)-1-azabicyclo[2.2.2]oct-3-ylamino]-3-(1H-benzimidazol-2-yl)-5-chloroquinolin-2(1H)-one | 421 |
| 180 | 4-[(3R)-1-azabicyclo[2.2.2]oct-3-ylamino]-6-fluoro-3-(3H-imidazo[4,5-b]pyridin-2-yl)-7-morpholin-4-ylquinolin-2(1H)-one | 491 |
| 181 | 4-[(3S)-1-azabicyclo[2.2.2]oct-3-ylamino]-3-(1H-benzimidazol-2-yl)-7-(cyclopropylamino)-6-fluoroquinolin-2(1H)-one | 460 |
| 182 | N-{3-[4-[(3R)-1-azabicyclo[2.2.2]oct-3-ylamino]-3-(3H-imidazo[4,5-b]pyridin-2-yl)-2-oxo-1,2-dihydroquinolin-6-yl]phenyl}acetamide | 521 |
| 183 | 4-[(3S)-1-azabicyclo[2.2.2]oct-3-ylamino]-3-(1H-benzimidazol-2-yl)-6-fluoro-7-(4-methylpiperazin-1-yl)quinolin-2(1H)-one | 503 |
| 184 | 4-[(3R)-1-azabicyclo[2.2.2]oct-3-ylamino]-6-fluoro-7-(1H-imidazol-1-yl)-3-(3H-imidazo[4,5-b]pyridin-2-yl)quinolin-2(1H)-one | 472 |

-continued

| Example | Name | LC/MS m/z (MH+) |
|---|---|---|
| 185 | 4-[(3S)-1-azabicyclo[2.2.2]oct-3-ylamino]-3-(1H-benzimidazol-2-yl)-6-fluoro-7-[(2-pyridin-2-ylethyl)amino]quinolin-2(1H)-one | 525 |
| 186 | 4-[(3S)-1-azabicyclo[2.2.2]oct-3-ylamino]-3-(1H-benzimidazol-2-yl)-6-fluoro-7-piperidin-1-ylquinolin-2(1H)-one | 488 |
| 187 | 6-chloro-3-(3H-imidazo[4,5-b]pyridin-2-yl)quinolin-2(1H)-one | 298 |
| 188 | ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxylate | 560 |
| 189 | 4-[(3R)-1-azabicyclo[2.2.2]oct-3-ylamino]-3-(1H-benzimidazol-2-yl)-6-(1-benzothien-2-yl)quinolin-2(1H)-one | 519 |
| 190 | 4-[(3S)-1-azabicyclo[2.2.2]oct-3-ylamino]-3-(1H-benzimidazol-2-yl)-6-fluoro-7-pyrrolidin-1-ylquinolin-2(1H)-one | 474 |
| 191 | 4-[(3R)-1-azabicyclo[2.2.2]oct-3-ylamino]-3-(3H-imidazo[4,5-b]pyridin-2-yl)-6-[2-trifluoromethyl)phenyl]quinolin-2(1H)-one | 532 |
| 192 | 4-[(3R)-1-azabicyclo[2.2.2]oct-3-ylamino]-3-(3H-imidazo[4,5-b]pyridin-2-yl)-6-[2-(methyloxy)phenyl]quinolin-2(1H)-one | 494 |
| 193 | ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxylate | 560 |
| 194 | 4-[(3R)-1-azabicyclo[2.2.2]oct-3-ylamino]-3-(1H-benzimidazol-2-yl)-6-(4-ethylphenyl)quinolin-2(1H)-one | 491 |
| 195 | 4-[(3S)-1-azabicyclo[2.2.2]oct-3-ylamino]-3-(1H-benzimidazol-2-yl)-6-fluoro-7-[(2-methylpropyl)amino]quinolin-2(1H)-one | 476 |
| 196 | 4-[(3R)-1-azabicyclo[2.2.2]oct-3-ylamino]-3-(1H-benzimidazol-2-yl)-5-methylquinolin-2(1H)-one | 401 |
| 197 | 4-[(3R)-1-azabicyclo[2.2.2]oct-3-ylamino]-6-(2,4-dichlorophenyl)-3-(3H-imidazo[4,5-b]pyridin-2-yl)quinolin-2(1H)-one | 532 |
| 198 | 4-[(3R)-1-azabicyclo[2.2.2]oct-3-ylamino]-3-(1H-benzimidazol-2-yl)-6-[3-(trifluoromethyl)phenyl]quinolin-2(1H)-one | 531 |
| 199 | 3-(1H-benzimidazol-2-yl)-4-(dimethylamino)quinolin-2(1H)-one | 305 |
| 200 | 4-hydroxy-3-(1H-imidazo[4,5-f]quinolin-2-yl)quinolin-2(1H)-one | 329 |
| 201 | 4-hydroxy-3-(1H-imidazo[4,5-b]pyridin-2-yl)quinolin-2(1H)-one | 279 |
| 202 | 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid | 525 |
| 203 | 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzamide | 524 |
| 204 | N-{3-[4-[(3R)-1-azabicyclo[2.2.2]oct-3-ylamino]-3-(1H-benzimidazol-2-yl)-5-fluoro-2-oxo-1,2-dihydroquinolin-6-yl]phenyl}acetamide | 538 |
| 205 | 3-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid | 525 |
| 206 | 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoic acid | 525 |
| 207 | N-{3-[4-[(3R)-1-azabicyclo[2.2.2]oct-3-ylamino]-3-(1H-benzimidazol-2-yl)-7-fluoro-2-oxo-1,2-dihydroquinolin-6-yl]phenyl}acetamide | 538 |
| 208 | 4-[(3R)-1-azabicyclo[2.2.2]oct-3-ylamino]-3-(1H-benzimidazol-2-yl)-7-chloro-6-(2-methylphenyl)quinolin-2(1H)-one | 511 |
| 209 | 4-[(3R)-1-azabicyclo[2.2.2]oct-3-ylamino]-3-(1H-benzimidazol-2-yl)-2-oxo-1,2-dihydroquinoline-7-carbonitrile | 411 |
| 210 | 4-[(3R)-1-azabicyclo[2.2.2]oct-3-ylamino]-3-(1H-benzimidazol-2-yl)-7-(methyloxy)quinolin-2(1H)-one | 417 |
| 211 | 4-[4-[(3R)-1-azabicyclo[2.2.2]oct-3-ylamino]-3-(1H-benzimidazol-2-yl)-2-oxo-1,2-dihydroquinolin-7-yl]benzamide | 506 |
| 212 | 4-[(3R)-1-azabicyclo[2.2.2]oct-3-ylamino]-3-(1H-benzimidazol-2-yl)-6-fluoro-7-(methyloxy)quinolin-2(1H)-one | 434 |
| 213 | 4-[(3R)-1-azabicyclo[2.2.2]oct-3-ylamino]-3-(1H-benzimidazol-2-yl)-6-chloro-7-(dimethylamino)quinolin-2(1H)-one | 464 |
| 214 | 4-[(3R)-1-azabicyclo[2.2.2]oct-3-ylamino]-3-(1H-benzimidazol-2-yl)-7-(dimethylamino)-6-iodoquinolin-2(1H)-one | 555 |
| 215 | 3-[4-[(3R)-1-azabicyclo[2.2.2]oct-3-ylamino]-3-(1H-benzimidazol-2-yl)-7-(1H-imidazol-1-yl)-2-oxo-1,2-dihydroquinolin-6-yl]benzoic acid | 573 |
| 216 | 4-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]benzoic acid | 590 |
| 217 | 4-[(3R)-1-azabicyclo[2.2.2]oct-3-ylamino]-3-(1H-benzimidazol-2-yl)-7-(methyloxy)-6-[4-(methylsulfonyl)phenyl]quinolin-2(1H)-one | 571 |
| 218 | 4-[(3R)-1-azabicyclo[2.2.2]oct-3-ylamino]-3-(1H-benzimidazol-2-yl)-8-methylquinolin-2(1H)-one | 401 |
| 219 | 4-[(3S)-1-azabicyclo[2.2.2]oct-3-ylamino]-3-(1H-benzimidazol-2-yl)-6,7-difluoroquinolin-2(1H)-one | 422 |
| 220 | 3-(1H-benzimidazol-2-yl)-6-methyl-4-(piperidin-3-ylamino)quinolin-2(1H)-one | 374 |
| 221 | 4-[(3S)-1-azabicyclo[2.2.2]oct-3-ylamino]-3-(1H-benzimidazol-2-yl)-6-[2-(methyloxy)phenyl]quinolin-2(1H)-one | 493 |
| 222 | 4-[(3S)-1-azabicyclo[2.2.2]oct-3-ylamino]-3-(1H-benzimidazol-2-yl)-6-[3-(methyloxy)phenyl]quinolin-2(1H)-one | 493 |
| 223 | 3-(1H-benzimidazol-2-yl)-6,7-difluoro-4-(piperidin-4-ylamino)quinolin-2(1H)-one | 396 |
| 224 | 3-(1H-benzimidazol-2-yl)-6,7-difluoro-4-(pyrrolidin-3-ylamino)quinolin-2(1H)-one | 382 |
| 225 | 3-(1H-benzimidazol-2-yl)-6-chloro-4-[(3-morpholin-4-ylpropyl)amino]quinolin-2(1H)-one | 439 |
| 226 | 6-chloro-3-(5-morpholin-4-yl-1H-benzimidazol-2-yl)-4-(piperidin-4-ylamino)quinolin-2(1H)-one | 480 |
| 227 | 6-chloro-3-(5-morpholin-4-yl-1H-benzimidazol-2-yl)-4-[(piperidin-2-ylmethyl)amino]quinolin-2(1H)-one | 494 |
| 228 | 4-[(3S)-1-azabicyclo[2.2.2]oct-3-ylamino]-6-chloro-3-(5-morpholin-4-yl-1H-benzimidazol-2-yl)quinolin-2(1H)-one | 506 |
| 229 | 6-chloro-3-(5-morpholin-4-yl-1H-benzimidazol-2-yl)-4-(piperidin-3-ylamino)quinolin-2(1H)-one | 480 |
| 230 | 6-chloro-4-{[2-(dimethylamino)ethyl]amino}-3-(5-morpholin-4-yl-1H-benzimidazol-2-yl)quinolin-2(1H)-one | 468 |
| 231 | 4-[(3R)-1-azabicyclo[2.2.2]oct-3-ylamino]-6-chloro-3-(5-morpholin-4-yl-1H-benzimidazol-2-yl)quinolin-2(1H)-one | 506 |
| 232 | 6-chloro-3-(5-morpholin-4-yl-1H-benzimidazol-2-yl)-4-[(piperidin-3-ylmethyl)amino]quinolin-2(1H)-one | 494 |
| 233 | 6-chloro-3-(5-morpholin-4-yl-1H-benzimidazol-2-yl)-4-[(piperidin-4-ylmethyl)amino]quinolin-2(1H)-one | 494 |
| 234 | 4-{[(1R,2R)-2-aminocyclohexyl]amino}-6-chloro-3-(5-morpholin-4-yl-1H-benzimidazol-2-yl)quinolin-2(1H)-one | 494 |

-continued

| Example | Name | LC/MS m/z (MH+) |
|---|---|---|
| 235 | 4-[(4-aminocyclohexyl)amino]-6-chloro-3-(5-morpholin-4-yl-1H-benzimidazol-2-yl)quinolin-2(1H)-one | 494 |
| 236 | 4-{[(2S)-2-amino-3-methylbutyl]amino}-6-chloro-3-(5-morpholin-4-yl-1H-benzimidazol-2-yl)quinolin-2(1H)-one | 482 |
| 237 | 4-({[4-(aminomethyl)phenyl]methyl}amino)-6-chloro-3-(5-morpholin-4-yl-1H-benzimidazol-2-yl)quinolin-2(1H)-one | 516 |
| 238 | 6-chloro-3-(5-morpholin-4-yl-1H-benzimidazol-2-yl)-4-[(pyrrolidin-2-ylmethyl)amino]quinolin-2(1H)-one | 480 |
| 239 | 4-{[(1R)-1-(aminomethyl)propyl]amino}-6-chloro-3-(5-morpholin-4-yl-1H-benzimidazol-2-yl)quinolin-2(1H)-one | 468 |
| 240 | 4-{[(1S)-2-amino-1-(phenylmethyl)ethyl]amino}-6-chloro-3-(5-morpholin-4-yl-1H-benzimidazol-2-yl)quinolin-2(1H)-one | 530 |
| 241 | 6-chloro-4-{[3-(4-methylpiperazin-1-yl)propyl]amino}-3-(5-morpholin-4-yl-1H-benzimidazol-2-yl)quinolin-2(1H)-one | 537 |
| 242 | 6-chloro-3-(5-morpholin-4-yl-1H-benzimidazol-2-yl)-4-{[1-(phenylmethyl)piperidin-4-yl]amino}quinolin-2(1H)-one | 570 |
| 243 | 6-chloro-3-(5-morpholin-4-yl-1H-benzimidazol-2-yl)-4-[(3-morpholin-4-ylpropyl)amino]quinolin-2(1H)-one | 524 |
| 244 | 6-chloro-3-(5-morpholin-4-yl-1H-benzimidazol-2-yl)-4-[(2-piperidin-1-ylethyl)amino]quinolin-2(1H)-one | 508 |
| 245 | 6-chloro-3-(5-morpholin-4-yl-1H-benzimidazol-2-yl)-4-[(pyridin-3-ylmethyl)amino]quinolin-2(1H)-one | 488 |
| 246 | 6-chloro-4-{[3-(1H-imidazol-1-yl)propyl]amino}-3-(5-morpholin-4-yl-1H-benzimidazol-2-yl)quinolin-2(1H)-one | 505 |
| 247 | 6-chloro-3-(5-morpholin-4-yl-1H-benzimidazol-2-yl)-4-[(pyridin-4-ylmethyl)amino]quinolin-2(1H)-one | 488 |
| 248 | 6-chloro-4-{[2-(methylamino)ethyl]amino}-3-(5-morpholin-4-yl-1H-benzimidazol-2-yl)quinolin-2(1H)-one | 454 |
| 249 | 6-chloro-4-{[(2-methyl-1-piperidin-4-yl-1H-benzimidazol-5-yl)methyl]amino}-3-(5-morpholin-4-yl-1H-benzimidazol-2-yl)quinolin-2(1H)-one | 624 |
| 250 | 6-chloro-3-(5-morpholin-4-yl-1H-benzimidazol-2-yl)-4-[(2-pyrrolidin-1-ylethyl)amino]quinolin-2(1H)-one | 494 |
| 251 | 6-chloro-3-(5-morpholin-4-yl-1H-benzimidazol-2-yl)-4-(pyrrolidin-3-ylamino)quinolin-2(1H)-one | 466 |
| 252 | 4-{[(1R,2R)-2-aminocyclohexyl]amino}-6-chloro-3-[5-(4-methylpiperazin-1-yl)-1H-benzimidazol-2-yl]quinolin-2(1H)-one | 507 |
| 253 | 4-[(4-aminocyclohexyl)amino]-6-chloro-3-[5-(4-methylpiperazin-1-yl)-1H-benzimidazol-2-yl]quinolin-2(1H)-one | 507 |
| 254 | 4-({[4-(aminomethyl)phenyl]methyl}amino)-6-chloro-3-[5-(4-methylpiperazin-1-yl)-1H-benzimidazol-2-yl]quinolin-2(1H)-one | 529 |
| 255 | 6-chloro-4-{[2-(methylamino)ethyl]amino}-3-[5-(4-methylpiperazin-1-yl)-1H-benzimidazol-2-yl]quinolin-2(1H)-one | 467 |
| 256 | 6-chloro-3-[5-(4-methylpiperazin-1-yl)-1H-benzimidazol-2-yl]-4-{[3-(4-methylpiperazin-1-yl)propyl]amino}quinolin-2(1H)-one | 550 |
| 257 | 6-chloro-3-[5-(4-methylpiperazin-1-yl)-1H-benzimidazol-2-yl]-4-{[1-(phenylmethyl)piperidin-4-yl]amino}quinolin-2(1H)-one | 583 |
| 258 | 6-chloro-3-[5-(4-methylpiperazin-1-yl)-1H-benzimidazol-2-yl]-4-[(2-pyrrolidin-1-ylethyl)amino]quinolin-2(1H)-one | 507 |
| 259 | 6-chloro-3-[5-(4-methylpiperazin-1-yl)-1H-benzimidazol-2-yl]-4-(pyrrolidin-3-ylamino)quinolin-2(1H)-one | 479 |
| 260 | 6-chloro-3-[5-(4-methylpiperazin-1-yl)-1H-benzimidazol-2-yl]-4-(piperidin-4-ylamino)quinolin-2(1H)-one | 493 |
| 261 | 6-chloro-3-(5-morpholin-4-yl-1H-benzimidazol-2-yl)-4-[(2-piperidin-2-ylethyl)amino]quinolin-2(1H)-one | 508 |
| 262 | 4-[(3S)-1-azabicyclo[2.2.2]oct-3-ylamino]-7-chloro-3-(5-morpholin-4-yl-1H-benzimidazol-2-yl)quinolin-2(1H)-one | 506 |
| 263 | 7-chloro-3-(5-morpholin-4-yl-1H-benzimidazol-2-yl)-4-(piperidin-3-ylamino)quinolin-2(1H)-one | 480 |
| 264 | 6-chloro-3-[5-(4-methylpiperazin-1-yl)-1H-benzimidazol-2-yl]-4-[(piperidin-2-ylmethyl)amino]quinolin-2(1H)-one | 507 |
| 265 | 6-chloro-3-[5-(4-methylpiperazin-1-yl)-1H-benzimidazol-2-yl]-4-{[(2S)-pyrrolidin-2-ylmethyl]amino}quinolin-2(1H)-one | 493 |
| 266 | 6-chloro-3-[5-(4-methylpiperazin-1-yl)-1H-benzimidazol-2-yl]-4-{[(2R)-pyrrolidin-2-ylmethyl]amino}quinolin-2(1H)-one | 493 |
| 267 | 6-chloro-4-({[(2S)-1-ethylpyrrolidin-2-yl]methyl}amino)-3-[5-(4-methylpiperazin-1-yl)-1H-benzimidazol-2-yl]quinolin-2(1H)-one | 521 |
| 268 | 6-chloro-4-({[(2R)-1-ethylpyrrolidin-2-yl]methyl}amino)-3-[5-(4-methylpiperazin-1-yl)-1H-benzimidazol-2-yl]quinolin-2(1H)-one | 521 |
| 269 | 4-[(3S)-1-azabicyclo[2.2.2]oct-3-ylamino]-3-(1H-benzimidazol-2-yl)-6-[4-(methyloxy)phenyl]quinolin-2(1H)-one | 493 |
| 270 | 6-(3-aminophenyl)-4-[(3S)-1-azabicyclo[2.2.2]oct-3-ylamino]-3-(1H-benzimidazol-2-yl)quinolin-2(1H)-one | 478 |

Assay Procedures

In Vitro Kinase Assays for Receptor Tyrosine Kinases

The kinase activity of various protein tyrosine kinases can be measured by providing ATP and a suitable peptide or protein tyrosine-containing substrate, and assaying the transfer of phosphate moiety to the tyrosine residue. Recombinant proteins corresponding to the cytoplasmic domains of the flt-1 (VEGFR1), KDR (VEGFR2), and bFGF receptors were expressed in Sf9 insect cells using a Baculovirus expression system (InVitrogen) and purified via Glu antibody interaction (for Glu-epitope tagged constructs) or by Metal Ion Chromatography (for $His_6$ tagged constructs). For each assay, test compounds were serially diluted in DMSO then mixed with an appropriate kinase reaction buffer plus ATP. Kinase protein and an appropriate biotinylated peptide substrate were added to give a final volume of 100 μL, reactions were incubated for 1-2 hours at room temperature and stopped by the addition of 50 μL of 45 mM EDTA, 50 mM Hepes pH 7.5. Stopped reaction mix (75 μL) was transferred to a streptavidin coated microtiter plate (Boehringer Mannheim) and incubated for 1 hour. Phosphorylated peptide product was measured with the DELFIA time-resolved fluorescence system (Wallac), using a Eu-labeled anti-phosphotyrosine antibody PT66 with the modification that the DELFIA assay buffer was supplemented with 1 mM $MgCl_2$ for the antibody dilution.

Time resolved fluorescence was read on a Wallac 1232 DELFIA fluorometer. The concentration of each compound for 50% inhibition ($IC_{50}$) was calculated by non-linear regression using XL Fit data analysis software.

Flt-1, KDR, and bFGFR kinases were assayed in 50 mM Hepes pH 7.0, 2 mM $MgCl_2$, 10 mM $MnCl_2$, 1 mM NaF, 1 mM DTT, 1 mg/ml BSA, 2 μM ATP, and 0.42 μM biotin-GGGGQDGKDYIVLPI-$NH_2$. Flt-1, KDR, and bFGFR kinases were added at 0.1 μg/mL, 0.05 μg/mL, or 0.1 μg/mL respectively.

Each of the following compounds was synthesized and assayed using the procedures described above:

3-{5-[2-(ethylanilino)ethoxy]-1H-benzimidazol-2-yl}-4-hydroxy-2(1H)-quinolinone; 3-[5-(4-aminophenoxy)-1H-benzimidazol-2-yl]-4-hydroxy-2(1H)-quinolinone; 3-{6-[[2-(dimethylamino)ethyl](methyl)amino]-1H-benzimidazol-2-yl}-4-hydroxy-2(1H)-quinolinone; 4-hydroxy-3-[5-(4-morpholinyl)-1H-benzimidazol-2-yl]-2(1H)-quinolinone; 3-[5-(3-amino-1-pyrrolidinyl)-1H-benzimidazol-2-yl]-4-hydroxy-2(1H)-quinolinone; N,N-dimethyl-2-(2-oxo-1,2-dihydro-3-quinolinyl)-1H-benzimidazole-5-carboxamide; 3-{5-[2-(4-morpholinyl)ethoxy]-1H-benzimidazol-2-yl}-2(1H)-quinolinone; 3-{5-[3-(dimethylamino)-1-pyrrolidinyl]-1H-benzimidazol-2-yl}-2(1H)-quinolinone; 3-(1H-benzimidazol-2-yl)-2-oxo-1,2-dihydro-4-quinolinecarbonitrile; 4-amino-3-{5-[2-(4-morpholinyl)ethoxy]-1H-benzimidazol-2-yl}-2(1H)-quinolinone; 4-amino-3-[6-(4-morpholinyl)-1H-benzimidazol-2-yl]-2(1H)-quinolinone; 4-amino-3-[6-(3-amino-1-pyrrolidinyl)-1H-benzimidazol-2-yl]-2(1H)-quinolinone; 2-(4-amino-2-oxo-1,2-dihydro-3-quinolinyl)-1H-benzimidazole-5-carbonitrile; 2-(4-amino-2-oxo-1,2-dihydro-3-quinolinyl)-N,N-dimethyl-1H-benzimidazole-5-carboxamide; 4-amino-3-{5-[3-(dimethylamino)-1-pyrrolidinyl]-1H-benzimidazol-2-yl}-2(1H)-quinolinone; 2-(4-amino-2-oxo-1,2-dihydro-3-quinolinyl)-1H-benzimidazole-6-carboximidamide; 4-amino-3-[5-(4-morpholinylcarbonyl)-1H-benzimidazol-2-yl]-2(1H)-quinolinone; 4-amino-3-[5-(1H-1,2,4-triazol-1-yl)-1H-benzimidazol-2-yl]-2(1H)-quinolinone; 4-amino-3-[5-(dimethylamino)-1H-benzimidazol-2-yl]-2(1H)-quinolinone; 4-amino-3-[5-(1-piperidinyl)-1H-benzimidazol-2-yl]-2(1H)-quinolinone; 4-amino-3-[5-(2-thienyl)-1H-benzimidazol-2-yl]-2(1H)-quinolinone; 4-amino-3-{5-[3-(1-pyrrolidinyl)propoxy]-1H-benzimidazol-2-yl}-2(1H)-quinolinone; 4-amino-3-{5-[3-(4-morpholinyl)propoxy]-1H-benzimidazol-2-yl}-2(1H)-quinolinone; 4-amino-3-[5-(3,5-dimethyl-1-piperazinyl)-1H-benzimidazol-2-yl]-2(1H)-quinolinone; 4-amino-3-[5-(2,6-dimethyl-4-morpholinyl)-1H-benzimidazol-2-yl]-2(1H)-quinolinone; 4-amino-3-[5-(4-methyl-1-piperazinyl)-1H-benzimidazol-2-yl]-2(1H)-quinolinone; 4-amino-3-(1H-benzimidazol-2-yl)-6-[hydroxy(oxido)amino]-2(1H)-quinolinone; 4-amino-3-(1H-benzimidazol-2-yl)-5-[2-(4-morpholinyl)ethoxy]-2(1H)-quinolinone; 4-amino-3-(1H-benzimidazol-2-yl)-6-(4-methyl-1-piperazinyl)-2(1H)-quinolinone; 4-amino-3-(1H-benzimidazol-2-yl)-5-[(1-methyl-3-piperidinyl)oxy]-2(1H)-quinolinone; 4-amino-6-chloro-3-[5-(4-morpholinyl)-1H-benzimidazol-2-yl]-2(1H)-quinolinone; 4-amino-6-chloro-3-{5-[3-(dimethylamino)-1-pyrrolidinyl]-1H-benzimidazol-2-yl}-2(1H)-quinolinone; 4-amino-6-[hydroxy(oxido)amino]-3-{5-[2-(4-morpholinyl)ethoxy]-1H-benzimidazol-2-yl}-2(1H)-quinolinone; 4-amino-5-[2-(4-morpholinyl)ethoxy]-3-{5-[2-(4-morpholinyl)ethoxy]-1H-benzimidazol-2-yl}-2(1H)-quinolinone; 4-amino-3-(1H-benzimidazol-2-yl)-6-(2-pyridinylmethoxy)-2(1H)-quinolinone; 4-amino-6-fluoro-3-[5-(4-morpholinyl)-1H-benzimidazol-2-yl]-2(1H)-quinolinone; 4-amino-3-{5-[3-(dimethylamino)-1-pyrrolidinyl]-1H-benzimidazol-2-yl}-6-fluoro-2(1H)-quinolinone; 3-(1H-benzimidazol-2-yl)-4-[(tetrahydro-2-furanylmethyl)amino]-2(1H)-quinolinone; 3-(1H-benzimidazol-2-yl)-4-(methylamino)-2(1H)-quinolinone; 3-(1H-benzimidazol-2-yl)-4-(ethylamino)-2(1H)-quinolinone; 3-(1H-benzimidazol-2-yl)4-{[2-(1-methyl-2-pyrrolidinyl)ethyl]amino}-2(1H)-quinolinone; 3-(1H-benzimidazol-2-yl)-4-[(4-piperidinylmethyl)amino]-2(1H)-quinolinone; 3-(1H-benzimidazol-2-yl)-4-(4-fluoroanilino)-2(1H)-quinolinone; 4-(1-azabicyclo[2.2.2]oct-3-ylamino)-3-(1H-benzimidazol-2-yl)-2(1H)-quinolinone; 3-(1H-benzimidazol-2-yl)4-(1H-benzimidazol-6-ylamino)-2(1H)-quinolinone; 4-anilino-3-(1H-benzimidazol-2-yl)-2(1H)-quinolinone; 3-(1H-benzimidazol-2-yl)-4-(methoxyamino)-2(1H)-quinolinone; 3-(1H-benzimidazol-2-yl)-4-[(1H-imidazol-5-ylmethyl)amino]-2(1H)-quinolinone; 3-(1H-benzimidazol-2-yl)-4-(4-morpholinylamino)-2(1H)-quinolinone; 3-(1H-benzimidazol-2-yl)-4-hydrazino-2(1H)-quinolinone; 4-(1-azabicyclo[2.2.2]oct-3-ylamino)-3-(1H-benzimidazol-2-yl)-2(1H)-quinolinone; 4-(1-azabicyclo[2.2.2]oct-3-ylamino)-3-(1H-benzimidazol-2-yl)-2(1H)-quinolinone; 4-[(2-methoxyethyl)amino]-3-[6-(4-morpholinyl)-1H-benzimidazol-2-yl]-2(1H)-quinolinone; 4-[(2-hydroxyethyl)amino]-3-[5-(4-morpholinyl)-1H-benzimidazol-2-yl]-2(1H)-quinolinone; 4-(methoxyamino)-3-[5-(4-morpholinyl)-1H-benzimidazol-2-yl]-2(1H)-quinolinone; 3-[5-(4-morpholinyl)-1H-benzimidazol-2-yl]-4-(3-piperidinylamino)-2(1H)-quinolinone; 3-[5-(4-morpholinyl)-1H-benzimidazol-2-yl]-4-[(3-piperidinylmethyl)amino]-2(1H)-quinolinone; 4-{[2-(dimethylamino)ethyl]amino}-3-[5-(4-morpholinyl)-1H-benzimidazol-2-yl]-2(1H)-quinolinone; 3-[5-(4-morpholinyl)-1H-benzimidazol-2-yl]-4-[(tetrahydro-2-furanylmethyl)amino]-2(1H)-quinolinone; 4-{[2-(methylamino)ethyl]amino}-3-[5-(4-morpholinyl)-1H-benzimidazol-2-yl]-2(1H)-quinolinone; 3-[5-(4-morpholinyl)-1H-benzimidazol-2-yl]-4-(3-pyrrolidinylamino)-2(1H)-quinolinone; 4-[(2-amino-4-methylpentyl)amino]-3-[5-(4-morpholinyl)-1H-benzimidazol-2-yl]-2(1H)-quinolinone; 4-[(2-amino-3-methylbutyl)amino]-3-[5-(4-morpholinyl)-1H-benzimidazol-2-yl]-2(1H)-quinolinone; 3-(5,6-dimethyl-1H-benzimidazol-2-yl)-4-(3-piperidinylamino)-2(1H)-quinolinone; 4-[(2-aminocyclohexyl)amino]-3-[5-(4-morpholinyl)-1H-benzimidazol-2-yl]-2(1H)-quinolinone; 4-[(2-aminocyclohexyl)amino]-3-[5-(4-morpholinyl)-1H-benzimidazol-2-yl]-2(1H)-quinolinone; 3-(1H-benzimidazol-2-yl)-4-hydroxybenzo[g]quinolin-2(1H)-one; 4-amino-3-(3H-imidazo[4,5-b]pyridin-2-yl)quinolin-2(1H)-one; 4-amino-3-(5-morpholin-4-yl-3H-imidazo[4,5-b]pyridin-2-yl)quinolin-2(1H)-one; 4-amino-5-[(2R,6S)-2,6-dimethylmorpholin-4-yl]-3-(3H-imidazo[4,5-b]pyridin-2-yl)quinolin-2(1H)-one; 4-amino-3-{5-[3-(dimethylamino)pyrrolidin-1-yl]-3H-imidazo[4,5-b]pyridin-2-yl}quinolin-2(1H)-one; 4-amino-3-{5-[(3S)-3-(dimethylamino)pyrrolidin-1-yl]-1H-benzimidazol-2-yl}quinolin-2(1H)-one; 4-[(3S)-1-azabicyclo[2.2.2]oct-3-ylamino]-3-(1H-benzimidazol-2-yl)-6-chloroquinolin-2(1H)-one; 4-[(3R)-1-azabicyclo[2.2.2]oct-3-ylamino]-3-(1H-benzimidazol-2-yl)-6-chloroquinolin-2(1H)-one; 3-(1H-benzimidazol-2-yl)-4-[(3R)-3-(dimethylamino)pyrrolidin-1-yl]quinolin-2(1H)-one; 3-(1H-benzimidazol-2-yl)-6-chloro-4-[(3R)-3-(dimethylamino)pyrrolidin-1- yl]quinolin-2(1H)-one; 4-amino-3-[5-(4-ethylpiperazin-1-yl)-1H-benzimidazol-2-yl]-1-methylquinolin-2(1H)-one; 4-amino-3-(6-piperazin-1-yl-1H-benzimidazol-2-yl)quinolin-2(1H)-one; 4-amino-3-[6-(pyridin-4-ylmethyl)-1H-benzimidazol-2-yl]quinolin-2(1H)-one; 4-amino-3-{5-[(3R,5S)-3,5-dimethylpiperazin-1-yl]-1H-benzimidazol-2-yl}quinolin-2(1H)-one; 4-amino-3-[5-(4-methylpiperazin-1-yl)-1H-benzimidazol-2-yl]quinolin-2(1H)-one; 4-amino-3-(6-methyl-5-morpholin4-yl-1H-benzimidazol-2-yl)quinolin-2(1H)-one; 4-amino-3-{5-[(1-methylpiperidin-3-yl)oxy]-1H-benzimidazol-2-yl}quinolin-2(1H)-one; 4-amino-3-{5-[(2R,6S)-2,6-dimethylmorpholin-4-yl]-6-fluoro-1H-benzimidazol-2-yl}quinolin-2(1H)-one; 4-amino-3-{5-[(1-methylpyrrolidin-3-yl)oxy]-1H-benzimidazol-2-yl}quinolin-2(1H)-one; 4-amino-3-[5-(4-methyl-1,4-diazepan-1-yl)-1H-benzimidazol-2-yl]quinolin-2(1H)-one; 4-amino-3-{5-[(3R)-3-(dimethylamino)pyrrolidin-1-yl]-1H-benzimidazol-2-yl}quinolin-2(1H)-one; 4-amino-6-chloro-3-{5-[(3R)-3-(dimethylamino)pyrrolidin-1-yl]-1H-benzimidazol-2-yl}quinolin-2(1H)-one; ethyl {4-[2-(4-amino-2-oxo-1,2-dihydroquinolin-3-yl)-1H-benzimidazol-6-yl]piperazin-1-yl}acetate; 4-amino-3-{6-[methyl(1-methylpiperidin-4-yl)amino]-1H-benzimidazol-2-yl}quinolin-2(1H)-one; 3-[6-(4-acetylpiperazin-1-yl)-1H-benzimidazol-2-yl]-4-aminoquinolin-2(1H)-one; 4-amino-3-[6-(1,4'-bipiperidin-1'-yl)-1H-benzimidazol-2-yl]quinolin-2(1H)-one; 2-(4-amino-2-oxo-1,2-dihydroquinolin-3-yl)-1H-benzimidazole-6-carboxylic acid; 4-amino-5-(methyloxy)-3-[6-(4-methylpiperazin-1-yl)-1H-benzimidazol-2-yl]quinolin-2(1H)-one; 4-amino-3-{6-[4-(1-methylethyl)piperazin-1-yl]-1H-benzimidazol-2-yl}quinolin-2(1H)-one; {4-[2-(4-amino-2-oxo-1,2-dihydroquinolin-3-yl)-1H-benzimidazol-6-yl]piperazin-1-yl}acetic acid; 4-[(3S)-1-azabicyclo[2.2.2]oct-3-ylamino]-3-(1H-benzimidazol-2-yl)quinolin-2(1H)-one; 4-[(3R)-1-azabicyclo[2.2.2]oct-3-ylamino]-3-(1H-benzimidazol-2-yl)quinolin-2(1H)-one; 4-amino-3-[5-(4-ethylpiperazin-1-yl)-1H-benzimidazol-2-yl]quinolin-2(1H)-one; 4-amino-3-(5-{(2S,5S)-2-[(d imethylamino)methyl]-5-methylmorpholin-4-yl}-1H-benzimidazol-2-yl)quinolin-2(1H)-one; 4-amino-6-chloro-3-[5-(4-methylpiperazin-1-yl)-1H-benzimidazol-2-yl]quinolin-2(1H)-one; 4-amino-6-chloro-3-{5-[(3S)-3-(dimethylamino)pyrrolidin-1-yl]-1H-benzimidazol-2-yl}quinolin-2(1H)-one; 4-amino-5,6-dichloro-3-{5-[(3S)-3-(dimethylamino)pyrrolidin-1-yl]-1H-benzimidazol-2-yl}quinolin-2(1H)-one; 4-amino-5,6-dichloro-3-[5-(4-methylpiperazin-1-yl)-1H-benzimidazol-2-yl]quinolin-2(1H)-one; 4-amino-3-(1H-benzimidazol-2-yl)-6-[(pyridin-2-ylmethyl)oxy]quinolin-2(1H)-one; 4-amino-3-(1H-benzimidazol-2-yl)-6-[(2R,6S)-2,6-dimethylmorpholin-4-yl]quinolin-2(1H)-one; 4-amino-3-(1H-benzimidazol-2-yl)-6-morpholin-4-ylquinolin-2(1H)-one; 4-amino-3-(1H-benzimidazol-2-yl)-5-[(1-methylpiperidin-3-yl)oxy]quinolin-2(1H)-one; 4-amino-3-(1H-benzimidazol-2-yl)-5-[(pyridin-2-ylmethyl)oxy]quinolin-2(1H)-one; 4-amino-3-(5-morpholin4-yl-1H-benzimidazol-2-yl)-5-[(pyridin4-ylmethyl)oxy]quinolin-2(1H)-one; 4-amino-3-(1H-benzimidazol-2-yl)-5-(methyloxy)quinolin-2(1H)-one; 4-amino-3-(5-methyl-1H-benzimidazol-2-yl)-5-(methyloxy)quinolin-2(1H)-one; 4-amino-3-{5-[(2R,6S)-2,6-dimethylmorpholin-4-yl]-1H-benzimidazol-2-yl}-5-(methyloxy)quinolin-2(1H)-one; 4-amino-3-(1H-benzimidazol-2-yl)-5-morpholin-4-ylquinolin-2(1H)-one; 4-amino-3-(1H-benzimidazol-2-yl)-5-[(2R,6S)-2,6-dimethylmorpholin-4-yl]quinolin-2(1H)-one; 4-amino-3-(1H-benzimidazol-2-yl)-5-(4-methylpiperazin-1-yl)quinolin-2(1H)-one; 4-amino-5,6-dichloro-3-(5-morpholin-4-yl-1H-benzimidazol-2-yl)quinolin-2(1H)-one; 3-{5-[(2-morpholin-4-ylethyl)oxy]-1H-benzimidazol-2-yl}quinolin-2(1H)-one; 4-amino-3-{5-[(3-pyrrolidin-1-ylpropyl)oxy]-1H-benzimidazol-2-yl}quinolin-2(1H)-one; 4-amino-3-{5-[(3-morpholin-4-ylpropyl)oxy]-1H-benzimidazol-2-yl}quinolin-2(1H)-one; 4-amino-6-fluoro-3-(5-morpholin-4-yl-1H-benzimidazol-2-yl)quinolin-2(1H)-one; 4-amino-3-{5-[3-(dimethylamino)pyrrolidin-1-yl]-1H-benzimidazol-2-yl}-6-fluoroquinolin-2(1H)-one; 4-amino-3-(1H-benzimidazol-2-yl)-6-fluoroquinolin-2(1H)-one; 4-amino-3-(6-fluoro-5-morpholin-4-yl-1H-benzimidazol-2-yl)quinolin-2(1H)-one; 4-amino-3-{5-[(tetrahydrofuran-2-ylmethyl)oxy]-1H-benzimidazol-2-yl}quinolin-2(1H)-one; 4-amino-6-fluoro-3-(6-fluoro-5-morpholin-4-yl-1H-benzimidazol-2-yl)quinolin-2(1H)-one; 4-amino-3-[6-fluoro-5-(4-methylpiperazin-1-yl)-1H-benzimidazol-2-yl]quinolin-2(1H)-one; 4-amino-3-(5-{[2-(methyloxy)ethyl]oxy}-1H-benzimidazol-2-yl)quinolin-2(1H)-one; 4-amino-3-[4,6-difluoro-5-(4-methylpiperazin-1-yl)-1H-benzimidazol-2-yl]quinolin-2(1H)-one; 4-amino-3-{5-[3-(d imethylamino)pyrrolidin-1-yl]-1H-benzimidazol-2-yl}-5-fluoroquinolin-2(1H)-one; 4-amino-5-fluoro-3-[5-(4-methylpiperazin-1-yl)-1H-benzimidazol-2-yl]quinolin-2(1H)-one; 4-amino-5-chloro-3-[5-(4-methylpiperazin-1-yl)-1H-benzimidazol-2-yl]quinolin-2(1H)-one; 4-amino-3-{5-[3-(dimethylamino)pyrrolidin-1-yl]-6-fluoro-1H-benzimidazol-2-yl}quinolin-2(1H)-one; 4-amino-5-chloro-3-{5-[3-(dimethylamino)pyrrolidin-1-yl]-1H-benzimidazol-2-yl}quinolin-2(1H)-one; 4-amino-6-chloro-3-{5-[3-(dimethylamino)pyrrolidin-1-yl]-6-fluoro-1H-benzimidazol-2-yl}quinolin-2(1H)-one; 4-amino-5-[(2R,6S)-2,6-dimethylmorpholin-4-yl]-3-(3H-imidazo[4,5-b]pyridin-2-yl)quinolin-2(1H)-one; 4-amino-3-(6-thiomorpholin-4-yl-1H-benzimidazol-2-yl)quinolin-2(1H)-one; 4-amino-3-[5-(4-cyclohexylpiperazin-1-yl)-1H-benzimidazol-2-yl]quinolin-2(1H)-one; 4-amino-3-{6-[3-(diethylamino)pyrrolidin-1-yl]-1H-benzimidazol-2-yl}quinolin-2(1H)-one; 4-amino-3-[6-(4-pyridin-2-ylpiperazin-1-yl)-1H-benzimidazol-2-yl]quinolin-2(1H)-one; 4-amino-3-[5-(4-methylpiperazin-1-yl)-3H-imidazo[4,5-b]pyridin-2-yl]quinolin-2(1H)-one; 4-amino-6-chloro-3-[5-(4-methylpiperazin-1-yl)-1H-imidazo[4,5-b]pyridin-2-yl]quinolin-2(1H)-one; 2-(4-amino-2-oxo-1,2-dihydroquinolin-3-yl)-N-methyl-N-(1-methylpiperidin-4-yl)-1H-benzimidazole-5-carboxamide; 4-amino-3-(5-{[4-(1-methylethyl)piperazin-1-yl]carbonyl}-1H-benzimidazol-2-yl)quinolin-2(1H)-one; 4-amino-3-[5-(4-methylpiperazin-1-yl)-1H-benzimidazol-2-yl]-6-nitroquinolin-2(1H)-one; 4-amino-3-[5-(1,4'-bipiperidin-1'-ylcarbonyl)-1H-benzimidazol-2-yl]quinolin-2(1H)-one; 4-amino-3-{5-[(4-methylpiperazin-1-yl)carbonyl]-1H-benzimidazol-2-yl}quinolin-2(1H)-one; 4-amino-3-[5-(1-oxidothiomorpholin-4-yl)-1H-benzimidazol-2-yl]quinolin-2(1H)-one; 3-{5-[(4-acetylpiperazin-1-yl)carbonyl]-1H-benzimidazol-2-yl}-4-aminoquinolin-2(1H)-one; 4-amino-3-(5-{[(3R)-3-(dimethylamino)pyrrolidin-1-yl]carbonyl}-1H-benzimidazol-2-yl)quinolin-2(1H)-one; 4-amino-3-(5-{[(3S)-3-(dimethylamino)pyrrolidin-1-yl]carbonyl}1H-benzimidazol-2-yl)quinolin-2(1H)-one; 4-amino-3-(5-{[4-(dimethylamino)piperidin-1-yl]carbonyl}-1H-benzimidazol-2-yl)quinolin-2(1H)-one; methyl 2-(4-amino-5- fluoro-2-oxo-1,2-dihydroquinolin-3-yl)-1H-benzimidazole-6-carboxylate; 4-amino-3-[5-(1,3'-bipyrrolidin-1'-yl)-1H-benzimidazol-2-yl]quinolin-2(1H)-one; 4-amino-3-[5-(pyridin-3-yloxy)-1H-benzimidazol-2-yl]quinolin-2(1H)-one; 4-amino-5,6-bis(methyloxy)-3-[5-(4-methylpiperazin-1-yl)-1H-benzimidazol-2-yl]quinolin-2(1H)-one; 2-(4-amino-2-oxo-1,2-dihydroquinolin-3-yl)-N-[2-(dimethylamino)ethyl]-N-methyl-1H-benzimidazole-5-carboxamide; 2-(4-amino-2-oxo-1,2-dihydroquinolin-3-yl)-N-methyl-N-(1-methylpyrrolidin-3-yl)-1H-benzimidazole-5-carboxamide; 4-amino-3-{5-[(5-methyl-2,5-diazabicyclo[2.2.1]hept-2-yl)carbonyl]-1H-benzimidazol-2-yl}quinolin-2(1H)-one; 4-amino-3-{5-[(4-cyclohexylpiperazin-1-yl)carbonyl]-1H-benzimidazol-2-yl}quinolin-2(1H)-one; 4-amino-3-{5-[(2-piperidin-1-ylethyl)amino]-1H-benzimidazol-2-yl}quinolin-2(1H)-one; ethyl 4-{[2-(4-amino-2-oxo-1,2-dihydroquinolin-3-yl)-1H-benzimidazol-5-yl]amino}piperidine-1-carboxylate; 4-amino-3-[5-({(5R)-5-[(methyloxy)methyl]pyrrolidin-3-yl}amino)-1H-benzimidazol-2-yl]quinolin-2(1H)-one; 4-amino-3-{5-[(pyridin-2-ylmethyl)amino]-1H-benzimidazol-2-yl}quinolin-2(1H)-one; 4-amino-3-[5-(piperidin-3-ylamino)-1H-benzimidazol-2-yl]quinolin-2(1H)-one; 4-amino-5-fluoro-3-{5-[(pyridin-2-ylmethyl)amino]-1H-benzimidazol-2-yl}quinolin-2(1H)-one; ethyl 4-{[2-(4-amino-5-fluoro-2-oxo-1,2-dihydroquinolin-3-yl)-1H-benzimidazol-5-yl]amino}piperidine-1-carboxylate; 4-amino-5-fluoro-3-[5-(piperidin-3-ylamino)-1H-benzimidazol-2-yl]quinolin-2(1H)-one; 4-amino-3-(1H-benzimidazol-2-yl)-6-bromoquinolin-2(1H)-one; 4-amino-3-(1H-benzimidazol-2-yl)-7-bromoquinolin-2(1H)-one; 4-amino-3-(5-bromo-1H-benzimidazol-2-yl)quinolin-2(1H)-one; N,N-dimethyl-2-(2-oxo-1,2-dihydroquinolin-3-yl)-1H-benzimidazole-5-carboxamide; 4-amino-3-(5-thien-2-yl-1H-benzimidazol-2-yl)quinolin-2(1H)-one; 2-(4-amino-2-oxo-1,2-dihydroquinolin-3-yl)-N,N-dimethyl-1H-benzimidazole-5-sulfonamide; 4-amino-6-iodo-3-[5-(4-methylpiperazin-1-yl)-1H-benzimidazol-2-yl]quinolin-2(1H)-one; 4-amino-3-(5-{2-[(dimethylamino)methyl]morpholin-4-yl}-1H-benzimidazol-2-yl)quinolin-2(1H)-one; 4-[(3R)-1-azabicyclo[2.2.2]oct-3-ylamino]-3-(1H-benzimidazol-2-yl)-7-chloro-6-iodoquinolin-2(1H)-one; 4-[(3R)-1-azabicyclo[2.2.2]oct-3-ylamino]-3-(1H-benzimidazol-2-yl)-6-nitroquinolin-2(1H)-one; 4-[(3R)-1-azabicyclo[2.2.2]oct-3-ylamino]-3-(1H-benzimidazol-2-yl)-6-methylquinolin-2(1H)-one; 4-[(3R)-1-azabicyclo[2.2.2]oct-3-ylamino]-3-(1H-benzimidazol-2-yl)-6,7-difluoroquinolin-2(1H)-one; 4-[(3S)-1-azabicyclo[2.2.2]oct-3-ylamino]-3-(1H-benzimidazol-2-yl)-7-chloroquinolin-2(1H)-one; 4-[(3R)-1-azabicyclo[2.2.2]oct-3-ylamino]-3-(1H-benzimidazol-2-yl)-6-bromoquinolin-2(1H)-one; 4-[(3R)-1-azabicyclo[2.2.2]oct-3-ylamino]-3-(1H-benzimidazol-2-yl)-2-oxo-1,2-dihydroquinoline-6-carbonitrile; 4-[(3R)-1-azabicyclo[2.2.2]oct-3-ylamino]-3-(1H-benzimidazol-2-yl)-6-fluoroquinolin-2(1H)-one; 4-[(3S)-1-azabicyclo[2.2.2]oct-3-ylamino]-3-(1H-benzimidazol-2-yl)-6,7-bis(methyloxy)quinolin-2(1H)-one; 4-[(3R)-1-azabicyclo[2.2.2]oct-3-ylamino]-3-(1H-benzimidazol-2-yl)-6,7-dichloroquinolin-2(1H)-one; 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxamide; 4-[(3S)-1-azabicyclo[2.2.2]oct-3-ylamino]-3-(1H-benzimidazol-2-yl)-6-fluoro-7-[(3-hydroxypropyl)amino]quinolin-2(1H)-one; 4-[(3S)-1-azabicyclo[2.2.2]oct-3-ylamino]-3-(1H-benzimidazol-2-yl)-7-(dimethylamino)-6-fluoroquinolin-2(1H)-one; 4-[(3R)-1-azabicyclo[2.2.2]oct-3-ylamino]-3-(1H-benzimidazol-2-yl)-5-fluoroquinolin-2(1H)-one; 4-[(3R)-1-azabicyclo[2.2.2]oct-3-ylamino]-3-(1H-benzimidazol-2-yl)-6-(4-nitrophenyl)quinolin-2(1H)-one; 4-[(3S)-1-azabicyclo[2.2.2]oct-3-ylamino]-3-(1H-benzimidazol-2-yl)-7-{[2-(dimethylamino)ethyl]amino}-6-fluoroquinolin-2(1H)-one; 4-[(3S)-1-azabicyclo[2.2.2]oct-3-ylamino]-3-(1H-benzimidazol-2-yl)-6-fluoro-7-(1H-imidazol-1-yl)quinolin-2(1H)-one; 4-[(3R)-1-azabicyclo[2.2.2]oct-3-ylamino]-3-(1H-benzimidazol-2-yl)-6-[4-(methyloxy)phenyl]quinolin-2(1H)-one; 4-[(3S)-1-azabicyclo[2.2.2]oct-3-ylamino]-3-(1H-benzimidazol-2-yl)-6-fluoro-7-morpholin-4-ylquinolin-2(1H)-one; 4-[(3R)-1-azabicyclo[2.2.2]oct-3-ylamino]-6,7-difluoro-3-(3H-imidazo[4,5-b]pyridin-2-yl)quinolin-2(1H)-one; 4-[(3R)-1-azabicyclo[2.2.2]oct-3-ylamino]-3-(1H-benzimidazol-2-yl)-6-(3-nitrophenyl)quinolin-2(1H)-one; 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxamide; 4-[(3S)-1-azabicyclo[2.2.2]oct-3-ylamino]-3-(1H-benzimidazol-2-yl)-5-methylquinolin-2(1H)-one; 6-(3-acetylphenyl)-4-[(3R)-1-azabicyclo[2.2.2]oct-3-ylamino]-3-(3H-imidazo[4,5-b]pyridin-2-yl)quinolin-2(1H)-one; 4-[(3S)-1-azabicyclo[2.2.2]oct-3-ylamino]-3-(1H-benzimidazol-2-yl)-5-chloroquinolin-2(1H)-one; 4-[(3R)-1-azabicyclo[2.2.2]oct-3-ylamino]-6-fluoro-3-(3H-imidazo[4,5-b]pyridin-2-yl)-7-morpholin-4-ylquinolin-2(1H)-one; 4-[(3S)-1-azabicyclo[2.2.2]oct-3-ylamino]-3-(1H-benzimidazol-2-yl)-7-(cyclopropylamino)-6-fluoroquinolin-2(1H)-one; N-{3-[4-[(3R)-1-azabicyclo[2.2.2]oct-3-ylamino]-3-(3H-imidazo[4,5-b]pyridin-2-yl)-2-oxo-1,2-dihydroquinolin-6-yl]phenyl}acetamide; 4-[(3S)-1-azabicyclo[2.2.2]oct-3-ylamino]-3-(1H-benzimidazol-2-yl)-6-fluoro-7-(4-methylpiperazin-1-yl)quinolin-2(1H)-one; 4-[(3R)-1-azabicyclo[2.2.2]oct-3-ylamino]-6-fluoro-7-(1H-imidazol-1-yl)-3-(3H-imidazo[4,5-b]pyridin-2-yl)quinolin-2(1H)-one; 4-[(3S)-1-azabicyclo[2.2.2]oct-3-ylamino]-3-(1H-benzimidazol-2-yl)-6-fluoro-7-[(2-pyridin-2-ylethyl)amino]quinolin-2(1H)-one; 4-[(3S)-1-azabicyclo[2.2.2]oct-3-ylamino]-3-(1H-benzimidazol-2-yl)-6-fluoro-7-piperidin-1-ylquinolin-2(1H)-one; 6-chloro-3-(3H-imidazo[4,5-b]pyridin-2-yl)quinolin-2(1H)-one; ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-4-carboxylate; 4-[(3R)-1-azabicyclo[2.2.2]oct-3-ylamino]-3-(1H-benzimidazol-2-yl)-6-(1-benzothien-2-yl)quinolin-2(1H)-one; 4-[(3S)-1-azabicyclo[2.2.2]oct-3-ylamino]-3-(1H-benzimidazol-2-yl)-6-fluoro-7-pyrrolidin-1-ylquinolin-2(1H)-one; 4-[(3R)-1-azabicyclo[2.2.2]oct-3-ylamino]-3-(3H-imidazo[4,5-b]pyridin-2-yl)-6-[2-(trifluoromethyl)phenyl]quinolin-2(1H)-one; 4-[(3R)-1-azabicyclo[2.2.2]oct-3-ylamino]-3-(3H-imidazo[4,5-b]pyridin-2-yl)-[2-(methyloxy)phenyl]quinolin-2(1H)-one; ethyl 1-[4-[(3S)-1-azabicyclo[2.2.2]oct-3-ylamino]-3-(1H-benzimidazol-2-yl)-6-fluoro-2-oxo-1,2-dihydroquinolin-7-yl]piperidine-3-carboxylate; 4-[(3R)-1-azabicyclo[2.2.2]oct-3-ylamino]-3-(1H-benzimidazol-2-yl)-6-(4-ethylphenyl)quinolin-2(1H)-one; 4-[(3S)-1-azabicyclo[2.2.2]oct-3-ylamino]-3-(1H-benzimidazol-2-yl)-6-fluoro-7-[(2-methylpropyl)amino]quinolin-2(1H)-one; 4-[(3R)-1-azabicyclo[2.2.2]oct-3-ylamino]-3-(1H-benzimidazol-2-yl)-5-methylquinolin-2(1H)-one; 4-[(3R)-1-azabicyclo[2.2.2]oct-3-ylamino]-6-(2,4-dichlorophenyl)-3-(3H-imidazo[4,5-b]pyridin-2-yl)quinolin-2(1H)-one; 4-[(3R)-

1-azabicyclo[2.2.2]oct-3-ylamino]-3-(1H-benzimidazol-2-yl)-6-[3-(trifluoromethyl)phenyl]quinolin-2(1H)-one; 3-(1H-benzimidazol-2-yl)-4-(dimethylamino)quinolin-2 (1H)-one; 4-hydroxy-3-(1H-imidazo[4,5-f]quinolin-2-yl) quinolin-2(1H)-one; 4-hydroxy-3-(1H-imidazo[4,5-b]pyridin-2-yl)quinolin-2(1H)-one; 4-[4-[(3R)-1-azabicyclo [2.2.2]oct-3-ylamino]-3-(1H-benzimidazol-2-yl)-5-fluoro-2-oxo-1,2-dihydroquinolin-6-yl]benzoic acid; 4-[4-[(3R)-1-azabicyclo[2.2.2]oct-3-ylamino]-3-(1H-benzimidazol-2-yl)-5-fluoro-2-oxo-1,2-dihydroquinolin-6-yl]benzamide; N-{3-[4-[(3R)-1-azabicyclo[2.2.2]oct-3-ylamino]-3-(1H-benzimidazol-2-yl)-5-fluoro-2-oxo-1,2-dihydroquinolin-6-yl]phenyl}acetamide; 3-[4-[(3R)-1-azabicyclo[2.2.2]oct-3-ylamino]-3-(1H-benzimidazol-2-yl)-5-fluoro-2-oxo-1,2-dihydroquinolin-6-yl]benzoic acid; 4-[4-[(3R)-1-azabicyclo[2.2.2]oct-3-ylamino]-3-(1H-benzimidazol-2-yl)-7-fluoro-2-oxo-1,2-dihydroquinolin-6-yl]benzoic acid; N-{3-[4-[(3R)-1-azabicyclo[2.2.2]oct-3-ylamino]-3-(1H-benzimidazol-2-yl)-7-fluoro-2-oxo-1,2-dihydroquinolin-6-yl]phenyl}acetamide; 4-[(3R)-1-azabicyclo[2.2.2]oct-3-ylamino]-3-(1H-benzimidazol-2-yl)-7-chloro-6-(2-methylphenyl)quinolin-2(1H)-one; 4-[(3R)-1-azabicyclo[2.2.2]oct-3-ylamino]-3-(1H-benzimidazol-2-yl)-2-oxo-1,2-dihydroquinoline-7-carbonitrile; 4-[(3R)-1-azabicyclo[2.2.2]oct-3-ylamino]-3-(1H-benzimidazol-2-yl)-7-(methyloxy)quinolin-2(1H)-one; 4-[4-[(3R)-1-azabicyclo[2.2.2]oct-3-ylamino]-3-(1H-benzimidazol-2-yl)-2-oxo-1,2-dihydroquinolin-7-yl]benzamide; 4-[(3R)-1-azabicyclo[2.2.2]oct-3-ylamino]-3-(1H-benzimidazol-2-yl)-6-fluoro-7-(methyloxy)quinolin-2(1H)-one; 4-[(3R)-1-azabicyclo[2.2.2]oct-3-ylamino]-3-(1H-benzimidazol-2-yl)-6-chloro-7-(dimethylamino)quinolin-2 (1H)-one; 4-[(3R)-1-azabicyclo[2.2.2]oct-3-ylamino]-3-(1H-benzimidazol-2-yl)-7-(dimethylamino)-6-iodoquinolin-2(1H)-one; 3-[4-[(3R)-1-azabicyclo[2.2.2] oct-3-ylamino]-3-(1H-benzimidazol-2-yl)-7-(1H-imidazol-1-yl)-2-oxo-1,2-dihydroquinolin-6-yl]benzoic acid; 4-[4-[(3R)-1-azabicyclo[2.2.2]oct-3-ylamino]-3-(1H-benzimidazol-2-yl)-2-oxo-7-piperidin-1-yl-1,2-dihydroquinolin-6-yl]benzoic acid; 4-[(3R)-1-azabicyclo[2.2.2]oct-3-ylamino]-3-(1H-benzimidazol-2-yl)-7-(methyloxy)-6-[4-(methylsulfonyl)phenyl]quinolin-2 (1H)-one; 4-[(3R)-1-azabicyclo[2.2.2]oct-3-ylamino]-3-(1H-benzimidazol-2-yl)-8-methylquinolin-2(1H)-one; 4-[(3S)-1-azabicyclo[2.2.2]oct-3-ylamino]-3-(1H-benzimidazol-2-yl)-6,7-difluoroquinolin-2(1H)-one; 3-(1H-benzimidazol-2-yl)-6-methyl4-(piperidin-3-ylamino) quinolin-2(1H)-one; 4-[(3S)-1-azabicyclo[2.2.2]oct-3-ylamino]-3-(1H-benzimidazol-2-yl)-6-[2-(methyloxy) phenyl]quinolin-2(1H)-one; 4-[(3S)-1-azabicyclo[2.2.2] oct-3-ylamino]-3-(1H-benzimidazol-2-yl)-6-[3-(methyloxy)phenyl]quinolin-2(1H)-one; 3-(1H-benzimidazol-2-yl)-6,7-difluoro-4-(piperidin-4-ylamino) quinolin-2(1H)-one; 3-(1H-benzimidazol-2-yl)-6,7-difluoro-4-(pyrrolidin-3-ylamino)quinolin-2(1H)-one; 3-(1H-benzimidazol-2-yl)-6-chloro-4-[(3-morpholin-4-ylpropyl)amino]quinolin-2(1H)-one; 6-chloro-3-(5-morpholin-4-yl-1H-benzimidazol-2-yl)-4-(piperidin-4-ylamino)quinolin-2(1H)-one; 6-chloro-3-(5-morpholin-4-yl-1H-benzimidazol-2-yl)-4-[(piperidin-2-ylmethyl) amino]quinolin-2(1H)-one; 4-[(3S)-1-azabicyclo[2.2.2] oct-3-ylamino]-6-chloro-3-(5-morpholin-4-yl-1H-benzimidazol-2-yl)quinolin-2(1H)-one; 6-chloro-3-(5-morpholin-4-yl-1H-benzimidazol-2-yl)-4-(piperidin-3-ylamino)quinolin-2(1H)-one; 6-chloro4-{[2-(dimethylamino)ethyl]amino}-3-(5-morpholin-4-yl-1H-benzimidazol-2-yl)quinolin-2(1H)-one; 4-[(3R)-1-azabicyclo[2.2.2]oct-3-ylamino]-6-chloro-3-(5-morpholin4-yl-1H-benzimidazol-2-yl)quinolin-2(1H)-one; 6-chloro-3-(5-morpholin-4-yl-1H-benzimidazol-2-yl)-4-[(piperidin-3-ylmethyl)amino]quinolin-2(1H)-one; 6-chloro-3-(5-morpholin-4-yl-1H-benzimidazol-2-yl)-4-[(piperidin-4-ylmethyl)amino]quinolin-2(1H)-one; 4-{[(1R,2R)-2-aminocyclohexyl]amino)6-chloro-3-(5-morpholin-4-yl-1H-benzimidazol-2-yl)quinolin-2(1H)-one; 4-[(4-aminocyclohexyl]amino}-6-chloro-3-(5-morpholin-4-yl-1H-benzimidazol-2-yl)quinolin-2(1H)-one; 4-{[(2S)-2-amino-3-methylbutyl]amino}6-chloro-3-(5-morpholin-4-yl-1H-benzimidazol-2-yl)quinolin-2(1H)-one; 4-({[4-(aminomethyl)phenyl]methyl}amino)-6-chloro-3-(5-morpholin-4-yl-1H-benzimidazol-2-yl) quinolin-2(1H)-one; 6-chloro-3-(5-morpholin-4-yl-1H-benzimidazol-2-yl)-4-[(pyrrolidin-2-ylmethyl)amino] quinolin-2(1H)-one; 4-{[(1R)-1-(aminomethyl)propyl] amino}-6-chloro-3-(5-morpholin-4-yl-1H-benzimidazol-2-yl)quinolin-2(1H)-one; 4-{[(1S)-2-amino-1-(phenylmethyl)ethyl]amino}-6-chloro-3-(5-morpholin-4-yl-1H-benzimidazol-2-yl)quinolin-2(1H)-one; 6-chloro-4-{[3-(4-methylpiperazin-1-yl)propyl]amino}-3-(5-morpholin-4-yl-1H-benzimidazol-2-yl)quinolin-2(1H)-one; 6-chloro-3-(5-morpholin-4-yl-1H-benzimidazol-2-yl)4-{[1-(phenylmethyl)piperidin-4-yl]amino}quinolin-2 (1H)-one; 6-chloro-3-(5-morpholin-4-yl-1H-benzimidazol-2-yl)-4-[(3-morpholin-4-ylpropyl)amino] quinolin-2(1H)-one; 6-chloro-3-(5-morpholin-4-yl-1H-benzimidazol-2-yl)-4-[(2-piperidin-1-ylethyl)amino] quinolin-2(1H)-one; 6-chloro-3-(5-morpholin4-yl-1H-benzimidazol-2-yl)4-[(pyridin-3-ylmethyl)amino] quinolin-2(1H)-one; 6-chloro4-{[3-(1H-imidazol-1-yl) propyl]amino}-3-(5-morpholin-4-yl-1H-benzimidazol-2-yl)quinolin-2(1H)-one; 6-chloro-3-(5-morpholin-4-yl-1H-benzimidazol-2-yl)-4-[(pyridin-4-ylmethyl)amino] quinolin-2(1H)-one; 6-chloro4-{[2-(methylamino)ethyl] amino}-3-(5-morpholin-4-yl-1H-benzimidazol-2-yl) quinolin-2(1H)-one; 6-chloro-4-{[(2-methyl-1-piperidin-4-yl-1H-benzimidazol-5-yl)methyl]amino}-3-(5-morpholin-4-yl-1H-benzimidazol-2-yl)quinolin-2(1H)-one; 6-chloro-3-(5-morpholin-4-yl-1H-benzimidazol-2-yl)-4-[(2-pyrrolidin-1-ylethyl)amino]quinolin-2(1H)-one; 6-chloro-3-(5-morpholin-4-yl-1H-benzimidazol-2-yl)-4-(pyrrolidin-3-ylamino)quinolin-2(1H)-one; 4-{[(1R,2R)-2-aminocyclohexyl]amino}-6-chloro-3-[5-(4-methylpiperazin-1-yl)-1H-benzimidazol-2-yl]quinolin-2(1H)-one; 4-[(4-aminocyclohexyl)amino]-6-chloro-3-[5-(4-methylpiperazin-1-yl)-1H-benzimidazol-2-yl]quinolin-2(1H)-one; 4-({[4-(aminomethyl)phenyl]methyl}amino)-6-chloro-3-[5-(4-methylpiperazin-1-yl)-1H-benzimidazol-2-yl]quinolin-2(1H)-one; 6-chloro-4-{[2-(methylamino)ethyl]amino}-3-[5-(4-methylpiperazin-1-yl)-1H-benzimidazol-2-yl]quinolin-2(1H)-one; 6-chloro-3-[5-(4-methylpiperazin-1-yl)-1H-benzimidazol-2-yl]-4-{[3-(4-methylpiperazin-1-yl)propyl] amino}quinolin-2(1H)-one; 6-chloro-3-[5-(4-methylpiperazin-1-yl)-1H-benzimidazol-2-yl]-4-{[1-(phenylmethyl)piperidin-4-yl]amino}quinolin-2(1H)-one; 6-chloro-3-[5-(4-methylpiperazin-1-yl)-1H-benzimidazol-2-yl]-4-[(2-pyrrolidin-1-ylethyl)amino] quinolin-2(1H)-one; 6-chloro-3-[5-(4-methylpiperazin-1-yl)-1H-benzimidazol-2-yl]-4-(pyrrolidin-3-ylamino) quinolin-2(1H)-one; 6-chloro-3-[5-(4-methylpiperazin-1-yl)-1H-benzimidazol-2-yl]-4-(piperidin-4-ylamino) quinolin-2(1H)-one; 6-chloro-3-(5-morpholin-4-yl-1H-benzimidazol-2-yl)-4-[(2-piperidin-2-ylethyl)amino]

quinolin-2(1H)-one; 4-[(3S)-1-azabicyclo[2.2.2]oct-3-ylamino]-7-chloro-3-(5-morpholin-4-yl-1H-benzimidazol-2-yl)quinolin-2(1H)-one; 7-chloro-3-(5-morpholin4-yl-1H-benzimidazol-2-yl)-4-(piperidin-3-ylamino)quinolin-2(1H)-one; 6-chloro-3-[5-(4-methylpiperazin-1-yl)-1H-benzimidazol-2-yl]-4-[(piperidin-2-ylmethyl)amino]quinolin-2(1H)-one; 6-chloro-3-[5-(4-methylpiperazin-1-yl)-1H-benzimidazol-2-yl]-4-{[(2S)-pyrrolidin-2-ylmethyl]amino}quinolin-2(1H)-one; 6-chloro-3-[5-(4-methylpiperazin-1-yl)-1H-benzimidazol-2-yl]-4-{[(2R)-pyrrolidin-2-ylmethyl]amino}quinolin-2(1H)-one; 6-chloro-4-({[(2S)-1-ethylpyrrolidin-2-yl]methyl}amino)-3-[5-(4-methylpiperazin-1-yl)-1H-benzimidazol-2-yl]quinolin-2(1H)-one; 6-chloro-4-({[(2R)-1-ethylpyrrolidin-2-yl]methyl}amino)-3-[5-(4-methylpiperazin-1-yl)-1H-benzimidazol-2-yl]quinolin-2(1H)-one; 4-[(3S)-1-azabicyclo[2.2.2]oct-3-ylamino]-3-(1H-benzimidazol-2-yl)-6-[4-(methyloxy)phenyl]quinolin-2(1H)-one; and 6-(3-aminophenyl)-4-[(3S)-1-azabicyclo[2.2.2]oct-3-ylamino]-3-(1H-benzimidazol-2-yl)quinolin-2(1H)-one.

Each of the above compounds displayed an $IC_{50}$ value of less than 10 μM with respect to VEGFR1, VEGFR2, and bFGF.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

It is understood that the invention is not limited to the embodiments set forth herein for illustration, but embraces all such forms thereof as come within the scope of the following claims.

What is claimed is:

1. A method of treating a cancer patient in need of an inhibitor of a receptor tyrosine kinase, comprising: administering an effective amount of a compound, a tautomer of the compound, a pharmaceutically acceptable salt of the compound, a pharmaceutically acceptable salt of the tautomer, or a pharmaceutical formulation comprising the compound, the tautomer of the compound, the pharmaceutically acceptable salt of the compound, and/or the pharmaceutically acceptable salt of the tautomer to a patient in need thereof, wherein the receptor tyrosine kinase is vascular endothelial growth factor receptor tyrosine kinase or basic fibroblast growth factor receptor and the receptor tyrosine kinase is inhibited in the patient, after administration and further wherein the compound is 4-amino-5-fluoro-3[5-4-methylpiperazin-1-yl)-1H-benzimidazol-2-yl]quinolin-2(1H)-one.

2. A method comprising: administering to a patient having cancer an effective amount of a compound having structure I, a tautomer of the compound, a pharmaceutically acceptable salt of the compound, a pharmaceutically acceptable salt of the tautomer, or a pharmaceutical formulation comprising the compound, the tautomer of the compound, the pharmaceutically acceptable salt of the compound, and/or the pharmaceutically acceptable salt of the tautomer, wherein the cancer comprises cells expressing a receptor tyrosine kinase selected from the group consisting of vascular endothelial growth factor receptor tyrosine kinase and basic fibroblast growth factor receptor, and further wherein the compound having structure I has the following formula

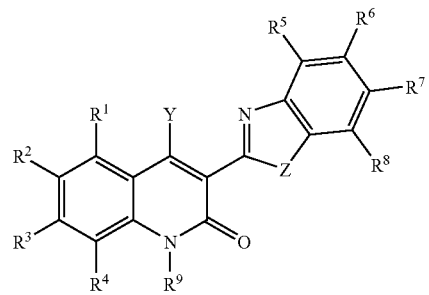

wherein,

Y is an —$NR^{12}R^{13}$ group;

Z is an $NR^{14}$ group;

$R^1$, $R^2$, $R^3$, and $R^4$ may be the same or different and are independently selected from the group consisting of H, Cl, Br, F, I, —CN, —$NO_2$, —OH, —$OR^{15}$ groups, —$NR^{16}R^{17}$ groups, substituted and unsubstituied amidinyl groups, substituted and unsubstituted guanidinyl groups, substituted and unsubstituted primary, secondary, and tertiary alkyl groups, substituted and unsubstituted aryl groups, substituted and unsubstituted aikenyl groups, substituted and unsubstituted alkyny groups, substituted and unsubstituted heterocyclyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, and —$C(=O)R^{18}$ groups;

$R^5$, $R^6$, $R^7$, and $R^8$ may be the same or different and are independently selected from the group consisting of H, Cl, Br, F, I, —$NO_2$, —OH, —$OR^{19}$ groups, —$NR^{20}R^{21}$ groups, —SH, —$SR^{22}$ groups, —$S(=O)R^{23}$ groups, —$S(=O)_2R^{24}$ groups, —CN, substituted and unsubstituted amidinyl groups, substituted and unsubstituted guanidinyl groups, substituted and unsubstituted primary, secondary, and tertiary alkyl groups, substituted and unsubstituted aryl groups, substituted and unsubstituted alkenyl groups, substituted and unsubstituted alkynyl groups, substituted and unsubstituted heterocyclyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylalkyl groups, —$C(=O)R^{25}$ groups, substituted and unsubstituted aminoalkyl groups, substituted and unsubstituted heterocyclylaminoalkyl groups, substituted and unsubstituted hydroxyalkyl groups, substituted and unsubstituted alkoxyalkyl groups, substituted and unsubstituted aryloxyalkyl groups, and substituted and unsubstituted heterocyclyloxyalkyl groups;

$R^9$ is H;

$R^{12}$ is selected from the group consisting of H, substituted and unsubstituted alkyl groups, substituted and unsubstituted aryl groups, and substituted and unsubstituted heterocyclyl groups;

$R^{13}$ is selected from the group consisting of H, substituted and unsubstituted alkyl groups, substituted and unsubstituted aryl groups, substituted and unsubstituted heterocyclyl groups, —OH, alkoxy groups, aryloxy groups, —NH$_2$, substituted and unsubstituted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted alkylamino groups, substituted and unsubstituted arylamino groups, substituted and unsubstituted dialkylamino groups, substituted and unsubstituted diarylamino groups, substituted and unsubstituted (alkyl)(aryl)amino groups, —C(=O)H, —C(=O)-alkyl groups, —C(=O)-aryl groups, —C(=O)O-alkyl groups, —C(=O)O-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstiiuted heterocyelylaminoalkyl groups, substituted and unsubstituted hydroxyalkyl groups, substituted and unsubstituted alkoxyalkyl groups, substituted and unsubstituted, aryloxyalkyl groups, and substituted and unsubstituted heterocyclyloxyalkyl groups;

$R^{14}$ is H;

$R^{15}$ and $R^{19}$ may be the same or different and are independently selected from the group consisting of substituted and unsubstituted alkyl groups, substituied and unsubstituted aryl groups, substituted and unsubstituted heterocyclyl groups, substituted and unsubstituted heterocyclylalkyl groups, —C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, substituted and unsubstituted heterocyclylaminoalkyl, substituted and unsubstituted diheterocyclylaminoalkyl, substituted and unsubstituted (heterocyclyl)(alkyl)aminoalkyl, substituted and unsubstituted (heterocyclyl)(alkyl)aminoalkyl, substituted and unsubstituted alkoxyalkyl groups, substituted and unsubstituted hydroxyalkyl groups, substituted and unsubstituted aryloxyalkyl groups, and substituted and unsubstituted heterocyclyloxyalkyl groups;

$R^{16}$ and $R^{20}$ may be the same or different and arc independently selected from the group consisting of H, substituted and unsubstituted alkyl groups, substituted and unsubstituted aryl groups, and substituted and unsubstituted heterocyclyl groups;

$R^{17}$ and $R^{21}$ may be the same or different and are independently selected from the group consisting of H, substituted and unsubstituted alkyl groups, substituted and unsubstituted aryl groups, substituted and unsubstituted heterocyclyl groups, C(=O)H, —C(=O)-alkyl groups, —C(=O)-aryl groups, —C(=O)NH$_2$, —C(=O)NH(alkyl) groups, —C(=O)NH(aryl) groups, —C(=O)N(alkyl)$_2$ groups, —C(=O)N(aryl)$_2$ groups, —C(=O)N(alkyl)(aryl) groups, —C(=O)O-alkyl groups, —C(=O)O-aryl groups, substituted and unsubstitiuted heterocyclylalkyl groups, substituted and unsubstituted aminoalkyl groups, substituted and unsubstituted alkylaminoalkyl groups, substituted and unsubstituted dialkylaminoalkyl groups, substituted and unsubstituted arylaminoalkyl groups, substituted and unsubstituted diarylaminoalkyl groups, substituted and unsubstituted (alkyl)(aryl)aminoalkyl groups, —C(=O)-heterocyclyl groups, —C(=O)—O-heterocyclyl groups, —C(=O)NH(heterocyclyl) groups, —C(=O)—N(heterocyclyl)$_2$ groups, —C(=O)—N(alkyl)(heterocyclyl) groups, —C(=O)—N(aryl)(heterocyclyl) groups, substituted and unsubstituted heterocyclylaminoalkyl groups, substituted and unsubstituted hydroxyalkyl group, substituted and unsubstituted alkoxyalkyl groups, substituted and unsubstituted aryl oxyalkyl groups, and substituted and unsubstituted heterocyclyloxyalkyl groups;

$R^{18}$, $R^{23}$, $R^{24}$, and $R^{25}$ may be the same or different and are independently selected from the group consisting of H, —NH$_2$, —NH(alkyl) groups, —NH(aryl) groups, —N(alkyl)$_2$ groups, —N(aryl)$_2$ groups, —N(alkyl)(aryl) groups, —NH(heterocyclyl) groups, —N(heterocyclyl)(alkyl) groups, —N(heterocyclyl)(aryl) groups, N(heterocyclyl)$_2$ groups, substituted and unsubstituted alkyl groups, substituted and unsubstituted aryl groups, —OH, substituted and unsubstituted alkoxy groups, substituted and unsubstituted aryloxy groups, substituted and unsubstituted heterocyclyl groups, —NHOH, —N(alkyl)OH groups, —N(aryl)OH groups, —N(alkyl)O-alkyl groups, —N(aryl)O-alkyl groups, —N(alkyl)O-aryl groups, and —N(aryl)O-aryl groups; and $R^{22}$ is selected from the group consisting of substituted and unsubstituted alkyl groups, substituted and unsubstituted aryl groups, and substituted and unsubstituted heterocyclyl groups;

and further wherein at least one of $R^5$, $R^6$, $R^7$, or $R^8$ is a substituted or unsubstituted heterocyclyl group.

3. The method of claim 2, wherein the receptor tyrosine kinase is VEGFR2.

4. The method of claim 2, wherein $R^1$ is F.

5. The method of claim 2, wherein at least one of $R^5$, $R^6$, $R^7$, and $R^8$ is a substituted or unsubstituted heterocyclyl group selected from morpholine, piperazine, piperidine, or pyridine.

* * * * *